US012806228B2

(12) United States Patent
Harris

(10) Patent No.: US 12,806,228 B2
(45) Date of Patent: Nov. 24, 2026

(54) OPIOID-FREE COMPOSITIONS FOR ANESTHESIOLOGICAL APPLICATIONS AND RELATED METHODS AND SYSTEMS

(71) Applicant: Vaporworks Nursing Anesthesia Inc., Monrovia, CA (US)

(72) Inventor: Julia Harris, Monrovia, CA (US)

(73) Assignee: Vaporworks Nursing Anesthesia Inc., Monrovia, CA (US)

( * ) Notice: Subject to any disclaimer, the term of this patent is extended or adjusted under 35 U.S.C. 154(b) by 0 days.

(21) Appl. No.: 17/510,383

(22) Filed: Oct. 26, 2021

(65) Prior Publication Data

US 2022/0218740 A1 Jul. 14, 2022

Related U.S. Application Data

(60) Provisional application No. 63/105,340, filed on Oct. 25, 2020.

(51) Int. Cl.

| | |
|---|---|
| ***A61K 33/06*** | (2006.01) |
| ***A61K 31/135*** | (2006.01) |
| ***A61K 31/167*** | (2006.01) |
| ***A61K 31/245*** | (2006.01) |
| ***A61K 31/4164*** | (2006.01) |
| ***A61K 31/573*** | (2006.01) |
| ***A61P 25/36*** | (2006.01) |

(52) U.S. Cl.
CPC ............ *A61K 33/06* (2013.01); *A61K 31/135* (2013.01); *A61K 31/167* (2013.01); *A61K 31/245* (2013.01); *A61K 31/4164* (2013.01); *A61K 31/573* (2013.01); *A61P 25/36* (2018.01)

(58) Field of Classification Search
CPC .... A61K 31/573; A61K 33/06; A61K 31/167; A61K 31/135
See application file for complete search history.

(56) References Cited

U.S. PATENT DOCUMENTS

| | | | | |
|---|---|---|---|---|
| 6,310,094 | B1 * | 10/2001 | Liu | A61P 9/06 514/538 |
| 8,858,961 | B2 | 10/2014 | Graham et al. | |
| 2018/0235942 | A1 * | 8/2018 | During | A61K 9/08 |
| 2020/0230120 | A1 * | 7/2020 | Worthington | A61K 31/445 |

OTHER PUBLICATIONS

Deng, Methods Find Exp Clin Pharmacol, 28, 10, 2006 abstract (Year: 2006).*

Magnesium Sulfate (Magnesium Sulfate Injection) Side Effects, Interactions, Warning, Dosage & Uses Sep. 20, 2017 (Year: 2017).*

Mauermann, Best Practice and Research Clinical Anesthesiology, 31, 2017 (Year: 2017).*

Villalobos et al., "Opioid-Free Anesthesia (OFA) in super-obese Mexican Patients Undergoing Bariatric Surgery, with the Protocol of Sint Jan Brugge," Surgery for Obesity and Related Diseases, Elsevier, NL, vol. 14, No. 11, 2018, pp. 1-2.

Devine et al., "Opiod-Free Anesthesia for Lung Cancer Resection: A Case-Control Study," Journal of Cardiothoracic and Vascular Anethesia, Elsevier, vol. 34, No. 11, 2020, pp. 3036-3040.

Mulier et al., "Impact of Opioid-Free Anesthesia on Complications After Deep Inferior Epigastric Perforator Flap Surgery: A Retrospective Cohort Study," Journal of Plastic Reconstructive and Aesthetic Surgery, vol. 74, No. 3, 2020, pp. 504-511.

Bryskin et al., "Dexmedetomidine and Magnesium Sulfate in the Perioperative Management of a Child Undergoing Laparoscopic Resection of Bilateral Pheochromocytomas," Journal of Clinical Anesthesia Butterworth Publishers, vol. 22, No. 2, 2010, pp. 126-129.

Beloeil et al., "Opioid-Free Anesthesia," Bailliere's Best Practice and Research, Clinical Anesthesiology, vol. 33, No. 3, 2019, pp. 353-360.

International Application No. PCT/IB2021/062312, International Search Report and Written Opinion mailed Apr. 20, 2022, 12 pages.

Jan Mulier, "OFAM (Opioid Free Anesthesia Mixture) (Mulimix)—Keep it Simple," 2017, pp. 1-2.

Mclott Mix, "Cocktail Maintenance Infusion," 2019, pp. 1.

Unanymous, "Product Mongraph APO-Clodnidine Clonidine Hydrochloride Tablets USP 0.1 mg and 0.2mg," , 2020 pp. 1-26.

Mulier et al., "OFA for General Anesthesia Deep and Awake Sedation," OFAM (opioid free general anesthesia mixture) (Mulimix) Multimodal anaesthesia, ResearchGate, 2019, pp. 1-4.

European Application No. 21840689.0, European Examination Report mailed Oct. 14, 2024, 7 pages.

Japanese Application No. 2023-549156, Japanese Office Action mailed Mar. 3, 2026, 7 pages.

A De Castro, "Opioid Free Anaesthesia," University of Kwazulu-Natal School of Clinical Medicine Discipline of Anesthesiology and Critical Care, 2016, No. 5, pp. 1-22.

Schenkel et al., "Opioid-Free Anesthesia: Physico Chemical Stability Studies on Multi-Analyte Mixtures Intended for Use in Clinical Anesthesiology", Hospital Pharmacy, 2021#05}, vol. 57, No. 2, pp. 246-252.

Baek et al., "Opioid-free anesthesia with a mixture of dexmedetomidine, ketamine, and lidocaine in one syringe for surgery in obese patients", Journal of International Medical Research, 2020, vol. 48, No. 10, pp. 1-8.

Raza et al., "Preoperative Lidocaine Infusion for the Pain Management in Laparotomy Procedures: a Randomized Control Trial", The Professional Medical Journal, 2019, vol. 26, No. 6, pp. 924-928.

(Continued)

*Primary Examiner* — Susan T Tran
*Assistant Examiner* — William Craigo
(74) *Attorney, Agent, or Firm* — Liang & Hennessey LLP; Stanley D. Liang

(57) ABSTRACT

Opioid-free compositions, methods and systems are described. The compositions comprise magnesium salt, an alpha-2 agonist, a sodium channel inhibitor, and optionally an NMDA antagonist, a beta-blocker, and/or a corticosteroid, together with a pharmaceutically acceptable vehicle, carrier, or excipient. The compositions are suitable for peri-operative and intra-operative methods for a patient undergoing a medical or surgical procedure.

2 Claims, 15 Drawing Sheets

(56) References Cited

OTHER PUBLICATIONS

Kwok et al., "Preoperative Ketamine Improves Postoperative Analgesia After Gynecologic Laparoscopic Surgery", Anesthesia & Analgesia, 2004, vol. 98, No. 4, pp. 1044-1049.
Tang et al., "Dexmedetomidine in perioperative acute pain management: a non-opioid adjuvant analgesic" Journal of Pain Research, 2017, vol. 10, pp. 1899-1904.
Atar et al., "Preoperative effects of magnesium sulfate on hemodynamics and muscle relaxation" Journal of Surgery and Medicine, 2021, vol. 5, No. 9, pp. 862-866.
Giannoni et al., "Decadron with Preemptive Analgesia Improves Tonsillectomy Pain", Otolaryngology-Head and Neck Surgery, 2001, vol. 125, No. 2, p. P53.

* cited by examiner

| 164 Patient | OFA (82 patient) | Non-OFA (82 Matched Pts) |
|---|---|---|
| # Pts. Given Opioids in PACU | 24 patient | 30 patients |
| Unit per PACU Pt. | 29 mg/pt | 45mg/pt |
| Score on Arrival | 8.3 | 8.7 |
| Score on Discharge | 9.6 | 9.4 |

PACU

FIG.4

2015-2018
- 2.66 days (traditional care)
- 1.86 days (OFA/post-op opioid-sparing pain management)
- 0.81 Decrease in length of stay 2018-2019
- 1.27 days for OFA/post-op opioid-sparing pain management group
- 1.39 Decreased LOS from (traditional care)

ADJUSTED COST SAVINGS

| Factor | Estimated Savings per day | 1.39 (days saved) | 26 (number of surgeries) |
|---|---|---|---|
| Estimated Hospital Cost | $1335 | 1883.45 | 48,969.70 |

Updated 10/2019

FIG. 6

"Traditional" Costs

| **Traditional** | | | **$ Dosing** | | **$ Single Vial** |
|---|---|---|---|---|---|
| Midazolam | 1mg/ml | 1 | $0.45 | 2ml | $0.45 |
| Fentanyl | 100mcg | 1 | $0.45 | 2ml | $0.45 |
| Propofol | 10mg/ml | 2 | $3.30 | 20ml | $1.65 |
| Dexamethasone | 4mg/ml | 1 | $0.80 | 5ml | $0.80 |
| Ondansetron | 2mg/ml | 1 | $0.90 | 2ml | $0.90 |
| Sevoflurane | % | 0.2 | $12.60 | 250ml | $63 |
| Lidocaine | 1% | 0.25 | $0.31 | 20ml | $1.25 |
| Ketamine | 50mg/ml | 0.1 | $0.53 | 10ml | $5.30 |
| Ketorolac | 30mg/ml | 2 | $1.60 | 1ml | $0.80 |
| | | | **$20.94** | | **$24.20** |

FIG. 7

| OFA | | price/unit | | | $ Dosing | | Single Vial |
|---|---|---|---|---|---|---|---|
| Propofol | 10mg/ml | $1.65 | 20ml | 5 | $8.25 | 5 | $8.90 |
| Dexmedetomidine | 100mcg/ml | $3.50 | 2ml | 0.225 | $0.78 | 1 | $3.50 |
| Lidocaine | 1% | $1.25 | 20ml | 1 | $1.25 | 1 | $1.25 |
| Ketamine | 50mg/ml | $5.30 | 10ml | 0.1 | 0.53 | 1 | $5.30 |
| Magnesium | 5gm/10ml | $1.75 | 10ml | 0.4 | $0.70 | 1 | $1.75 |
| Pregabalin | 50mg | $0.20 | Cap | 1 | $0.20 | 1 | $0.20 |
| Celecoxib | 200mg | $0.20 | Cap | 2 | $0.40 | 2 | $0.40 |
| Acetaminophen | 500mg | $0.01 | Cap | 2 | $0.01 | 2 | $0.01 |
| Esmolol | 10mg | $2.50 | 10ml | 0.1 | $0.25 | 1 | $2.50 |
| **OFA Pricing** | | | | | $12.37 | | $23.81 |

OFA Pricing per shared vial ($ dosing) and when using each vial as a single use

Pricing updated 10/2021

FIG. 8

Updated: 10/2021

| Drug | | Price/unit | | Drug | | Price/unit | |
|---|---|---|---|---|---|---|---|
| Acetaminophen | 500mg | $0.01 | Cap | Ketorolac | 30mg/ml | $0.80 | 1ml |
| Acetaminophen injection (Ofirmev) | 1gm | $7.00 | 100ml | Lidocaine | 1% | $1.25 | 20ml |
| Bupivacaine Liposome (Exparel) | 1.3% | $190/350 | 10ml/20ml | Mg+ | 0.5gm/ml | $1.75 | 10ml |
| Celecoxib | 200mg | $0.20 | Cap | Midazolam | 1mg/ml | $0.45 | 2ml Vial |
| Desflurane | % | $135 | 240ml | Neostigmine | 1mg/ml | $4.00 | 10ml |
| Dexamethasone | 4mg/ml | $0.80 | 5ml | Ondansetron | 2mg/ml | $0.90 | 2ml Vial |
| Dexamethasone (PF) | 10mg/ml | $1.60 | 1ml | Pregabalin | 50mg | $0.20 | Cap |
| Dexmedetomidine | 100mcg/ml | $3.50 | 2ml | Promethazine | 25mg/ml | $1.00 | 1ml |
| Ephedrine | 50mg | $11.00 | 1ml | Propofol | 10mg/ml | $1.65 | 20ml Vial |
| Esmolol | 10mg | $2.50 | 10ml | Ropivacaine | 0.5% | $3.50 | 30ml |
| Fentanyl | 100mcg | $0.45 | 2ml Amp | Sevoflurane | % | $63.00 | 250ml |
| Glycopyrrolate | 0.2mg/ml | $1.80 | 1ml | Sugammadex | 200mg/ml | $105.00 | 2ml |
| Ketamine | 50mg/ml | $5.30 | 10ml | Tranexamic acid | 1gm/10ml | $5.30 | 10ml Vial |

Pricing updated:

FIG. 9

OFA Preemptive Analgesia Loading Dose Syringe:

| Syringe Content | Volume | Dose / Kg |
|---|---|---|
| Lidocaine 44mg/2.2ml | 2.2ml | 0.4mg/kg |
| Magnesium 3 GM/6ml | 6.0ml | 30mg/kg |
| Dexmedetomidine 30mcg/0.3ml | 0.3ml | 0.3mcg/kg |
| Decadron 15mg/1.5ml | 1.5ml | 0.15mg/kg |

TOTAL VOLUME: 10ml

Dose = 0.1ml/kg over 15-30 minutes = ____________ ml

Date:_________________ Time:_______________ Initials:_____________

PT. Name:_____________________________________________________

*Created by: Julia Harris 10/2019*

FIG. 10

Opioid Free Anesthesia Infusion
100ml IV Bag

| Medications & Vial Concentrations | Rate | Additives: Doses and Volume | | |
|---|---|---|---|---|
| Lidocaine 2% 20mg/ml | mg/kg/hr mg: Volume: | [] 1 100mg ***5ml*** | [] 1.5 150mg ***7.5ml*** | [] 2 200mg ***10ml*** |
| Mg++ 0.5 gm/ml | mg/kg/hr gm: Volume: | [] 5 0.5gm ***1ml*** | [] 10 1gm ***2ml*** | |
| *Dexmedetomidine 100 mcg/ml | mcg/kg/hr mcg: Volume: | [] 0.3 30mcg ***0.3ml*** | [] 0.4 40mcg ***0.4ml*** | [] 0.5 50mcg ***0.5ml*** |
| Ketamine 50mg/ml | mg/kg/hr mg: Volume: | [] 0.25 25mg ***0.5ml*** | [] 0.375 37.5mg ***0.75ml*** | [] 0.5 50mg ***1ml*** |
| Esmolol HCl 10mg/ml | mcg/kg/min mg: Volume: | [] 3 18mg ***1.8ml*** | [] 5 30mg ***3ml*** | [] 10 60 ***6ml*** |

**Total Additive Volume:
_________+__________+_________=

*volume to be removed from bag before injecting additives:*
_________*ml*

Infusion rate = 1ml/kg/hr = ______________ml/hr

Date:___________ Time: _________

Initials:______

Pt. Name: __________________________________

*Instructions:*

1) Remove fluid from IV bag equal to the **total additive volume
2) Add medications as selected above
3) Infusion rate: 1cc/kg/hr (patient ideal body weight)

**To increase concentration of dexmedetomidine:*
*add additional 10mcg (0.1ml) for every incremental increase of 0.1 mcg/ml/hr*

*Created by Julia Harris MSN, CRNA 10/2019*

FIG. 11

OPIOID-FREE COMPOSITIONS FOR ANESTHESIOLOGICAL APPLICATIONS AND RELATED METHODS AND SYSTEMS

1. BACKGROUND

Opioids are typically the drug of choice for anesthesia in view of their known effects and versatility in the practice of anesthesia and pain management.

Opioids administration, however, is associated with several side effects that can lead to significant morbidity and mortality as well as additional cost for post operational care.

Despite the advancement in anesthesiology, identification of drugs allowing effective anesthesia while minimizing side effects and complications associated with opioids administration, is still challenging.

2. SUMMARY OF THE DISCLOSURE

Provided herein are opioid-free compositions having anesthetic properties and to related method and system for anesthesiological applications, which allows in several embodiments performing effective anesthesia on an individual while reducing up to minimizing side effects and complications associated with opioids administration.

According to a first aspect an opioid-free pre-operative pharmaceutical composition is described. The opioid-free pre-operative composition comprises:

a magnesium ($Mg^{2+}$) salt, such as magnesium sulfate, an alpha-2 agonist, such as dexmedetomidine, and optionally a sodium channel inhibitor, such as lidocaine, and/or a N-methyl-D-aspartate receptor (NMDA) inhibitor, such as ketamine, and/or a corticosteroid, such as Dexamethasone, together with a pharmaceutically acceptable vehicle, carrier, or excipient. In the opioid-free pre-operative composition, the magnesium salt, alpha-2 agonist and optionally the sodium channel inhibitor, NMDA antagonist, and/or corticosteroid are present in an effective amount for treating anxiety, and/or inducing sedation, and/or analgesia of the individual in the pre-operative stage of a medical or surgical procedure, in particular when used in connection with the pre-operative methods of the disclosure.

According to a second aspect, a method is described for an opioid-free pre-operative treatment of an individual undergoing a medical or surgical procedure, the method comprising:

administering to the individual an effective amount of:

a magnesium salt, such as magnesium sulfate, in an amount ranging from 5 to 50 mg/kg Ideal Body Weight (IBW), an alpha-2 agonist, such as dexmedetomidine, in an amount ranging from 0.1 to 1 mcg/kg IBW, and optionally a sodium channel inhibitor, such as lidocaine, in an amount ranging from 0.1 to 2 mg/kg IBW, and/or a corticosteroid, such as Dexamethasone, in an amount ranging from 0.01 to 0.2 mg/kg IBW and/or an NMDA antagonist other than Mg, such as ketamine, in an amount ranging from 0 to 0.5 mg/kg IBW, the magnesium salt, alpha-2 agonist, and optionally the sodium channel inhibitor, corticosteroid, and NMDA being administered to the individual in combination in an amount effective for treating anxiety, and/or inducing sedation, and/or analgesia of the individual in the pre-operative stage of a medical or surgical procedure.

In various embodiments, the administering step comprises administering to the individual a pre-operative composition of the disclosure. In various embodiments, the administering step comprises a substep of combining the magnesium salt, the alpha-2 agonist, and optionally the sodium channel inhibitor, NMDA antagonist other than magnesium salt, and/or corticosteroid to prepare the pre-operative composition.

According to a third aspect, an opioid-free pre-operative system is described for an opioid-free pre-operative treatment of an individual. The opioid-free pre-operative system comprises:

a magnesium ($Mg^{2+}$) salt, such as magnesium sulfate, an alpha-2 agonist, such as dexmedetomidine.

and optionally a sodium channel inhibitor, such as lidocaine and/or procaine, and/or an NMDA antagonist other than the magnesium salt, such as ketamine, and/or a corticosteroid, such as Dexamethasone, comprised in an effective amount for simultaneous, combined or sequential use to induce anesthesia, sedation and/or analgesia of the individual in a method for an opioid-free pre-operative treatment as described herein.

According to a fourth aspect an opioid-free intra-operative pharmaceutical composition is described. The opioid-free intra-operative composition comprises:

a magnesium salt, such as magnesium sulfate, an alpha-2 agonist, such as dexmedetomidine, a sodium channel inhibitor, such as lidocaine, and optionally a N-methyl-D-aspartate receptor inhibitor, such as ketamine, and/or a beta-blocker, such as esmolol, together with a pharmaceutically acceptable vehicle, carrier, or excipient. In the intra-operative composition, the magnesium salt, alpha-2 agonist, sodium channel inhibitor, and optionally the NMDA antagonist other than magnesium salt and beta-blocker are present in the composition in an effective amount to induce and/or maintain analgesia, anesthesia, and/or sedation, as well as maintain hemodynamic stability of the individual in the intra-operative stage of the medical or surgical procedure.

According to a fifth aspect, a method is described for an opioid-free intra-operative treatment of an individual undergoing a medical or surgical procedure, the method comprises:

administering to the individual an effective amount of:

a magnesium salt, such as magnesium sulfate, in an amount ranging from 1 to 20 mg/kg/hr Ideal Body Weight (IBW), an alpha-2 agonist, such as dexmedetomidine, in an amount ranging from 0.01 to 1 mcg/kg/hr IBW, a sodium channel inhibitor, such as lidocaine, in an amount ranging from 0.1 to 3 mg/kg/hr IBW, and optionally a beta-blocker, such as esmolol, in an amount ranging from 3 to 300 mcg/kg/min or from 3 to 20 mcg/kg/min IBW, and/or an NMDA antagonist other than the magnesium salt, in an amount ranging from 0 to 0.5 mg/kg/hr IBW.

The magnesium salt, alpha-2 agonist, and sodium channel inhibitor, and optionally the beta-blocker and NMDA antagonist other than the magnesium salt being administered to the individual in an effective amount to induce and/or maintain analgesia, anesthesia, and/or sedation, as well as maintain hemodynamic stability of the individual in the intra-operative stage of the medical or surgical procedure.

In various embodiments, the administering step comprises administering to the individual an opioid-free intra-operative composition of the disclosure. In various embodiments, the administering step comprises combining the magnesium salt, the alpha-2 agonist, the sodium channel inhibitor, and optionally the N-methyl-D-aspartate receptor inhibitor, and/or the beta-blocker to prepare an intra-operative composition. According to a sixth aspect, an opioid-free intra-operative system is described for an opioid-free intra-operative treatment of an individual undergoing a medical or surgical procedure. The opioid-free intra-operative system comprises:

a magnesium salt, such as magnesium sulfate, an alpha-2 agonist, such as dexmedetomidine, and a sodium channel inhibitor, such as lidocaine or procaine, and optionally a N-methyl-D-aspartate receptor inhibitor, such as ketamine, and/or a beta-blocker, such as esmolol, in an effective amount for simultaneous, combined or sequential administration to induce and/or maintain analgesia, anesthesia, and/or sedation, as well as maintain hemodynamic stability of the individual in the intra-operative stage of the medical or surgical procedure according to the method for an opioid-free intra-operative treatment of the disclosure.

According to a seventh aspect, a method is described for an opioid-free peri-operative treatment of an individual undergoing a medical or medical or surgical procedure. The method comprises:

administering to the individual an effective amount of an opioid-free pre-operative treatment according to any one of the methods described herein; and administering to the individual an effective amount of an opioid-free intra-operative treatment according to any one of the methods described herein.

In various embodiments, the administering of the opioid-free pre-operative treatment step comprises administering to the individual a pre-operative composition of the disclosure. In various embodiments, the administering of the opioid-free pre-operative treatment step comprises a substep of combining the magnesium salt, the alpha-2 agonist, and optionally the sodium channel inhibitor, and/or NMDA antagonist other than magnesium salt, and/or corticosteroid to prepare the pre-operative composition.

In various embodiments, the administering of the opioid-free intra-operative treatment step comprises administering to the individual an intra-operative composition of the disclosure. In various embodiments, the administering of the opioid-free intra-operative treatment step comprises a substep of combining the magnesium salt, the alpha-2 agonist, the sodium channel inhibitor, and optionally the N-methyl-D-aspartate receptor inhibitor, and/or the beta-blocker.

According to an eighth aspect, an opioid-free peri-operative system is described for an opioid-free intra-operative treatment of an individual undergoing a medical or surgical procedure. The opioid-free peri-operative system comprises:

an opioid-free pre-operative system described herein, and an opioid-free intra-operative system described herein, in an effective amount for simultaneous, combined or sequential administration to induce and maintain anesthesia, sedation, analgesia and/or stable vital signs of the individual and contribute to the anesthetic depth for surgery according to the method for an opioid-free peri-operative treatment described herein.

In various embodiments of the opioid-free peri-operative system, the magnesium salt, alpha-2 agonist, and optionally the sodium channel inhibitor, and/or NMDA antagonist other than the magnesium salt, and/or corticosteroid of the opioid-free pre-operative system, are comprised in a composition configured to facilitate their rapid and correct dosing.

In various embodiments of the opioid-free peri-operative system, the magnesium salt, the alpha-2 agonist, the sodium channel inhibitor and optionally, the N-methyl-D-aspartate receptor inhibitor, and/or the beta-blocker of the opioid-free intra-operative system, are comprised in a composition configured to facilitate their rapid and correct dosing.

The opioid-free compositions, methods and systems herein described allow in several embodiments to eliminate or reduce the need for post-operative opioid consumption thereby reducing exposure and risk of developing opioid use disorder.

The opioid-free compositions, methods, and systems herein described allow in several embodiments to prevent or mitigate pain associated with surgical operations. The opioid-free compositions, methods and systems herein described allow in several embodiments to minimize side effects associated to opioid administration such as respiratory depression, nausea/vomiting, and constipation.

The opioid-free compositions, methods, and systems herein described allow in several embodiments to minimize immunosuppression associated with opioids administration affecting the outcome of surgery including a possible increased risk of infection and increased risk of metastasis in cancer population (ncbi.nlm.nih.gov/pmc/articles/PMC5902248/ on the world wide web).

The opioid-free compositions, methods, and systems herein described allow in several embodiments to eliminate acute opioid induced tolerance and hyperalgesia, further perpetuated by over prescription secondary to suboptimal post-operative pain control.

The opioid-free compositions, methods, and systems herein described allow in several embodiments to significantly reduce morbidity, mortality, and additional post-operative healthcare cost associated with opioid administration.

The opioid-free compositions, methods, and systems described herein can be used in connection with various applications in which anesthetic or analgesic effect is desired. For example, the opioid-free compositions, methods, and systems herein described can be used to treat individuals who are about to undergo a medical or surgical procedure. Additional exemplary applications include uses of the compositions herein described in several fields including basic biology research, applied biology, bio-engineering, medical research, therapeutics, and in additional fields identifiable by a skilled person upon reading of the disclosure.

The details of one or more embodiments of the disclosure are set forth in the accompanying drawings and the description below. Other features, objects, and advantages will be apparent from the description and drawings, and from the claims.

3. BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 1 shows a schematic representation showing different stage of a medical or surgical procedure for opioid-free anesthesia, including surgical time, anesthesia time and peri-operative time. (From N. M. Elkassabany and E. R. Mariano, Anaesthesia 2019, 74, 560-563).

FIG. 2 shows a schematic representation of an exemplary model for the excitotoxic formation of dark neurons in the dorsal horn of the spinal cord from peripheral nerve injury or repeated morphine administration. (From Mayer, D. J., Mao, J., Holt, J., Price, D. D. Proc Natl Acad Sci USA. 1999 Jul. 6; 96(14): 7731-7736).

FIG. 3 shows an overview of clinically used pharmacotherapeutic approaches that lead to the attenuation of mechanisms of spinal pain amplification. These approaches comprise the use of clonidine and antidepressants, local anesthetics (LA) (such as intravenous (IV) lidocaine), ketamine, non-steroidal anti-inflammatory drugs (NSAIDs), gabapentin and pregabalin. (From Deumens, Steyaert, Forget et al., Progress Neurobio. 2012).

FIG. 4 compares the PACU opioid consumption and Aldrete scores for surgical patients who received either opioid-free anesthesia (OFA) of the disclosure or non-opioid-free anesthesia (Non-OFA) (see Example 16).

FIG. 5 shows the results of a retrospective analysis of one hundred and forty patients who underwent total knee replacement surgery at a hospital. Patients who received OFA of the disclosure and/post-operative opioid-sparing pain management experienced a fifty percent reduction in hospital length of stay (LOS) after surgery compared to traditional care. These patients were able to go home on average 1.39 days sooner than patients who had received traditional anesthesia services (see Example 17).

FIG. 6 shows the cost savings associated with the decreased post-operative length of stay as described in FIG. 5.

FIG. 7 shows the costs for administering typical "traditional" opioid-based anesthesia when a single vial is used for each patient ($ Single Vial) and the cost when vials are able to be utilized for more than one patient "$ Dosing." Many hospitals only allow splitting individual vials into multiple doses to be done in the pharmacy under strict sterile conditions.

FIG. 8 shows the costs for exemplary ingredients in the opioid-free composition of the disclosure and additional agents that can be used in conjunction with the opioid-free compositions. FIG. 8 shows the costs with respect to concentration and administration of an opioid-free composition when a single vial is used for each patient ($ Single Vial) and the cost when vials are able to be utilized for more than one patient "$ Dosing." Many hospitals only allow splitting individual vials into multiple doses to be done in the pharmacy under strict sterile conditions.

FIG. 9 shows "traditionally used" anesthesia medications with respect to unit price and manufactured concentrations.

FIG. 10 shows an exemplary OFA composition for Preemptive Analgesia Loading Dose Syringe as described herein, wherein the composition comprises lidocaine, $Mg^{2+}$ salt, dexmedetomidine, and Dexamethasone.

FIG. 11 shows alternative combination of Opioid-free Anesthesia Infusion OFA composition in a 100 mL IV bag, wherein the composition comprises lidocaine, Mg, dexmedetomidine, ketamine, and esmolol-HCl.

Figure 12:
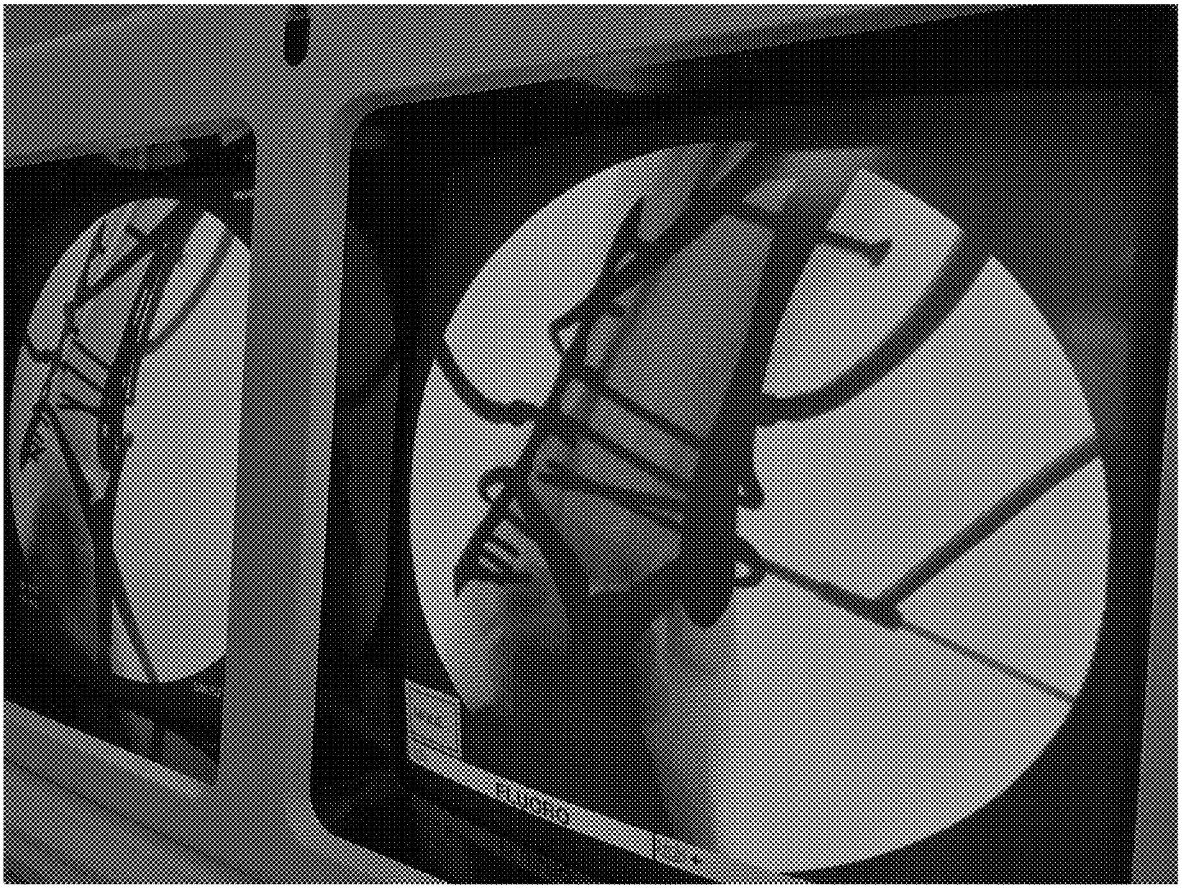

FIG. 12 shows a picture of an ankle following an ankle fixation surgical procedure. The ankle fixation procedure was performed using an opioid-free composition of the disclosure. The patient experienced an uneventful post-operative course (see Example 18).

Figure 13:
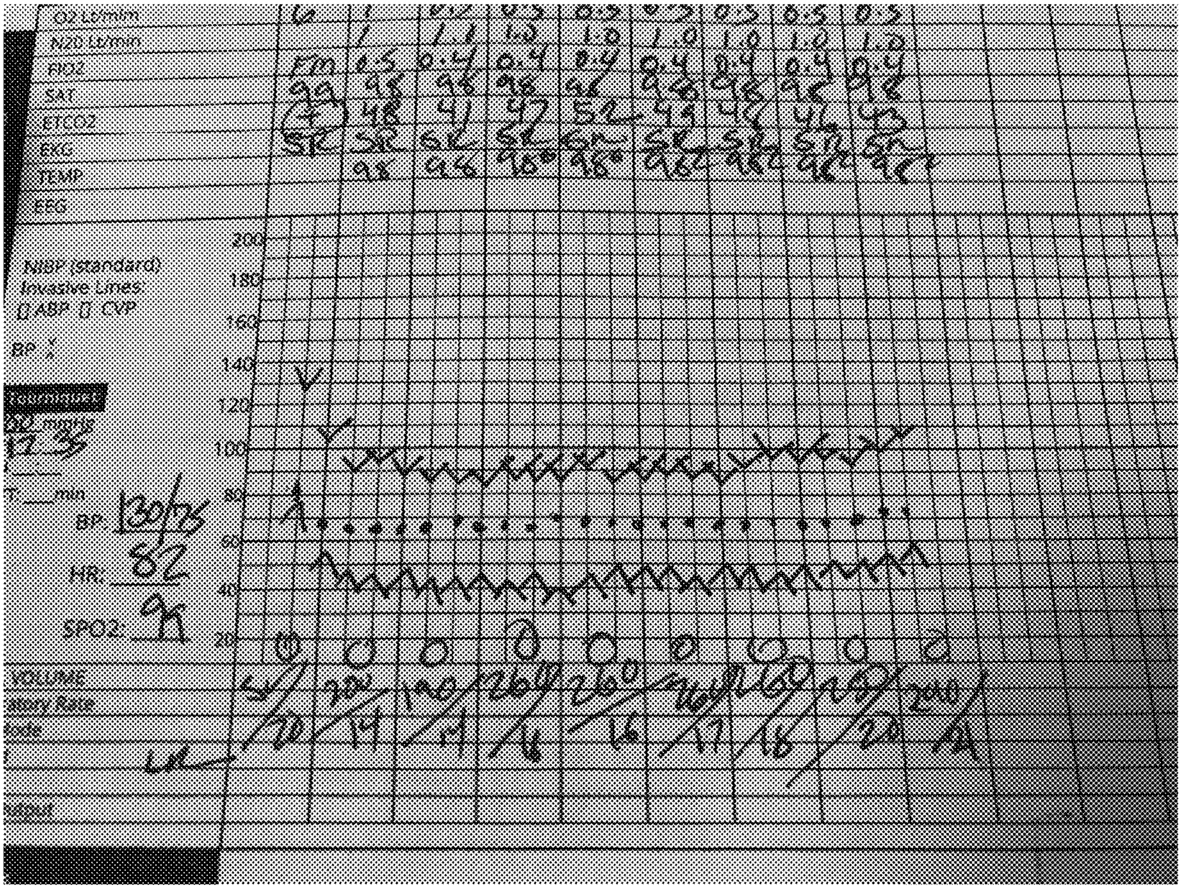

FIG. 13 shows a picture of the anesthetic record showing minimal changes in vital signs (sympathetic response) during surgery as shown in FIG. 12 (see Example 18).

Figure 14A:
Figure 14B:
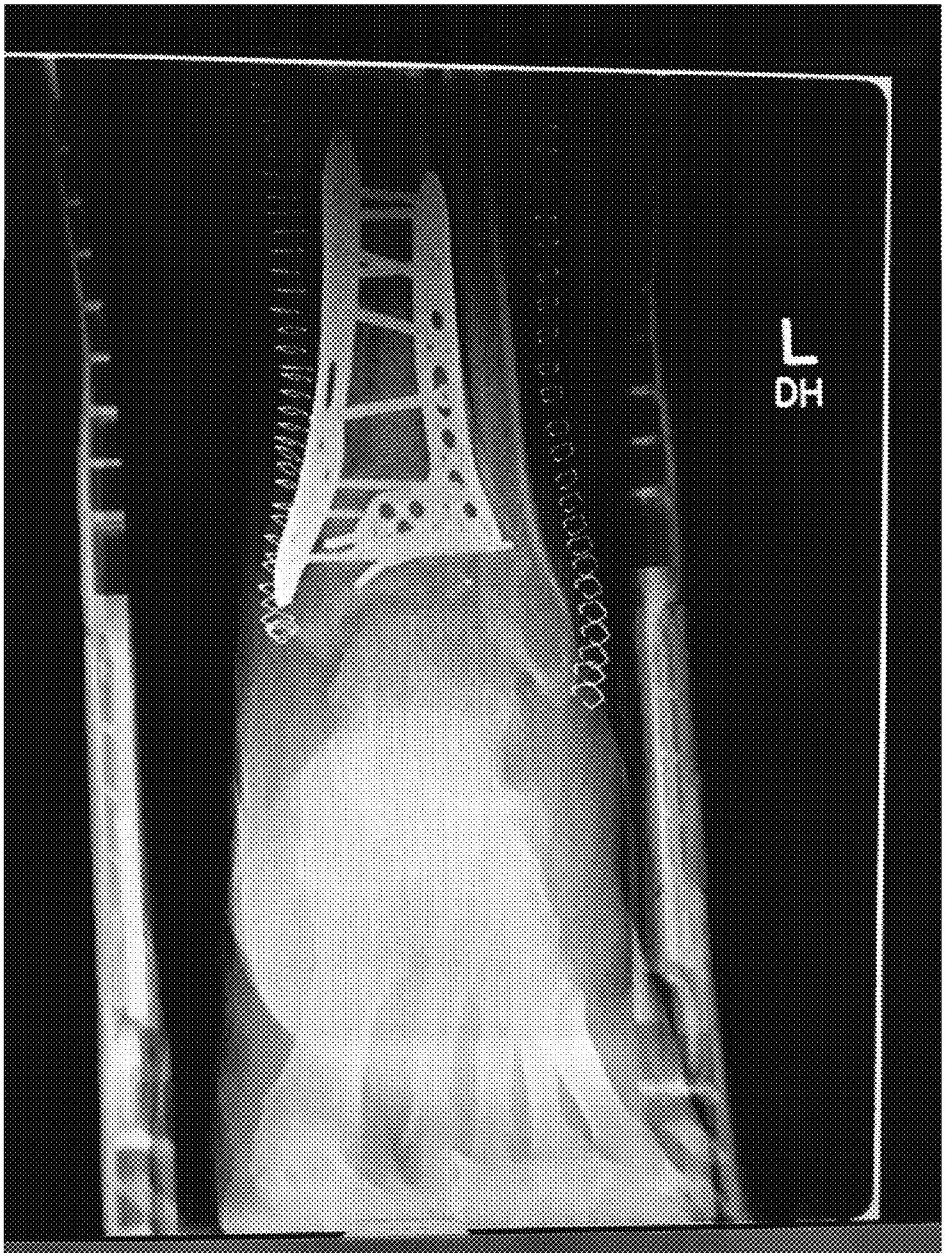

FIG. 14A shows a picture of a severe ankle fracture in a patient prior to surgery. FIG. 14B shows picture of the ankle following the fixation procedure. The ankle fixation surgery was performed using an opioid-free composition of the disclosure and without administering a peripheral nerve block (see Example 19). The patient reported no pain in the recovery unit and did not require rescue opioids during this period.

DETAILED DESCRIPTION

The invention includes the following:

(1.) An opioid-free pre-operative pharmaceutical composition comprising a magnesium ($Mg^{2+}$) salt, such as magnesium sulfate, and an alpha-2 agonist, such as dexmedetomidine, and optionally a sodium channel inhibitor, such as lidocaine, and/or a N-methyl-D-aspartate receptor (NMDA) inhibitor, such as ketamine, and/or a corticosteroid, such as Dexamethasone, together with a pharmaceutically acceptable vehicle, carrier, or excipient, wherein the magnesium salt, alpha-2 agonist, and optionally the sodium channel inhibitor and/or NMDA antagonist and/or corticosteroid are comprised in an effective amount for treating anxiety and/or inducing sedation, and/or analgesia.

(2.) The opioid-free pre-operative pharmaceutical composition of the above (1.), wherein the alpha-2 agonist is selected from dexmedetomidine, clonidine, fadolmidine, guanabenz, guanoxabenz, guanethidine, xylazine, tizanidine, medetomidine, methyldopa, methylnorepinephrine, norepinephrine, (R)-3-nitrobiphenyline, amitraz, detomidine, lofexidine, and medetomidine or any combination thereof.

(3.) The opioid-free pre-operative pharmaceutical composition of the above (1.) or (2.), wherein the alpha-2 agonist comprises dexmedetomidine.

(4.) The opioid-free pre-operative pharmaceutical composition of any one of the above (1.) to (3.), wherein the sodium channel inhibitor is selected from the group consisting of quinidine, ajmaline, procainamide, disopyramide, lidocaine, procaine, prilocaine, phenytoin, mexiletine, tocainide, encainide, flecainide, propafenone and moricizine or any combination thereof.

(5.) The opioid-free pre-operative pharmaceutical composition of any one of the above (1.) to (4.), wherein the sodium channel inhibitor comprises lidocaine and/or procaine, or any combination thereof.

(6.) The opioid-free pre-operative pharmaceutical composition of any one of the above (1.) to (5.), wherein the sodium channel inhibitor comprises lidocaine.

(7.) The opioid-free pre-operative pharmaceutical composition of any one of the above (1.) to (6.), wherein the NMDA antagonist other than magnesium salt is selected from the group consisting of ketamine, dextromethorphan (DXM), phencyclidine (PCP), and methoxetamine (MXE) or any combination thereof.

(8.) The opioid-free pre-operative pharmaceutical composition of any one of the above (1.) to (7.), wherein the NMDA antagonist other than magnesium salt comprises ketamine.

(9.) The opioid-free pre-operative pharmaceutical composition of any one of the above (1.) to (8.), wherein the corticosteroid is selected from the group consisting of cortisone, hydrocortisone, fludrocortisone acetate, prednisolone, prednisone, methylprednisolone, triamcinolone, Dexamethasone Sodium phosphate (Dexamethasone), betamethasone, triamcinolone acetonide, and fluorometholone or any combination thereof.

(10.) The opioid-free pre-operative pharmaceutical composition of any one of the above (1.) to (9.), wherein the corticosteroid comprises Dexamethasone Sodium phosphate.

(11.) The opioid-free pre-operative pharmaceutical composition of any one of the above (1.) to (10.), wherein: the alpha-2 agonist comprises dexmedetomidine, the sodium channel inhibitor comprises lidocaine or procaine, the NMDA antagonist comprises ketamine, the beta-blocker comprises esmolol, and the corticosteroid comprises Dexamethasone.

(12.) The opioid-free pre-operative pharmaceutical composition of any one of the above (1.) to (11.), wherein a concentration of the magnesium salt ranges from 1 mg/mL to 500 mg/mL.

(13.) The opioid-free pre-operative pharmaceutical composition of any one of the above (1.) to (12.), wherein a concentration of the magnesium salt ranges from 1 mg/mL to 300 mg/mL.

(14.) The opioid-free pre-operative pharmaceutical composition of any one of the above (1.) to (13.), wherein a concentration of the alpha-2 agonist ranges from 0.01 to 50 mcg/mL.

(15.) The opioid-free pre-operative pharmaceutical composition of any one of the above (1.) to (14.), wherein a concentration of the alpha-2 agonist ranges from 0.1 to 50 mcg/mL.

(16.) The opioid-free pre-operative pharmaceutical composition of any one of the above (1.) to (15.), wherein a concentration of the alpha-2 agonist ranges from 0.1 to 30 mcg/mL.

(17.) The opioid-free pre-operative pharmaceutical composition of any one of the above (1.) to (16.), wherein a concentration of the alpha-2 agonist ranges from 0.1 to 1 mcg/mL.

(18.) The opioid-free pre-operative pharmaceutical composition of any one of the above (1.) to (17.), wherein a concentration of the sodium channel inhibitor, ranges from 0.1 mg/mL to 35 mg/mL.

(19.) The opioid-free pre-operative pharmaceutical composition of any one of the above (1.) to (18.), wherein a concentration of the sodium channel inhibitor, ranges from 1 mg/mL to 20 mg/mL.

(20.) The opioid-free pre-operative pharmaceutical composition of any one of the above (1.) to (19.), wherein a concentration of the NMDA antagonist other than magnesium salt ranges from 0.01 mg/mL to 35 mg/mL.

(21.) The opioid-free pre-operative pharmaceutical composition of any one of the above (1.) to (20.), wherein a concentration of the NMDA antagonist other than magnesium salt from 0.1 mg/mL to 5.0 mg/mL.

(22.) The opioid-free pre-operative pharmaceutical composition of any one of the above (1.) to (21.), wherein a concentration of the corticosteroid ranges from 0.01 to 10 mg/mL.

(23.) The opioid-free pen-operative pharmaceutical composition of any one of the above (1.) to (22.), wherein a concentration of the corticosteroid ranges from 1 to 2.0 mg/mL.

(24.) A method for an opioid-free pre-operative treatment of an individual undergoing a medical or surgical procedure, the method comprising, administering to the individual an effective amount of a magnesium salt, such as magnesium sulfate in an amount ranging from 5 to 30 mg/kg/Ideal Body Weight (IBW), an alpha-2 agonist such as dexmedetomidine: in an amount ranging from 0.1 to 1 mcg/kg IBW, and optionally a sodium channel inhibitor, such as lidocaine, in an amount ranging from 0.1 to 2 mg/kg IBW, a corticosteroid, such as Dexamethasone in an amount ranging from 0.01 to 0.2 mg/kg IBW and/or an NMDA antagonist other than Mg, such as ketamine: in an amount ranging from 0 to 0.5 mg/kg IBW, the effective amount of the magnesium salt, alpha-2 agonist, and optionally sodium channel inhibitor, and/or corticosteroid and/or NMDA, administered to the individual in combination for treating anxiety and/or inducing sedation, and/or analgesia of the individual in the pre-operative stage of a medical or surgical procedure.

(25.) The method of the above (24.), wherein the administering of the opioid-free pre-operative treatment is performed by administering to the individual the pre-operative composition of any one of the above (1.) to (23.).

(26.) An opioid free pre-operative system for an opioid-free pre-operative treatment of an individual, the opioid-free pre-operative system comprising, a magnesium ($Mg^{2+}$) salt, such as magnesium sulfate, an alpha-2 agonist such as dexmedetomidine, and optionally a sodium channel inhibitor such as lidocaine and/or procaine, an NMDA antagonist other than magnesium salt such as ketamine, and/or corticosteroid such as Dexamethasone.

in an effective amount for simultaneous, combined or sequential use for treating anxiety and/or inducing sedation, and/or analgesia of the individual in a method for an opioid-free pre-operative treatment of the above 24 or 25.

(27.) The system of the above (26.), wherein the magnesium salt, alpha-2 agonist, and the optional sodium channel inhibitor, NMDA antagonist other than magnesium salt, and/or corticosteroid are comprised in a formulation and dosage configured to be combined to provide a pre-operative composition herein described before the administering.

(28.) An opioid-free intra-operative pharmaceutical composition, the opioid-free intra-operative composition comprising a magnesium ($Mg^{2+}$) salt such as magnesium sulfate, an alpha-2 agonist, such as dexmedetomidine, a sodium channel inhibitor such as lidocaine, and optionally a N-methyl-D-aspartate receptor (NMDA) inhibitor, such as ketamine, and/or a beta-blocker, such as esmolol, together with a pharmaceutically acceptable vehicle, carrier, or excipient, wherein the magnesium salt, alpha-2 agonist, sodium channel inhibitor, and the optional NMDA antagonist other than magnesium salt, beta-blocker are comprised in an effective amount to induce and/or maintain analgesia, anesthesia, and/or sedation, as well as maintain hemodynamic stability of an individual in the intra-operative stage of the medical or surgical procedure.

(29.) The opioid-free intra-operative pharmaceutical composition of the above (28.), wherein the alpha-2 agonist is selected from dexmedetomidine, clonidine, fadolmidine, guanabenz, guanoxabenz, guanethidine, xylazine, tizanidine, medetomidine, methyldopa, methylnorepinephrine, norepinephrine, (R)-3-nitrobiphenyline, amitraz, detomidine, lofexidine, and medetomidine or any combination thereof.

(30.) The opioid-free intra-operative pharmaceutical composition of the above (28.) or (29.), wherein the alpha-2 agonist comprises dexmedetomidine.

(31.) The opioid-free intra-operative pharmaceutical composition of any one of the above (28.) to (30.) wherein the sodium channel inhibitor is selected from the group consisting of quinidine, ajmaline, procainamide, disopyramide, lidocaine, procaine, prilocaine, phenytoin, mexiletine, tocainide, encainide, flecainide, propafenone and moricizine or any combination thereof.

(32.) The opioid-free intra-operative pharmaceutical composition of any one of the above (28.) to (31.), wherein the sodium channel inhibitor comprises lidocaine, procaine or any combination thereof.

(33.) The opioid-free intra-operative pharmaceutical composition of any one of the above (28.) to (32.), wherein the sodium channel inhibitor comprises lidocaine.

(34.) The opioid-free intra-operative pharmaceutical composition of any one of the above (28.) to (33.), wherein the NMDA antagonist other than magnesium salt is selected from the group consisting of ketamine, dextromethorphan (DXM), phencyclidine (PCP), and methoxetamine (MXE) or any combination thereof.

(35.) The opioid-free intra-operative pharmaceutical composition of any one of the above (28.) to (34.), wherein the NMDA antagonist other than magnesium salt comprises ketamine.

(36.) The opioid-free intra-operative pharmaceutical composition of any one of the above (28.) to (35.), wherein the alpha-2 agonist comprises dexmedetomidine, the sodium channel inhibitor comprises lidocaine or procaine, the NMDA antagonist comprises ketamine, and the beta-blocker such as esmolol.

(37.) The opioid-free intra-operative pharmaceutical composition of any one of the above (28.) to (36.), wherein a concentration of the magnesium salt ranges from 1 mg/mL to 500 mg/mL.

(38.) The opioid-free intra-operative pharmaceutical composition of any one of the above (28.) to (37.), wherein a concentration of the magnesium salt ranges from 1 mg/mL to 300 mg/mL.

(39.) The opioid-free intra-operative pharmaceutical composition of any one of the above (28.) to (38.), wherein a concentration of the alpha-2 agonist ranges from 0.01 to 50 mcg/mL.

(40.) The opioid-free intra-operative pharmaceutical composition of any one of the above (28.) to (38.), wherein a concentration of the alpha-2 agonist ranges from 0.1 to 30 mcg/mL.

(41.) The opioid-free intra-operative pharmaceutical composition of any one of the above (28.) to 38, wherein a concentration of the alpha-2 agonist ranges from 0.1 to 1 mcg/mL.

(42.) The opioid-free intra-operative pharmaceutical composition of any one of the above (28.) to (41.), wherein a concentration of the sodium channel inhibitor, ranges from 0.1 mg/mL to 35 mg/mL.

(43.) The opioid-free intra-operative pharmaceutical composition of any one of the above (28.) to (41.), wherein a concentration of the sodium channel inhibitor, ranges from 1 mg/mL to 3 mg/mL.

(44.) The opioid-free intra-operative pharmaceutical composition of any one of the above (28.) to (43.), wherein a concentration of the NMDA antagonist other than magnesium salt ranges from 0.01 mg/mL to 35 mg/mL.

(45.) The opioid-free intra-operative pharmaceutical composition of any one of the above (28.) to (43.), wherein a concentration of the NMDA antagonist other than magnesium salt from 0.1 mg/mL to 1.0 mg/mL.

(46.) The opioid-free intra-operative pharmaceutical composition of any one of the above (28.) to (45.), wherein the beta-blocker is selected from the group consisting of carvedilol, propranolol, esmolol, timolol, metoprolol, labetalol, atenolol, bisoprolol and nebivolol or any combination thereof.

(47.) The opioid-free intra-operative pharmaceutical composition of any one of the above (28.) to (46.), wherein the beta-blocker comprises esmolol.

(48.) The opioid-free intra-operative pharmaceutical composition of any one of the above (28.) to (47.), wherein a concentration of the beta-blocker ranges from 0.001 mg/mL to 20 mg/mL.

(49.) The opioid-free intra-operative pharmaceutical composition of any one of the above (28.) to (47.), wherein, a concentration of the beta-blocker ranges from 0.01 mg/mL to 18 mg/mL.

(50.) The opioid-free intra-operative pharmaceutical composition of any one of the above (28.) to (47.), wherein a concentration of the beta-blocker ranges from 0.05 mg/mL to 1.0 mg/mL.

(51.) A method for an opioid-free intra-operative treatment of an individual, undergoing a medical or surgical procedure, the method comprising, administering to the individual and effective amount of a magnesium salt such as magnesium sulfate in an amount ranging from about 1 mg/kg/hr to 10 mg/kg/hr Ideal Body Weight (IBW), an alpha-2 agonist, such as dexmedetomidine in an amount ranging from 0.01 to 1 mcg/kg/hr IBW, a sodium channel inhibitor such as lidocaine in an amount ranging from 0.1 to 3 mg/kg/hr IBW and optionally a beta-blocker, such as esmolol in an amount ranging from 3 to 300 mcg/kg/min or from 3 to 20 mcg/kg/min IBW, and/or an NMDA antagonist other than the magnesium salt, such as ketamine in an amount ranging from 0 to 0.5 mg/kg/hr IBW the effective amount of the magnesium salt, alpha-2 agonist, sodium channel inhibitor, and optionally beta-blocker, and/or NMDA antagonist other than the magnesium salt administered to the individual in combination to induce and/or maintain analgesia, anesthesia, and/or sedation, as well as maintain hemodynamic stability of the individual in the intra-operative stage of the medical or surgical procedure.

(52.) The method of the above (51.), wherein the administering of the opioid-free intra-operative treatment is performed by administering to the individual the intra-operative composition of any one of the above (28.) to (50.).

(53.) An opioid-free intra-operative system for an opioid-free intra-operative treatment of an individual, the opioid-free intra-operative system comprising, a magnesium ($Mg^{2+}$) salt, such as magnesium sulfate, an alpha-2 agonist, such as dexmedetomidine, a sodium channel inhibitor anesthetic, such as lidocaine and/or procaine, and optionally a N-methyl-D-aspartate receptor (NMDA) inhibitor, such as ketamine, and/or a beta-blocker, such as esmolol, in an effective amount for simultaneous, combined or sequential administration to induce and/or maintain analgesia, anesthesia, and/or sedation, as well as maintain hemodynamic stability of the individual in the intra-operative stage of the medical or surgical procedure according to the method for an opioid-free intra-operative treatment method of the above (51.) or (52.).

(54.) The system of the above (53.), wherein the magnesium ($Mg^{2+}$) salt, the an alpha-2 agonist such as dexmedetomidine, the sodium channel inhibitor anesthetic such as lidocaine and/or procaine, and optionally the N-methyl-D-aspartate receptor (NMDA) inhibitor such as ketamine, and/or the beta-blocker such as esmolol are comprised in a formulation and dosage configured to be combined to provide an intra-operative composition herein described before the administering.

(55.) A method to provide an opioid-free peri-operative treatment of an individual, undergoing a medical or surgical procedure, the method comprising, performing an opioid-free pre-operative treatment of an individual undergoing a medical or surgical procedure according to any one of the above (24.) or (25.); and performing an opioid-free intra-operative treatment of an individual undergoing a medical or surgical procedure according to any one of the above (51.) or (52.) and optionally administering to the individual a post-operative composition herein described for a time and under condition to treat pain and/or inflammation of the individual during a post-operative stage of the medical or surgical procedure.

(56.) The method of the above (55.), where performing the opioid-free pre-operative treatment is performed by administering to the individual the pre-operative composition of any one of the above (1.) to (23.).

(57.) The method of the above (55.), where performing the opioid-free intra-operative treatment is performed by administering to the individual the intra-operative composition of any one of the above (28.) to (50.).

(58.) An opioid-free peri-operative system is described for an opioid-free peri-operative treatment of an individual, the opioid-free peri-operative system comprising, an opioid-free pre-operative system of the above (26.) or (27.), and an opioid-free intra-operative system of the above (53.) or (54.), in an effective amount for simultaneous, combined or sequential administration to induce anesthesia and maintain stable vital signs of the individual according to the method for an opioid-free pre-operative treatment of the above (55.) or (56.).

(59.) The opioid-free peri-operative system of the above (58.), the magnesium salt, alpha-2 agonist, a sodium channel inhibitor anesthetic, and the optional NMDA antagonist other than magnesium salt, and/or corticosteroid of the opioid-free pre-operative system, are comprised in a formulation and dosage configured to be combined to provide a pre-operative composition herein described before the administering.

(60.) The opioid-free peri-operative system of the above (58.) or (59.), wherein the magnesium ($Mg^{2+}$) salt, the an alpha-2 agonist such as dexmedetomidine, the sodium channel inhibitor anesthetic such as lidocaine and/or procaine and optionally the N-methyl-D-aspartate receptor (NMDA) inhibitor such as ketamine, and/or the beta-blocker such as esmolol of the opioid-free pre-operative system, are comprised in a formulation and dosage configured to be combined to provide an intra-operative composition herein described before the administering (61.) The opioid-free peri-operative system of any one of the above (55.) to (60.) further comprising a calcium channel inhibitor, Cox inhibitor, GABA analogue, antidepressant, cannabidiol (CBD), and/or antiemetic agent.

(62.) The opioid-free peri-operative system of the above (61.), wherein the calcium channel inhibitor comprises verapamil or diltiazem.

(63.) The opioid-free peri-operative system of the above (61.) or (62.), wherein the Cox inhibitor is selected from the group consisting of Celecoxib (that is celexoxib), refecoxib (commonly known as vioxx), etoricoxib, valdecoxib, parecoxib, aspirin, diflunisal, ibuprofen, dexibuprofen, naproxen, fenoprofen, ketoprofen, indomethacin, tolmetin, diclofenac, sulindac, etodolac, ketorolac, piroxicam, meloxicam (meloxicam), tenoxicam, droxicam, mefenanmic acid, meclofenanmic acid, clonixin, licofelone, and paracetamol (acetaminophen) or any combination thereof.

(64.) The opioid-free peri-operative system of any one of the above (61.) to (63.), wherein the GABA analogue is selected from the group consisting of pregabalin, gabapentin, picamilon and progabide or any combination thereof.

(65.) The opioid-free peri-operative system of any one of the above (61.) to (64.), wherein the antidepressant is selected from the group consisting of (SNRIs), selective serotonin reuptake inhibitors (SSRIs), tricyclic antidepressants (TCAs), tetracyclic antidepressants (TeCA), monoamine oxidase inhibitors (MAOIs), noradrenaline and specific serotoninergic antidepressants (NASSAs).

(66.) The opioid-free peri-operative system of any one of the above (61.) to (65.), wherein the antidepressant comprises a serotonin and noradrenaline reuptake inhibitor (SNRIs) selecting from the group consisting of Venlafaxine, Cymbalta (Duloxetine), Venlafaxine XR, Venlafaxine ER, Desvenlafaxine, and Venlafaxine.

(67.) The opioid-free pen-operative system of any one of the above (61.) to (66.), wherein the antiemetic agent is selected from the group consisting of includes ondansetron, dolasetron, granisetron, palonosetron, promethazine, imenhydrinate, metoclopramide, and meclizine or any combination thereof.

4.1 Definitions

Unless clearly indicated otherwise, the following terms as used herein have the meanings indicated below.

The word "comprise" or variations such as "comprises" or "comprising" will be understood to imply the inclusion of a stated integer or groups of integers but not the exclusion of any other integer or group of integers.

The term "opioid" refers to a natural or synthetic compound that binds to an opioid receptor including agonists and antagonists. Opioid receptors are found principally in the central and peripheral nervous system and the gastrointestinal tract (Dhaliwal and Gupta, Physiology, Opioid Receptor. [Updated 2021 Jul. 26]. In: StatPearls [Internet]. Treasure Island (FL): StatPearls Publishing; 2021 January Available at nobi.nimnnih.gov/books/NBK546642/ on the world wide web. Opioids comprise natural opioids (such as, morphine, codeine, and thebaine) and synthetic opioids (such as, hydromorphone, oxymorphone, hydrocodone, oxycodone, remifentanil, sufentanil and fentanyl). Additional opioid includes Alfentanil, Demerol, buprenorphine, and Nubian.

The term "opioid-free" refers to a composition, method and/or system configured to achieve a stated effect without the need of opioids. Accordingly, the term "opioid-free" as used herein with respect to anesthetic compositions, methods and/or system, refers to compositions, methods and/or system, configured to induce and/or maintain analgesia and/or anesthesia without need of comprising, administering and/or in general of using, opioids.

The term "opioid-free treatment period" refers to a period of time of an opioid-free treatment encompassing at-home, pre-operatively, intra-operatively and post-operatively in recovery, in the hospital and/or at home during recovery.

The abbreviation "OFA" refers to opioid-free anesthesia It is synonymous with preemptive non-opioid analgesia.

The abbreviation "Non-OFA" refers to non-opioid-free anesthesia.

The term "preemptive non-opioid analgesia" or "preemptive non-opioid anesthesia" refers to a composition or a related method that has antinociceptive effect on a patient that prevents establishment of an altered process of afferent input which amplifies postoperative pain (Gottschalk and Smith, *Am. Fam. Physician.* 2001 May 15; 63(10):1979-1985). Preemptive non-opioid analgesia prevents the establishment of central and peripheral sensitization caused by incisional and inflammatory injuries that occurs in the intra-operative and post-operative stages of a medical or surgical procedure. Preemptive non-opioid analgesia is used interchangeably with OFA.

The term "central sensitization" refers to the development and maintenance of persistent postinjury chronic pain, such as post-surgery changes in the central nervous system that result in pain hypersensitivity (Latremoliere, A., & Woolf, C. J., *J.* Pain Res., (2009) 10(9), 895-926).

The term "anesthesia," is defined as loss of noxious sensation with or without loss of consciousness. Anesthesia includes general anesthesia (GA), sedation, and regional and local anesthesia. Anesthesia is used for medical purposes. Anesthesia enables the painless performance of medical procedures that would otherwise cause severe or intolerable pain to an unanesthetized patient or would otherwise be technically unfeasible. Therefore, anesthesia is typically induced by blocking nociception which refers to a sensory nervous system's response to mechanical (e.g., cutting, crushing) stimulation of sensory nerve cells called nociceptors which produces a pain signal that travels along a chain of nerve fibers via the spinal cord to the brain. Anesthesia can result in a patient being completely or partially awake (MAC (Monitored Anesthesia Care), neuraxial anesthesia (spinal/epidural) and regional anesthesia (Bier block/never block)) as will be understood by a skilled person.

The term "general anesthesia" or "GA" is a state in which the central nervous system activity is suppressed, resulting in unconsciousness and total lack of sensation. General anesthesia can be induced by intravenous administration, inhalation and/or intramuscular administration of suitable drugs such as, ketamine or a combination of ketamine and other agents as understood by a skilled person.

The term "sedation" refers to the administration of anxiolysis agents, pain mediating agents, and a wide spectrum of sedation from minimal to inducing an unresponsive state to facilitate a medical procedure or diagnostic procedure. Monitored anesthesia care (MAC) is characterized by a varying degree of depressed consciousness such that the patient is able to continuously and independently maintain a patient airway, retain protective reflexes, and remain responsive to verbal cues and/or tactile or physical stimulation. Exemplary sedative drugs that can be used in human and veterinary applications for MAC or induction and/or maintenance of general anesthesia (GA) include propofol, etomidate, ketamine, pentobarbital, Bristol (methohexital), lorazepam, midazolam, isoflurane, sevoflurane, desflurane, and dexmedetomidine.

The terms "regional anesthesia" and "local anesthesia" refer to a state in which transmission of nerve impulses is blocked from a specific part of the body. Depending on the situation, local or regional anesthesia may be used either on their own (in which case the patient remains fully conscious), or in combination with general anesthesia or sedation. Local anesthetic nerve block or local block as used herein refers to pain relief by blocking the transmission of pain signals from the surgical site via targeted perineural local anesthesia injection/infusion. In local anesthesia the area of interest is typically infiltrated with local anesthesia and no sedation or IV medications are typically involved (unless required by the condition of the patient) as will be understood by a skilled person. If sedation is desired or required, a local/MAC (Monitored Anesthesia Care) is specified. Not all local anesthetic agents can be administered intravenously due to cardiotoxic effects associated with local anesthetic systemic toxicity (LAST) leading to cardiac arrest as will also be understood by a skilled person The terms "anesthesiology" "anesthetic," and the like refer herein to compounds, compositions, processes or procedures that induce insensitivity to pain by temporary loss of sensation. A patient under the effects of anesthetic drugs is referred to as being anesthetized.

The term "Aldrete score" refers to a patient's score on the "Aldrete's scoring system". The term "Aldrete scoring system" is a commonly used scale for determining when a patient can be safely discharged from the post-anesthesia care unit (PACU) to either the postsurgical ward or another recovery area. Factors that affect a patient's Aldrete score include the patient's activity, respiration, blood pressure, consciousness, and color.

The term "medical or surgical procedure" generally refers to a procedure that requires anesthesia, sedation, or analgesia. In some contexts, a medical or surgical procedure encompasses the administration of anesthesia, sedation, or analgesia in a setting outside of a hospital or surgical site, such as hospice. In other contexts, a medical or surgical procedure refers to a procedure that requires the anesthesia, sedation or analgesia and that practices operative manual and instrumental techniques on an individual to investigate or treat a pathological condition, such as, a disease or injury, to help improve bodily function or appearance or to repair unwanted ruptured areas. In particular, the term "medical or surgical procedure" comprises both an operation and reoperation wherein the term "reoperation" refers to a second or subsequent surgery following an initial surgery to re-address an aspect of patient care that is best treated surgically. Reasons for reoperation include persistent bleeding after surgery, development of or persistence of infection.

The term "pre-operative" refers to a phase of a medical or surgical procedure that includes the establishment of a patient's baseline assessment in the clinical setting or at home, carrying out pre-operative interview or preparing the patient for the anesthetic.

The term "intra-operative" refers to a phase of a medical or surgical procedure that includes a period from time of surgical beginning to time of surgical ending. In particular, the term "intra-operative" indicates the time that the patient goes into the operating room until the time the patient leaves the operating room. Inclusive in this time is induction of anesthesia/placement of spinal, application of surgical dressings and/or casting as will be understood by a skilled person. Intra-operative is commonly interchangeable with an indication that the patient is "in surgery" or if the surgery is in progress that the patient is "having surgery" as would also be understood by a skilled person.

The term "post-operative" or "post-operation" refers to a phase following a medical or surgical procedure beginning at the end of the surgery and ending at the time of discharge from a medical facility. A post-operative phase typically encompasses from when a patient is transferred to a recovery room, post-anesthesia care unit (PACU) or intensive care unit (ICU), until the patient is discharged from the medical facility, or until completion of a follow-up care. During this phase the patient may be administered a post-operative composition as part of the post-operative pain management plan of care.

The abbreviation "PACU" refers to post-anesthesia care unit.

The abbreviation "POH" refers to preoperative hold.

The term "induction" or "induce" refers to the attainment of a state of unconsciousness of a patient by administration of a composition as described herein. Exemplary intravenous induction composition includes a composition containing at least one of propofol, sodium thiopental, etomidate, methohexital, and ketamine or combinations thereof.

The term "maintains" or "maintenance" refers to the sustenance of a state of unconsciousness of a patient by administration of a pharmaceutical composition or agent after induction. Exemplary maintenance composition includes a mixture of oxygen, sometimes nitrous oxide, and a volatile anesthetic agent and/or a composition for Intra Venous (IV) administration as disclosed herein.

The term "magnesium salt" or "$Mg^{2+}$ salt" refers to a salt of the magnesium ion ($Mg^{2+}$) with a pharmaceutically acceptable counterion and solvates and hydrates thereof.

The term "pharmaceutically acceptable counterion" includes, for example, acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycinate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate, threonate, or tosylate and hydrates and solvates thereof, as well as additional counterions identifiable by a skilled person upon reading the disclosure.

The term "alpha-2 agonist" refers to an agent that stimulates the action of the alpha-2-adrenergic receptor. Alpha-2-adrenergic receptors are located on pre-junctional terminals in the central nervous system where they inhibit the release of norepinephrine in the form of negative feedback. They are further located postsynaptically on the vascular smooth muscle cells of certain blood vessels, such as those found in skin arterioles or on veins. The alpha-2-adrenergic receptors bind both norepinephrine released by the sympathetic postganglionic fibers and epinephrine released by the adrenal medulla. Common effects of alpha-2-adrenergic receptors include suppression of release of norepinephrine by negative feedback, transient hypertension followed by sustained hypotension, decrease in heart rate, vasoconstriction of certain arteries, venoconstriction of some veins, decrease of motility of smooth muscles in the gastrointestinal tract, and sedation and analgesia. Exemplary alpha-2 agonists include dexmedetomidine, clonidine, fadolmidine, guanabenz, guanoxabenz, guanethidine, xylazine, tizanidine, medetomidine, methyldopa, methylnorepinephrine, (R)-3-nitrobiphenyline, amitraz, detomidine, lofexidine, and medetomidine. For human applications, exemplary alpha-2 agonists include dexmedetomidine, clonidine, methyldopa, and norepinephrine.

The term "sodium channel inhibitor" refers to an agent that blocks the conduction of sodium ions ($Na^{+}$) through sodium channels. As used herein, the term "sodium channel inhibitor" is intended to be synonymous with "sodium channel blocker." Exemplary sodium channel inhibitors include quinidine, ajmaline, procainamide, disopyramide, lidocaine, procaine, prilocaine, phenytoin, mexiletine, tocainide, encainide, flecainide, propafenone and moricizine. For human applications, exemplary sodium channel inhibitors include procainamide, lidocaine, procaine, prilocaine, and flecainide.

The term "NMDA antagonist" refers to an agent that blocks or antagonizes the action of N-Methyl-D-aspartate receptor. Exemplary NMDA antagonists include ketamine, magnesium salts (such as, magnesium sulfate), dextromethorphan (DXM), phencyclidine (PCP), methoxetamine (MXE), and nitrous oxide ($N_2O$). For human applications, exemplary NMDA antagonists include ketamine, magnesium salts (such as, magnesium sulfate), and nitrous oxide ($N_2O$).

The term "beta-blocker" refers to an agent that blocks the receptor sites for the endogenous catecholamines epinephrine (adrenaline) and norepinephrine (noradrenaline) on beta adrenergic receptors, of the sympathetic nervous system. Exemplary beta blockers include carvedilol, propranolol, esmolol, timolol, metoprolol, labetalol, atenolol, bisoprolol and nebivolol. For human applications, exemplary beta-blockers include propranolol, esmolol, metoprolol, and labetalol.

The term "corticoid" or "corticosteroid" refers to any natural steroid hormones produced in the adrenal cortex of vertebrates, as well as the synthetic analogues of those natural steroid hormones. Exemplary corticosteroids include cortisone, hydrocortisone, fludrocortisone acetate, prednisolone, prednisone, methylprednisolone, triamcinolone, Dexamethasone Sodium phosphate (Dexamethasone), betamethasone, triamcinolone acetonide, and fluorometholone. Glucocorticosteroids inhibit prostaglandin, bradykinin, histamine and leukotrienes production thereby decreasing inflammation.

The term "agent" refers to an ingredient of a pharmaceutical composition that is biologically active. The qualifier of the term "agent" indicates the related biological activity, typically performed by interaction of the agent with one or more molecular targets in the individual. In contrast with the active ingredients, the inactive ingredients are usually called excipients in pharmaceutical contexts. The main excipient that serves as a medium for conveying the active ingredient is usually called the vehicle. Saline, sterile water, petrolatum and mineral oil are common vehicles as will be understood by a skilled person.

The term "calcium channel inhibitor" refers to an agent that blocks the conduction of calcium ions ($Ca^{2+}$) through calcium channels. As used herein, the term "calcium channel inhibitor" is intended to be synonymous with "calcium channel blocker". Exemplary calcium channel inhibitors include verapamil, diltiazem, nifedipine, nimodipine, nicardipine, flunarizine, and cinnarizine.

The term "Cox inhibitor" refers to a type of nonsteroidal anti-inflammatory drug. Exemplary Cox inhibitors include celecoxib, etodolac, etoricoxib, valdecoxib, parecoxib, aspirin, diflunisal, ibuprofen, dexibuprofen, naproxen, fenoprofen, ketoprofen, indomethacin, tolmetin, diclofenac, sulindac, ketorolac, piroxicam, meloxicam, tenoxicam, droxicam, mefenanmic acid, meclofenanmic acid, clonixin, licofelone, and paracetamol (acetaminophen). For human applications, exemplary Cox inhibitors include celecoxib, etodolac, aspirin, ibuprofen, naproxen, ketoprofen, indomethacin, diclofenac, ketorolac, meloxicam, tenoxicam, and paracetamol (acetaminophen).

The term "non-steroid anti-inflammatory drug" or "NSAID" refers to a class of compounds that are free of any steroid moieties yet are capable of providing analgesic, antipyretic and/or anti-inflammatory effects. Exemplary NSAIDs include Celecoxib, refecoxib (commonly known as vioxx), etoricoxib, valdecoxib, parecoxib, aspirin, diflunisal, ibuprofen, dexibuprofen, naproxen, fenoprofen, ketoprofen, indomethacin, tolmetin, diclofenac, sulindac, etodolac, ketorolac, piroxicam, meloxicam, tenoxicam, droxicam, mefenanmic acid, meclofenanmic acid, clonixin, and licofelone. NSAIDs that can be used in combination with opioid-free composition methods and systems of the present disclosure can be identified by a skilled person in view of the properties of the NSAID, the properties of the agents used in the opioid-free compositions methods and systems of the disclosure and any additional indications provided in the present disclosure.

The term "GABA analogue" refers to an agent that binds to a GABA receptor resulting in a negative change in the transmembrane potential of a cell, usually causing hyperpolarization. There are two classes of GABA receptors: $GABA_A$ and $GABA_B$. $GABA_A$ receptors are ligand-gated ion channels (also known as ionotropic receptors); whereas $GABA_B$ receptors are G protein-coupled receptors, also called metabotropic receptors. Exemplary GABA analogue includes pregabalin, gabapentin, picamilon and progabide. For human applications, exemplary GABA analogue includes pregabalin, and gabapentin.

The term "antidepressant" refers to an agent that corrects chemical imbalances of neurotransmitters in the central nervous system and is capable of relieving symptoms of depression, social anxiety disorder, anxiety disorders, seasonal affective disorder, and dysthymia, or mild chronic depression. Antidepressant as used herein can alleviate pain and can be used for prevention and treatment of chronic pain or acute pain.

The term "antiemetic" refers to a drug or medicament that treats, reduces, and/or prevents nausea and/or vomiting. Exemplary antiemetic agent includes ondansetron, dolasetron, granisetron, palonosetron, promethazine, metoclopramide, imenhydrinate, and droperidol. For human applications, exemplary antiemetic agent includes ondansetron, dolasetron, granisetron, promethazine, metoclopramide, and droperidol.

The term "pharmaceutical composition" refers to a mixture or combination of two or more chemical or biological compounds or substances with an pharmaceutically acceptable excipient that is intended for use. The pharmaceutical composition of the disclosure can be intended for use in anesthesia applications.

The term "effective amount" or "therapeutically effective amount" refers to the amount of the compound or pharmaceutical composition that will elicit the biological or medical response of a tissue, system, animal or human that is being sought by the researcher, medical provider or other clinician.

The term pharmaceutically acceptable "vehicle" refers to any of various media used as a solvent, carrier, binder or diluent for delivery of a therapeutic active ingredient(s) in a pharmaceutical composition. Typically, a vehicle can be an excipient preferably for improving the efficiency of delivery and the effectiveness of a pharmaceutical composition. Preferred vehicle used in opioid-free compositions of the present disclosure comprise a saline solution, sterile water and additional vehicle identifiable by a skilled person upon reading of the present disclosure.

The term pharmaceutically acceptable "carrier" refers to a non-toxic carrier that may be administered to a patient, together with a therapeutic active ingredient(s), and which does not destroy the pharmacological activity thereof.

The term pharmaceutically acceptable "excipient" refers to a pharmacologically inactive substance that is formulated in combination with the pharmacologically active ingredient of pharmaceutical composition and is inclusive of bulking agents, fillers, diluents and products used for facilitating drug absorption, aiding manufacturing, enhancing drug delivery or targeting, improving stability, handling, or solubility, or for other pharmacokinetic considerations. Pharmaceutically acceptable excipients are known in the pharmaceutical arts and are disclosed, for example, in Gennaro, Ed., Remington: *The Science and Practice of Pharmacy,* $20^{th}$ Ed. (Lippincott, Williams & Wilkins, Baltimore, Md. 2000); *Handbook of Pharmaceutical Excipients*, American Pharmaceutical Association, Washington, D.C. (e.g., $1^{st}$, $2^{nd}$, and $3^{rd}$ Eds., 1986, 1994, and 2000, respectively); and Pramanick et al., *Pharma Times,* 45(3), March 2013, 65-77. Pharmaceutically acceptable excipients include bulking agents, buffering agents, tonicity adjusting agents, preservatives, antioxidants, antimicrobial agents, chelating agents, solubilizing agents, complexing and dispersing agents, flocculating/suspending agents, wetting agents, and solvent systems.

The term "treatment" refers to any activity that is part of a medical care for, or deals with, a condition, medically or surgically. For example, as used herein a treatment as used herein include administration of an opioid-free anesthetic composition to an individual to achieve a predetermined state of sedation and analgesia.

The term "individual" or "patient" as used herein, refers to an animal, particularly a mammal, and more particularly a human being.

The term "ideal body weight" or "IBW" refers to the appropriate healthy weight in relation to height. Typically determination of IBW is based on the following equations for individuals who are human beings:

$$\text{IBW (kg)}=50.0+[2.3\times(\text{Height in inches}-60)] \text{ for men, and}$$

$$\text{IBW (kg)}=45.5+[2.3\times(\text{Height in inches}-60)] \text{ for women.}$$

Additionally, calculators are available allowing one of skills to identify the correct IBW such as calculator.net/ideal-weight-calculator.html on the world wide web. In particular, a skilled person would understand that there is no "gold standard" for calculating IBW, there are multiple charts and calculators that can vary significantly depending on the norms of the country of origin.

The term "adjusted body weight" or "AdjBW" refers to calculation adjustments made to a body weight measurement and is applicable to subjects with amputations, oedema, ascites, and chronic kidney disease, as well as in obesity.

Unless otherwise specifically indicated, the term "patient weight" refers to the ideal body weight of the patient. (Courtney M Peterson et al., "Universal equation for estimating ideal body weight and body weight at any BMI," Am. J. Clin. Nutr. 2016; 103:1197-203.)

The term "infusion" refers to intravenous administration of a liquid composition into the venous system through a needle or catheter to a patient in need of the composition.

The term "intramuscular route" refers to the administration of a composition into a muscle of a patient, typically using injections.

The term "numeric rating scale" or "NRS" refers to a measure of pain intensity on an 11-point scale (0 to 10) in which 0 means no pain, 1-3 means mild pain, 4-6 means moderate pain, and 7-10 means severe pain. (physio-pedia-.com/Numeric_Pain_Rating_Scale on the world wide web).

The term "anesthesia provider" refers to a nurse anesthesiologist, physician anesthesiologist, and anesthesiologist assistant who is supervised by a physician anesthesiologist.

It is also to be understood that the terminology used herein is for the purpose of describing particular embodiments only, and is not intended to be limiting. As used in the disclosure, the singular forms "a," "an," and "the" include plural referents unless the content clearly dictates otherwise. The term "plurality" includes two or more referents unless the content clearly dictates otherwise.

Full phrases or words for some abbreviations as used herein are indicated in the parenthesis: dex (dexmedetomidine), Lido (Lidocaine), sx (surgery), BID (twice a day), HS (at bedtime), PO (by mouth), Q8H (every 8 hours), Q12H (every 12 hours), D/C (discontinue), IV (intravenous), IVP (IV push), pt. (patient), PONV (postoperative nausea and vomiting), OSA (obstructive sleep apnea), TIVA (total intravenous anesthesia), w/w (concentration by weight percentage), End-tidal CO2 (ETCO2).

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

Unless defined otherwise, all technical and scientific terms used herein have the same meaning as commonly understood by one of ordinary skill in the art to which the disclosure pertains.

4.2 Opioid-Free Compositions

In one aspect, the disclosure provides opioid-free compositions having anesthetic properties. In particular, the opioid-free compositions of the disclosure are designed to eliminate or reduce opioids in compositions used to induce and/or maintain anesthesia and provide improved post-operative pain control. Opioid-free compositions of the disclosure can be used, in particular, during the pre-operative stage and/or during the intra-operative stage of a medical or surgical procedure to induce or maintain anesthesia in a patient. Advantageously, the opioid-free compositions of the disclosure can be administered to a patient in an opioid-free treatment without or with a reduction of the undesirable side effects associated with opioids, such as hyperalgesia, opioid tolerance, nausea, vomiting, shivering, respiratory depression, urinary retention, bradycardia, hypotension, and additional side effects identifiable by a skilled person.

In particular embodiments, the opioid-free compositions as described herein can be used for sedation cases as well as general anesthesia cases. Both uses result in improved post-operative pain relief as compared to an opioid-based anesthetic. In some embodiments, the improvement of post-operative pain relief as compared to opioid-based anesthetic results in a reduction of numeric pain intensity level by at least 1, 2, 3, 4 or 5 on a numeric rating scale ("NRS") as well as immediate post-operative opioid consumption.

Figure 1:
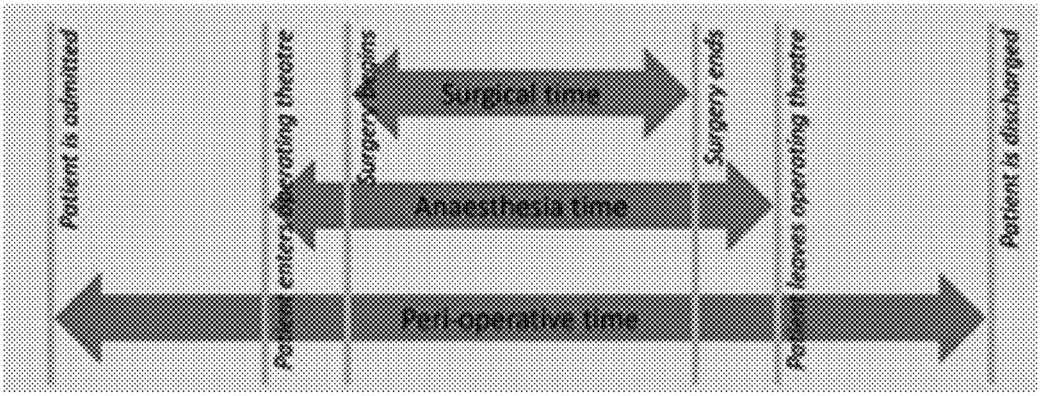

Reference is made to FIG. 1 providing a schematic illustration of the stages of a medical or surgical procedure. In FIG. 1, the intra-operative phase of the medical or surgical procedure is indicated as "surgical time" and the combination of the intra-operative phase and the post-operative stage is indicated as "anaesthesia time". Anaesthesia time begins with "operating theatre" and includes the pre-operative holding area and the Post-Anesthesia Care Unit (PACU)/recovery room. The POH is the location that the patient is typically administered the pre-operative loading dose as would be understood by a skilled person.

In one aspect, the disclosure provides opioid-free compositions comprising a magnesium salt, at least one alpha-2 agonist, and at least one sodium channel inhibitor and optionally at least one NMDA antagonist other than the magnesium salt, at least one beta-blocker and/or at least one corticoid.

In various embodiments of the opioid-free composition of the disclosure, the magnesium salt is a magnesium ion with a pharmaceutically acceptable counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycinate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate, threonate, or tosylate and hydrates and solvates thereof. The selection of a particular magnesium salt and any adjustments to concentration, dosages, compositions and timing of administration is within the skill of the art, particularly in view of the properties of the specific magnesium salt and the indications provided in the disclosure.

In particular embodiments, the magnesium salt comprises magnesium sulfate or magnesium chloride, or a magnesium salt functionally equivalent to magnesium sulfate or magnesium chloride. Magnesium salts functionally equivalent to magnesium sulfate and magnesium chloride are identifiable by a skilled person.

In various embodiments of the opioid-free composition of the disclosure, the at least one alpha-2 agonist is selected from the group consisting of dexmedetomidine, clonidine, fadolmidine, guanabenz, guanoxabenz, guanethidine, xylazine, tizanidine, medetomidine, methyldopa, methylnorepinephrine, (R)-3-nitrobiphenyline, amitraz, detomidine, lofexidine, and medetomidine or any combination thereof, as well as additional alpha-2 agonists identifiable by a skilled person upon reading of the disclosure. The selection of a particular alpha-2 agonist and any adjustments to concentration, dosages, compositions and timing of administration is within the skill of the art, particularly in view of the properties of the specific alpha-2 agonist and the indications provided in the disclosure.

For example, in some embodiments in which the opioid-free composition is to be administered to a human patient, the at least one alpha-2 agonist is selected from dexmedetomidine, clonidine, methyldopa, and norepinephrine or any combination thereof. In particular embodiments, the at least one alpha-2 agonist comprises dexmedetomidine. In other embodiments, the at least one alpha-2 agonist comprises clonidine. A skilled person would know that dexmedetomidine is quicker onset and offset than clonidine. Dexmedetomidine also has a higher degree of selectivity to alpha-2 receptors (1600:1 as compared to clonidine 220:1) resulting in more of the desired effects and less of the unwanted effects.

In particular embodiments, the at least one alpha-2 agonist comprises dexmedetomidine or an alpha-2 agonist functionally equivalent to dexmedetomidine.

In general, a skilled person would know that alpha-2 agonists have their desired effect by decreasing the sympathetic outflow of norepinephrine. Peripherally alpha-2 agonist blocks the conduction of C-fibers which are unmyelinated fibers that conduct slowly yet intense and persistent pain signals. Influences on inhibitory G coupled proteins produce peripheral analgesia. Activation of alpha-2 adrenoreceptors in the dorsal horn of the spinal cord is responsible for centrally acting analgesia. Inhibited release of substance P and norepinephrine is a result of activation of G-coupled alpha-2 adrenoreceptors. This activation inhibits adenyl cyclase, decreasing intracellular cyclic adenosine monophosphate. Supraspinal analgesia and sedation results from alpha-2 adrenoreceptor activation in the locus coeruleus. Accordingly, identification of a suitable alpha-2 agonist functionally equivalent to dexmedetomidine can be performed in view of the general properties of the alpha-2 agonists, the properties of the dexmedetomidine and of the indications provided in the present disclosure as will be understood by a skilled person.

In various embodiments of the opioid-free composition of the disclosure, the at least one sodium channel inhibitor is selected from the group consisting of bupivacaine, quinidine, ajmaline, procainamide, disopyramide, lidocaine, procaine, prilocaine, phenytoin, mexiletine, tocainide, encainide, flecainide, propafenone and moricizine and any combination thereof, as well as additional sodium channel inhibitors identifiable by a skilled person upon reading of the disclosure. The selection of a particular sodium channel inhibitor and any adjustments to concentration, dosages, compositions and timing of administration is within the skill of the art, particularly in view of the properties of the specific sodium channel inhibitor and the indications provided in the disclosure.

For example, in some embodiments in which the opioid-free composition is to be administered to a human patient, the at least one sodium channel inhibitor is selected from procainamide, lidocaine, procaine, prilocaine, and flecainide or any combination thereof. In particular embodiments, the at least one sodium channel inhibitor comprises lidocaine, procaine, or any combination thereof.

In other embodiments, the sodium channel inhibitor comprises lidocaine or a sodium channel inhibitor functionally equivalent to lidocaine. Sodium channel inhibitors functionally equivalent to lidocaine are identifiable by a skilled person.

When present in the opioid-free composition of the disclosure, the at least one NMDA antagonist is selected from the group consisting of ketamine, a magnesium salt, dextromethorphan (DXM), phencyclidine (PCP), methoxetamine (MXE), and nitrous oxide ($N_2O$) and any combination thereof, as well as additional NMDA antagonists identifiable by a skilled person upon reading of the disclosure. The selection of a particular NMDA antagonist and any adjustments to concentration, dosages, compositions and timing of administration is within the skill of the art, particularly in view of the properties of the specific NMDA antagonist and the indications provided in the disclosure.

For example, in some embodiments in which the opioid-free composition is to be administered to a human patient, the at least one NMDA antagonist is selected from ketamine, magnesium salts (such as, magnesium sulfate), and nitrous oxide ($N_2O$) or any combination thereof. In particular embodiments, the at least one NMDA antagonist comprises ketamine or an NMDA antagonist functionally equivalent to ketamine. NMDA antagonists functionally equivalent to ketamine are identifiable by a skilled person. In various embodiments, the at least one NMDA antagonist comprises ketamine.

When present in the opioid-free composition of the disclosure, the at least one beta-blocker is selected from the group consisting of carvedilol, esmolol, propranolol, timolol, metoprolol, labetalol, atenolol, bisoprolol and nebivolol and any combination thereof, as well as additional beta-blockers identifiable by a skilled person upon reading of the disclosure. The selection of a particular beta-blocker and any adjustments to concentration, dosages, compositions and timing of administration is within the skill of the art, particularly in view of the properties of the specific beta-blocker and the indications provided in the disclosure.

For example, in some embodiments in which the opioid-free composition is to be administered to a human patient, the at least one beta-blocker is selected from propranolol, esmolol, metoprolol, and labetalol or any combination thereof. In particular embodiments, the at least one beta-blocker comprises esmolol or a beta-blocker functionally equivalent to esmolol. Beta-blockers functionally equivalent to esmolol are identifiable by a skilled person. In various embodiments, the at least one beta blocker comprises esmolol.

When present in the opioid-free composition of the disclosure, the at least one corticosteroid is selected from the group consisting of dexamethasone sodium phosphate (Dexamethasone), cortisone, hydrocortisone, fludrocortisone acetate, prednisolone, prednisone, methylprednisolone, triamcinolone, betamethasone, triamcinolone acetonide, and fluorometholone and any combination thereof, as well as additional corticosteroids identifiable by a skilled person upon reading of the disclosure. The selection of a particular corticosteroid and any adjustments to concentration, dosages, compositions and timing of administration is within the skill of the art, particularly in view of the properties of the specific corticosteroid and the indications provided in the disclosure.

In particular embodiments, the at least one corticosteroid comprises dexamethasone sodium phosphate (Dexamethasone) or a corticosteroid functionally equivalent to Dexamethasone. Corticosteroids functionally equivalent to Dexamethasone are identifiable by a skilled person. In some aspects of this embodiment, the corticosteroid comprises dexamethasone sodium phosphate (Dexamethasone), a corticosteroid belonging to the class of glucocorticosteroids and can be classified even more broadly as steroids, as will be understood by a skilled person. In particular embodiments, the at least one corticosteroid comprises Dexamethasone.

In various embodiments, the opioid-free compositions of the disclosure can also be used in combination with additional agents. Suitable additional agents include sodium channel inhibitors, calcium channel inhibitors, Cox-1 or Cox-2 enzyme inhibitors (or Cox inhibitors), acetaminophen, GABA receptor agonists including $GABA_A$ and $GABA_B$ receptors agonist (GABA mimetic or analogue), antidepressants, antiemetics, Cannabinoids (CBD), neurotransmitters, and/or non-steroid anti-inflammatory drugs (NSAIDs).

When used in combination with the opioid-free composition of the disclosure, the calcium channel inhibitor is selected from the group consisting of verapamil, diltiazem, nifedipine, nimodipine, nicardipine, flunarizine and cinnarizine and any combination thereof, as well as additional calcium channel inhibitors identifiable by a skilled person upon reading of the disclosure. The selection of a particular calcium channel inhibitor and any adjustments to concentration, dosages, compositions and timing of administration is within the skill of the art, particularly in view of the properties of the specific calcium channel inhibitor and the indications provided in the disclosure.

For example, in some embodiments in which the opioid-free composition is to be administered to a human patient, the calcium channel inhibitor is selected from celecoxib, etodolac, aspirin, ibuprofen, naproxen, ketoprofen, indomethacin, diclofenac, ketorolac, meloxicam, tenoxicam, and paracetamol (acetaminophen) or any combination thereof. In particular embodiments, the calcium channel inhibitor comprises verapamil and/or diltiazem.

When used in combination with the opioid-free composition of the disclosure, the GABA analogue is selected from the group consisting of pregabalin, gabapentin, picamilon and progabide and any combination thereof, as well as additional GABA analogues identifiable by a skilled person upon reading of the disclosure. The selection of a particular GABA analogue and any adjustments to concentration, dosages, compositions and timing of administration is within the skill of the art, particularly in view of the properties of the specific GABA analogue and the indications provided in the disclosure.

In particular embodiments, the GABA analogue is Lyrica® (pregabalin) or Neurontin (gabapentin) or combinations thereof.

When used in combination with the opioid-free composition of the disclosure, the antidepressant is selected from serotonin and noradrenaline reuptake inhibitors (SNRIs), selective serotonin reuptake inhibitors (SSRIs), tricyclic antidepressants (TCAs), tetracyclic antidepressants (TeCA), monoamine oxidase inhibitors (MAOIs), and noradrenaline and specific serotoninergic antidepressants (NASSAs). Exemplary serotonin and noradrenaline reuptake inhibitors (SNRIs) include Venlafaxine, Cymbalta (Duloxetine), Venlafaxine XR, Venlafaxine ER, Desvenlafaxine, and Venlafaxine. Exemplary selective serotonin reuptake inhibitors (SSRIs) include Sertraline, Citalopram, Fluoxetine, Escitalopram, Paroxetine. Exemplary tricyclic antidepressants (TCAs) include Amitriptyline, and Nortriptyline. Exemplary tetracyclic antidepressants (TeCA) include Mirtazapine. Exemplary monoamine oxidase inhibitors (MAOIs) include phenelzine (Nardil), tranylcypromine (Parnate), isocarboxazid (Marplan) and selegiline (EMSAM, Eldepryl). Exemplary noradrenaline and specific serotoninergic antidepressants (NASSAs) include Mianserin (Tolvon) and Mirtazapine (Remeron, Avanza, Zispin). The selection of a particular antidepressant and any adjustments to concentration, dosages, compositions and timing of administration is within the skill of the art, particularly in view of the properties of the specific antidepressant and the indications provided in the disclosure.

In particular embodiments, the antidepressant comprises a serotonin and noradrenaline reuptake inhibitor (SNRIs) selected from the group consisting of Venlafaxine, Cymbalta (Duloxetine), Venlafaxine XR, Venlafaxine ER, Desvenlafaxine, and Venlafaxine.

When used in combination with the opioid-free composition of the disclosure, the antiemetic agent is selected from the group consisting of includes ondansetron, dolasetron, granisetron, palonosetron, promethazine, imenhydrinate, metoclopramide, meclizine, droperidol, haloperidol and any combination thereof, as well as additional antiemetic agents identifiable by a skilled person upon reading of the disclosure. The selection of a particular antiemetic agent and any adjustments to concentration, dosages, compositions and timing of administration is within the skill of the art, particularly in view of the properties of the specific antiemetic agent and the indications provided in the disclosure.

For example, in some embodiments in which the opioid-free composition is to be administered to a human patient, the antiemetic agent is selected from ondansetron, dolasetron, granisetron, palonosetron, promethazine, metoclopramide, meclizine, droperidol or any combination thereof.

The opioid-free composition of the disclosure are typically in form of pharmaceutical compositions in which the active agents are present in a therapeutically effective amount together with a pharmaceutically acceptable vehicle, carrier or excipient.

The opioid-free compositions of the disclosure encompass pre-operative compositions, intra-operative compositions, peri-operative compositions, and post-operative compositions. It is contemplated that the opioid-free compositions can be used in the operating room, hospice, procedural settings (i.e., those settings in which medical procedures are performed outside the operating room and in other settings known to those of skill in the art.

4.2.1 Opioid-Free Pre-Operative Compositions

In one embodiment, the disclosure provides an opioid-free pre-operative composition. The opioid-free pre-operative composition comprises:

- a magnesium ($Mg^{2+}$) salt,
- an alpha-2 agonist, and optionally

- a sodium channel inhibitor, and/or
- a N-methyl-D-aspartate receptor (NMDA) inhibitor, and/or
- a corticosteroid, together with a pharmaceutically acceptable vehicle, carrier, or excipient, in an effective amount for treating anxiety and/or inducing sedation, and/or analgesia of the individual in any phase of the pre-operative methods of the disclosure.

The particular magnesium salt, alpha-2 agonist, sodium channel inhibitor, NDMA inhibitor and corticosteroid present in the opioid-free pre-operative composition are selected from those disclosed above in connection with the opioid-free composition in Section 4.2. The amount of each component present in the pre-operative composition of the disclosure is an amount effective for treating anxiety and/or inducing sedation, and/or analgesia in a pre-operative methods of the disclosure.

In some embodiments, the opioid pre-operative composition further comprises an additional agent selected from the group consisting of a calcium channel inhibitor, CBD, a Cox inhibitor, a GABA analogue, an antidepressant, acetaminophen, antiemetic agent or any combination thereof. These additional agents are described above in connection with the opioid-free composition in Section 4.2.

In some embodiments, the magnesium salt is present in the opioid-free pre-operative composition in an amount ranging from about 1 mg/mL to about 500 mg/mL, about 2 mg/mL to about 300 mg/mL, about 3 mg/mL to about 300 mg/mL, about 4 mg/mL to about 300 mg/mL, about 5 mg/mL to about 300 mg/mL, about 50 mg/mL to about 300 mg/mL, or about 100 mg/mL to about 300 mg/mL. In particular embodiments, the magnesium salt is present in the opioid-free pre-operative composition in an amount of about 1 mg/mL, about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, about 400 mg/mL, about 410 mg/mL, about 420 mg/mL, about 430 mg/mL, about 440 mg/mL, about 450 mg/mL, about 460 mg/mL, about 470 mg/mL, about 480 mg/mL, about 490 mg/mL, or about 500 mg/mL.

In various embodiments, the magnesium salt comprises magnesium sulfate or a magnesium salt functionally equivalent thereof.

In some embodiments, the alpha-2 agonist is present in the opioid-free pre-operative composition in an amount ranging from about 0.001 mcg/mL to about 50 mcg/mL, 0.01 mcg/mL to about 50 mcg/mL, about 0.1 mcg/mL to about 40 mcg/mL, about 0.2 mcg/mL to about 30 mcg/mL, about 0.3 mcg/mL to about 20 mcg/mL, 0.4 mcg/mL to about 15 mcg/mL, about 0.5 mcg/mL to about 10 mcg/mL, about 1 mcg/mL to about 10 mcg/mL, about 2 mcg/mL to about 10 mcg/mL, or about 3 mcg/mL to about 10 mcg/mL. In particular embodiments, the one alpha-2 agonist is present in the opioid-free pre-operative composition in an amount of about 0.1 mcg/mL, about 0.2 mcg/mL, about 0.3 mcg/mL, about 0.4 mcg/mL, about 0.5 mcg/mL, about 0.6 mcg/mL, about 0.7 mcg/mL, about 0.8 mcg/mL, about 0.9 mcg/mL, about 1 mcg/mL, about 1.5 mcg/mL, about 2 mcg/mL, about 2.5 mcg/mL, about 3 mcg/mL, about 3.5 mcg/mL, about 4 mcg/mL, about 4.5 mcg/mL, about 5 mcg/mL, about 5.5 mcg/mL, about 6 mcg/mL, about 6.5 mcg/mL, about 7 mcg/mL, about 7.5 mcg/mL, about 8 mcg/mL, about 8.5 mcg/mL, about 9 mcg/mL, about 9.5 mcg/mL, about 10 mcg/mL, about 10.5 mcg/mL, about 11 mcg/mL, about 11.5 mcg/mL, about 12 mcg/mL, about 12.5 mcg/mL, about 13 mcg/mL, about 13.5 mcg/mL, about 14 mcg/mL, about 14.5 mcg/mL, or about 15 mcg/mL.

In various embodiments, the alpha-2 agonist comprises dexmedetomidine or an alpha-2 agonist functionally equivalent thereto.

In some embodiments, the sodium channel inhibitor is present in the opioid-free pre-operative composition in an amount ranging from about 0 mg/mL to about 40 mg/mL, about 0.01 mg/mL to about 36 mg/m, about 2.5 mg/mL to about 30 mg/mL, about 4 mg/mL to about 25 mg/mL, or about 10 mg/mL to about 20 mg/mL. In various embodiments, the sodium channel inhibitor is present in the opioid-free pre-operative composition in an amount ranging from about 1 mg/mL to about 10 mg/mL, about 2 mg/mL to about 8 mg/mL, about 3 mg/mL to about 7 mg/mL, or about 4 mg/mL to about 6 mg/mL. In particular embodiments, the sodium channel inhibitor is present in the opioid-free pre-operative composition in an amount of about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, about 15 mg/mL, about 15.5 mg/mL, about 16 mg/mL, about 16.5 mg/mL, about 17 mg/mL, about 17.5 mg/mL, about 18 mg/mL, about 18.5 mg/mL, about 19 mg/mL, about 19.5 mg/mL, or about 20 mg/mL.

In various embodiments, the sodium channel inhibitor comprises lidocaine or a sodium channel inhibitor functionally equivalent thereto.

In some embodiments, the at least one NMDA antagonist other than a magnesium salt is present in the opioid-free pre-operative composition in an amount ranging from about 0 mg/mL to about 35 mg/mL, about 0.01 mg/mL to about 30 mg/mL, about 1 mg/mL to about 25 mg/mL, about 1.5 mg/mL to about 20 mg/ml, about 2 mg/mL to about 15 mg/mL, about 2.5 mg/mL to about 10 mg/mL, or about 3 mg/mL to about 5 mg/mL. In various embodiments, the at least one NMDA antagonist other than a magnesium salt is present in the opioid-free pre-operative composition in an amount of about 0.5 mg/mL, about 1 mg/mL, about 1.5 mg/mL, about 2 mg/mL, about 3.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, or about 10 mg/mL.

In particular embodiments, the NMDA antagonist other than a magnesium salt present in the opioid-free pre-operative composition comprises ketamine, or an NMDA antagonist functionally equivalent thereto.

In some embodiments, the corticosteroid is present in the opioid-free pre-operative composition in amount ranging from about 0 mg/mL to about 10 mg/mL, about 0.2 mg/mL to about 9 mg/mL, about 0.4 mg/mL to about 8 mg/mL, about 0.6 mg/mL to about 7 mg/mL, about 0.8 mg/mL to about 6 mg/mL, about 1 mg/mL to about 5 mg/mL, or about 1.5 mg/mL to about 4 mg/mL. In some embodiments, the corticosteroid is present in the opioid-free pre-operative composition in amount ranging from about 0.1 mg/mL to about 5 mg/mL, about 0.15 mg/mL to about 4 mg/mL, from about 0.2 mg/mL to about 3 mg/mL to about 0.25 to about 2 mg/mL, about 0.3 mg/mL to about 1 mg/mL. In various embodiments, the corticosteroid is present in the opioid-free pre-operative composition in amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, or about 2 mg/mL.

In various embodiments, the corticosteroid present in the opioid-free pre-operative composition comprises Dexamethasone or a corticosteroid functionally equivalent thereto.

In one embodiments, the opioid-free pre-operative pharmaceutical composition comprises

- a magnesium salt at a concentration ranging from about 1 mg/mL to about 500 mg/mL;
- an alpha-2 agonist at a concentration ranging from about 0.001 to about 50 mcg/mL;
- a sodium channel inhibitor at a concentration ranging from about 0 mg/mL to about 40 mg/mL;
- an NMDA antagonist other than a magnesium salt at a concentration ranging from about 0 mg/mL to about 35 mg/mL; and
- a corticosteroid at a concentration ranging from about 0 mg/ml to about 10 mg/mL; together with pharmaceutically acceptable vehicle, carrier, or excipient.

In another embodiment, the opioid-free pre-operative pharmaceutical composition comprises

- a magnesium salt at a concentration ranging from about 50 mg/mL to about 300 mg/mL;
- an alpha-2 agonist at a concentration ranging from about 1 mcg/mL to about 10 mcg/mL;
- a sodium channel inhibitor at a concentration ranging from about 1 mg/mL to about 10 mg/mL;
- an NMDA antagonist other than a magnesium salt at a concentration ranging from about 3 mg/mL to about 5 mg/mL; and
- a corticosteroid at a concentration ranging from about 0.1 mg/ml to about 5 mg/mL,
- together with a pharmaceutically acceptable vehicle, carrier, or excipient.

In each of the embodiments described in the preceding two paragraphs, the magnesium salt comprises magnesium sulfate or a magnesium salt functionally equivalent thereto; the alpha-2 agonist comprises dexmedetomidine or an alpha-2 agonist functionally equivalent thereto; the sodium channel inhibitor comprises lidocaine or a sodium channel inhibitor functionally equivalent thereto; the NMDA antagonist other than a magnesium salt, when present, comprises ketamine, or an NMDA antagonist functionally equivalent thereto; and the corticosteroid, when present, comprises Dexamethasone or a corticosteroid functionally equivalent thereto.

In various embodiments, the opioid-free pre-operative composition is in a bolus formulation.

4.2.2 Opioid-Free Intra-Operative Compositions

In one embodiment, the disclosure provides an opioid-free intra-operative composition. The opioid-free intra-operative composition comprises:

- a magnesium salt,
- an alpha-2 agonist,
- a sodium channel inhibitor, and optionally

- an NMDA antagonist other than the magnesium salt, and/or
- a beta-blocker, together with a pharmaceutically acceptable vehicle, carrier, or excipient.

The particular magnesium salt, alpha-2 agonist, and sodium channel inhibitor, and optionally the NDMA inhibitor and beta-blocker present in the opioid-free intra-operative composition are selected from those disclosed above in connection with the opioid-free composition in Section 4.2.

The amount of each component present in the intra-operative composition of the disclosure is an amount to induce and/or maintain analgesia, anesthesia, and/or sedation, as well as maintain hemodynamic stability of the individual in the intra-operative stage of the medical or surgical procedure in the intra-operative methods of the disclosure.

In some embodiments, the magnesium salt is present in the opioid-free intra-operative composition in an amount ranging from about 1 mg/mL to about 370 mg/mL, about 2 mg/mL to about 300 mg/mL, about 3 mg/mL to about 200 mg/mL, about 3.5 mg/mL to about 100 mg/mL, 4 mg/mL to about 50 mg/mL or about 4.5 mg/mL to about 25 mg/mL. In various embodiments, the magnesium salt is present in the opioid-free intra-operative composition in an amount ranging from about 1 mg/mL to about 50 mg/mL, about 2 mg/mL to about 40 mg/mL, about 3 mg/mL to about 30 mg/mL, about 4 mg/mL to about 20 mg/mL or about 5 mg/mL to 10 mg/mL. In various embodiments, the magnesium salt is present in the opioid-free intra-operative composition in an amount of about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, about 15 mg/mL, about 15.5 mg/mL, about 16 mg/mL, about 16.5 mg/mL, about 17 mg/mL, about 17.5 mg/mL, about 18 mg/mL, about 18.5 mg/mL, about 19 mg/mL, about 19.5 mg/mL, or about 20 mg/mL.

In various embodiments, the magnesium salt comprises magnesium sulfate or a magnesium salt functionally equivalent thereto.

In some embodiments, the alpha-2 agonist is present in the opioid-free intra-operative composition in an amount ranging from about 0.001 mcg/mL to about 30 mcg/mL, about 0.005 mcg/mL to about 20 mcg/mL, about 0.01 mcg/mL to about 15 mcg/mL, about 0.025 mcg/mL to about 10 mcg/mL, 0.05 mcg/mL to about 5 mcg/mL, or about 0.1 mcg/mL to about 1 mcg/mL. In various embodiments, the alpha-2 agonist is present in the opioid-free intra-operative composition in an amount of about 0.1 mcg/mL, about 0.2 mcg/mL, about 0.3 mcg/mL, about 0.4 mcg/mL, about 0.5 mcg/mL, about 0.6 mcg/mL, about 0.7 mcg/mL, about 0.8 mcg/mL, about 0.9 mcg/mL, or about 1 mcg/mL.

In various embodiments, the alpha-2 agonist comprises dexmedetomidine or an alpha-2 agonist functionally equivalent thereto.

In some embodiments, the sodium channel inhibitor is present in the opioid-free intra-operative composition in an amount ranging from about 0.1 mg/mL to about 35 mg/mL, about 0.2 mg/mL to about 20 mg/mL, about 0.2.5 mg/mL to about 15 mg/mL, about 0.3 mg/mL to about 10 mg/ml, about 0.4 mg/mL to about 5 mg/mL, or about 0.5 mg/mL to 3 mg/mL. In various embodiments, the sodium channel inhibitor is present in the opioid-free intra-operative composition in an amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, or about 3 mg/mL.

In various embodiments, the sodium channel inhibitor comprises lidocaine or a sodium channel inhibitor functionally equivalent thereto.

In some embodiments, the NMDA antagonist other than a magnesium salt is present in the opioid-free intra-operative composition in an amount ranging from about 0 mg/mL to about 20 mg/mL, about 0.001 mg/mL to about 15 mg/mL, about 0.005 mg/mL to about 10 mg/mL, about 0.01 mg/mL to about 5 mg/mL, about 0.05 mg/mL to about 1 mg/mL, or about 0.1 mg/mL to 0.5 mg/mL. In various embodiments, the NMDA antagonist other than a magnesium salt is present in the opioid-free intra-operative composition in an amount of about 0 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL.

In particular embodiments, the NMDA antagonist other than a magnesium salt present in the opioid-free pre-operative composition comprises ketamine, or an NMDA antagonist functionally equivalent thereto.

In some embodiments, the beta blocker is present in the opioid-free intra-operative composition in an amount ranging from about 0 mg/mL to about 20 mg/mL, from about 0.001 mg/mL to about 15 mg/mL, about 0.01 mg/mL to about 10 mg/mL, about 0.1 mg/mL to about 5 mg/mL, or from about 0.15 mg/mL to about 2.0 mg/mL. In various embodiments, the beta blocker is present in the opioid-free intra-operative composition in an amount of about 0.10 mg/mL, about 0.11 mg/mL, about 0.12 mg/mL, about 0.13 mg/mL, about 0.14 mg/mL, about 0.15 mg/mL, about 0.16 mg/mL, about 0.17 mg/mL, about 0.18 mg/mL, about 0.19 mg/mL, or about 0.20 mg/mL.

In some embodiments, when the beta blocker comprises esmolol, the beta blocker is present in the opioid-free intra-operative composition in an amount ranging from about 0.001 mg/mL to about 20 mg/mL. In other embodiments, when the beta blocker comprises esmolol, the beta blocker is present in the opioid-free intra-operative composition in an amount ranging from about 0.01 mg/mL to about 10 mg/mL or from about 0.1 mg/mL to about 5 mg/mL. In various embodiments, esmolol is present in the opioid-free intra-operative composition in an amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL or about 3 mg/mL.

In one embodiment, the opioid-free intra-operative pharmaceutical composition comprises:

- a magnesium salt in an amount ranging from about 1 mg/mL to about 370 mg/mL;
- an alpha-2 agonist in an amount ranging from about 0.001 mcg/mL to about 30 mcg/mL;
- a sodium channel inhibitor in an amount ranging from about 0.1 mg/mL to about 35 mg/mL;
- an NMDA antagonist other than magnesium salt in an amount ranging from about 0 mg/mL to about 20 mg/mL; and
- a beta-blocker in an amount ranging from about 0 mg/mL to about 20 mg/mL, together with a pharmaceutically acceptable vehicle, carrier, or excipient.

In another embodiment, the opioid-free intra-operative pharmaceutical composition comprises:

- a magnesium salt in an amount ranging from about 5 mg/mL to about 10 mg/mL;
- an alpha-2 agonist in an amount ranging from about 0.1 to about 1 mcg/mL;
- a sodium channel inhibitor in an amount ranging from about 0.5 mg/mL to about 3 mg/mL;
- an NMDA antagonist other than magnesium salt in an amount ranging from about 0 mg/mL to about 0.5 mg/mL; and
- a beta-blocker in an amount ranging from about 0.15 mg/mL to about 2 mg/mL, together with a pharmaceutically acceptable vehicle, carrier, or excipient.

In each of the embodiments described in the preceding two paragraphs, the magnesium salt comprises magnesium sulfate or a magnesium salt functionally equivalent thereto; the alpha-2 agonist comprises dexmedetomidine or an alpha-2 agonist functionally equivalent thereto; the sodium channel inhibitor comprises lidocaine or a sodium channel inhibitor functionally equivalent thereto; the NMDA antagonist other than a magnesium salt, when present, comprises ketamine, or an NMDA antagonist functionally equivalent thereto; and the beta blocker comprises esmolol or a beta blocker functionally equivalent thereto.

4.2.3 Opioid-Free Post-Operative Compositions

In one embodiment, the disclosure provides an opioid-free post-operative composition. The opioid-free post-operative composition comprises one or more of the following:

- a magnesium salt,
- an alpha-2 agonist,
- a sodium channel inhibitor,
- an NMDA antagonist other than magnesium salt, and a beta-blocker, together with a pharmaceutically acceptable vehicle, carrier, or excipient. The amount of each component present in the post-operative composition is an amount effective to treat pain and/or inflammation in the post-operative stage of the medical or surgical procedure, as will be understood by a skilled person upon reading the disclosure.

The particular magnesium salt, alpha-2 agonist, sodium channel inhibitor, NDMA inhibitor and beta-blocker, if present in the opioid-free post-operative composition, are selected from those disclosed above in connection with the opioid-free composition in Section 4.2.

In one aspect of this embodiment, the opioid-free post-operative composition comprises an NMDA antagonist other than magnesium salt. In a second aspect of this embodiment, the opioid-free post-operative composition comprises an NMDA antagonist other than a magnesium salt and a sodium channel inhibitor. In a third aspect of this embodiment, the opioid-free post-operative composition comprises an NMDA antagonist other than a magnesium salt, a sodium channel inhibitor and an alpha-2 agonist. In a fourth aspect of this embodiment, the opioid-free post-operative composition comprises an NMDA antagonist other than a magnesium salt, a sodium channel inhibitor, an alpha-2 agonist and a magnesium salt. In a fifth aspect of this embodiment, the opioid-free post-operative composition comprises an NMDA antagonist other than a magnesium salt, a sodium channel inhibitor, an alpha-2 agonist, a magnesium salt and a beta-blocker.

4.3 Opioid-Free Treatment Methods

In one embodiment, the disclosure provides a method for an opioid-free treatment of an individual undergoing a medical or surgical procedure. In one aspect of this embodiment, the disclosure provides an opioid-free pre-operative treatment of an individual undergoing a medical or surgical procedure. In a second aspect of this embodiment, the disclosure provides an opioid-free intra-operative treatment of an individual undergoing a medical or surgical procedure. In a third aspect of this embodiment, the disclosure provides an opioid-free pen-operative treatment of an individual undergoing a medical or surgical procedure. The methods described in Section 4.3 can be used in any anesthesiological application.

In some embodiments, an electroencephalogram (EEG) can be used to show the EEG data for the patient in the methods of the disclosure. The EEG may be used to determine the overall electrical activity of the brain to monitor blood flow in the brain during medical or surgical procedures and to monitor anesthetic depth for the patient.

4.3.1 Pre-Operative Treatment Methods

The disclosure provides a method for an opioid-free pre-operative treatment of an individual about to undergo a medical or surgical procedure.

In one embodiment, the disclosure provides a method for an opioid-free pre-operative treatment of an individual undergoing a medical or surgical procedure, comprising:

administering to the individual an effective amount of:
- a magnesium salt,
- an alpha-2 agonist, and optionally
- a sodium channel inhibitor, and/or
- a corticosteroid, and/or
- an NMDA other than the magnesium salt.

The particular magnesium salt, alpha-2 agonist, sodium channel inhibitor, corticosteroid and NDMA inhibitor used in the pre-operative method are selected from those disclosed above in connection with the opioid-free composition in Section 4.2.

The amount of each component used in the pre-operative method is an amount effective for treating anxiety and/or inducing sedation, and/or analgesia of the individual in the pre-operative stage of a medical or surgical procedure, as will be understood by a skilled person upon reading of the disclosure.

In some embodiments, the disclosure provides a method for an opioid-free pre-operative treatment of an individual undergoing a medical or surgical procedure, comprising: administering to the individual:
- a magnesium salt in an amount ranging from about 1 to about 50 mg/kg Ideal Body Weight (IBW);
- an alpha-2 agonist in an amount ranging from about 0.1 to 1 about mcg/kg IBW;

and optionally
- a sodium channel inhibitor in an amount ranging from about 0.1 to about 2 mg/kg IBW or from about 0.2 to about 2 mg/kg IBW; and/or
- an NMDA antagonist such as ketamine in an amount ranging from about 0.001 to about 0.5 mg/kg/hr IBW; and/or
- a corticoid in an amount ranging from about 0.001 to about 0.2 mg/kg IBW;

the magnesium salt and alpha-2 agonist, and optionally the sodium channel inhibitor, corticosteroid and NMDA being administered to the individual in combination in an amount effective for treating anxiety and/or inducing sedation, and/or analgesia of the individual in the pre-operative stage of a medical or surgical procedure.

In one aspect of this embodiment, the disclosure provides a method for an opioid-free pre-operative treatment of an individual undergoing a medical or surgical procedure, the method comprising:

administering to the individual an effective amount of:
- a magnesium salt in an amount ranging from 5 to 50 mg/kg Ideal Body Weight (IBW),
- an alpha-2 agonist in an amount ranging from 0.1 to 1 mcg/kg IBW, and optionally
- a sodium channel inhibitor in an amount ranging from 0.1 to 2 mg/kg IBW, and/or
- a corticosteroid in an amount ranging from 0.01 to 0.2 mg/kg IBW, and/or
- an NMDA antagonist other than the magnesium salt in an amount ranging from 0 to 0.5 mg/kg IBW, the magnesium salt and alpha-2 agonist, and optionally the sodium channel inhibitor, corticosteroid and NMDA being administered to the individual in combination in an amount effective for treating anxiety and/or inducing sedation, and/or analgesia of the individual in the pre-operative stage of a medical or surgical procedure.

In various embodiments of the opioid-free pre-operative treatment method, the administering step comprises administering an opioid-free pre-operative composition described herein.

In various embodiments of the pre-operative treatment methods described herein, the method further comprises administering one or more additional agents. In one such embodiment, the method further comprises administering to the individual one or more additional agents selected from the group consisting of a calcium channel inhibitor, a Cox inhibitor, a GABA analogue, an antidepressant, CBD, and/or an antiemetic agent as described in Section 4.2. The amount of the one or more additional agents is an amount effective to stop, reduce, or mitigate pain of a patient during surgery while under an anesthetic condition, sedation or general anesthesia.

In various embodiments in this section, the magnesium salt comprises magnesium sulfate or a magnesium salt functionally equivalent thereto; the alpha-2 agonist comprises dexmedetomidine or an alpha-2 agonist functionally equivalent thereto; the sodium channel inhibitor comprises lidocaine or a sodium channel inhibitor functionally equivalent thereto; the NMDA antagonist other than a magnesium salt, when present, comprises ketamine, or an NMDA antagonist functionally equivalent thereto; and the corticosteroid comprises Dexamethasone.

4.3.2 Intra-Operative Treatment Methods

The disclosure provides a method for an opioid-free intra-operative treatment of an individual undergoing a medical or surgical procedure.

In one embodiment, the disclosure provides a method for an opioid-free intra-operative treatment of an individual undergoing a medical or surgical procedure, the method comprising:

administering to the individual an effective amount of:

magnesium salt;

an alpha-2 agonist;

a sodium channel inhibitor;

and optionally a beta-blocker; and/or an NMDA antagonist other than the magnesium salt.

The particular magnesium salt, alpha-2 agonist, sodium channel inhibitor, beta-blocker and NDMA inhibitor used in the intra-operative method are selected from those disclosed above in connection with the opioid-free composition in Section 4.2.

The amount of each component used in the intra-operative method is an amount effective to induce and/or maintain analgesia, anesthesia, and/or sedation, as well as maintain hemodynamic stability of the individual in the intra-operative stage of the medical or surgical procedure.

In certain embodiments, the method for an opioid-free intra-operative treatment comprises administering to the patient an opioid-free intra-operative pharmaceutical composition of the disclosure.

In some embodiments, the disclosure provides a method for an opioid-free intra-operative treatment of an individual undergoing a medical or surgical procedure, the method comprising:

administering to the individual and effective amount of a magnesium salt in an amount ranging from about 1 mg/kg/hr to about 20 mg/kg/hr Ideal Body Weight (IBW), an alpha-2 agonist in an amount ranging from about 0.01 mg/kg/hr to about 1 mcg/kg/hr IBW, a sodium channel inhibitor in an amount ranging from about 0.1 mg/kg/hr to about 3 mg/kg/hr IBW and optionally a beta-blocker in an amount ranging from about 3 mcg/kg/hr to about 300 mcg/kg/, and/or an NMDA antagonist other than the magnesium salt in an amount ranging from about 0 mg/kg/hr to about 0.5 mg/kg/hr IBW In alternate embodiments, the disclosure provides a method for an opioid-free intra-operative treatment of an individual undergoing a medical or surgical procedure, the method comprising:

administering to the individual:

magnesium salt in an amount ranging from about 5 to about 20 mg/kg/hr IBW;

an alpha-2 agonist in an amount ranging from about 0.1 to about 1 mcg/kg/hr IBW;

a sodium channel inhibitor in an amount ranging from about 1 to about 2 mg/kg/hr IBW; and/or and optionally an NMDA antagonist other than the magnesium salt in an amount ranging from about 0 to about 0.5 mg/kg/hr IBW;

a beta-blocker in an amount ranging from about 3 to about 20 mcg/kg/min IBW.

In some embodiments, the method for an opioid-free intra-operative treatment of an individual undergoing a medical or surgical procedure, the method comprising:

administering to the individual a magnesium salt in an amount ranging from about 7.5 to about 20 mg/kg/hr IBW;

an alpha-2 agonist in an amount ranging from about 0.5 to about 1 mcg/kg/hr IBW;

a sodium channel inhibitor in an amount ranging from about 1.5 to about 3 mg/kg/hr IBW; and and optionally an NMDA antagonist other than magnesium salt in an amount ranging from about 0.2 to about 0.5 mg/kg/hr IBW, and/or a beta-blocker in an amount ranging from about 10 to about 300 mcg/kg/min IBW.

In some embodiments, the method for an opioid-free intra-operative treatment of an individual undergoing a medical or surgical procedure, the method comprising:

administering to the individual:

a magnesium salt in an amount ranging from about 5 to about 7.5 mg/kg/hr IBW;

an alpha-2 agonist in an amount ranging from about 0.1 to about 0.5 mcg/kg/hr IBW; and and optionally an NMDA antagonist other than magnesium salt in an amount ranging from about 0 to about 0.2 mg/kg/hr IBW;

a sodium channel inhibitor in an amount ranging from about 0.5 to about 1.5 mg/kg/hr IBW; and/or a beta-blocker, such as esmolol, in an amount ranging from about 1 to about 10 mcg/kg/min IBW.

In various embodiments of the intra-operative treatment methods described herein, the method further comprises administering one or more additional agents. In one such embodiment, the method further comprises administering to the individual one or more additional agents selected from the group consisting of a calcium channel inhibitor, a Cox inhibitor, and/or an antiemetic agent as described in Section 4.2. The amount of the one or more additional agents is an amount effective to stop, reduce, or mitigate pain of a patient during surgery while under an anesthetic condition, sedation or general anesthesia.

In various embodiments of the intra-operative treatment methods described in this section, the method further comprises administering to the individual additional anesthesia agents in an amount to effective to maintain anesthesia, sedation and/or analgesia as well as stable vital signs of the individual in the intra-operative stage of the medical or surgical procedure. The additional anesthesia agents include, but are not limited to, nitrous oxide and propofol.

4.3.3 Peri-Operative Treatment Methods

The opioid-free pre-operative treatment method and the opioid-free intra-operative treatment method can be used in combination in a peri-operative treatment of an individual undergoing a medical or surgical procedure.

In one aspect, the disclosure provides a method for an opioid-free pen-operative treatment of an individual undergoing a medical or surgical procedure, comprising:

administering to the individual an effective amount of an opioid-free pre-operative treatment according to any one of the methods described herein; and administering to the individual an effective amount of an opioid-free intra-operative treatment according to any one of the methods described herein;

in an amount effective to induce and/or maintain analgesia and/or to reduce inflammation in the individual.

Advantageously, the opioid-free peri-operative treatment methods of the disclosure provide improved post-operative pain relief compared to non-opioid-free peri-operative treatment methods.

4.3.4 Post-Operative Treatment Methods

In one embodiment, the disclosure provides a method for an opioid-free post-operative treatment of an individual following a medical or surgical procedure. The method comprises:

administering to the individual one or more of the following:

a magnesium salt, an alpha-2 agonist, a sodium channel inhibitor, an NMDA antagonist other than magnesium salt, and a beta-blocker, in an amount effective to treat pain and/or inflammation in the post-operative stage of the medical or surgical procedure.

The particular magnesium salt, alpha-2 agonist, sodium channel inhibitor, sodium channel inhibitor, NDMA inhibitor and beta-blocker, if present in the opioid-free post-operative composition, are selected from those disclosed above in connection with the opioid-free composition in Section 4.2.

In another embodiment, the disclosure provides a method for an opioid-free post-operative treatment of an individual following a medical or surgical procedure. The method comprises:

administering to the individual an effective amount of an opioid-free post-operative composition as described herein;

in an amount effective to treat pain and/or inflammation in the post-operative stage of the medical or surgical procedure.

In certain embodiments, the method for an opioid-free intra-operative treatment comprises administering to the patient an opioid-free post-operative pharmaceutical composition of the disclosure selected from those disclosed in Section 4.2.3.

In various embodiments of the post-operative treatment methods described in this section, the method further comprises administering to the individual one or more additional post-operative agents.

In various embodiments of the post-operative treatment methods described in this section, the one or more additional post-operative agents is an antidepressant.

When administered, the antidepressant is selected from the group consisting of (SNRIs), selective serotonin reuptake inhibitors (SSRIs), tricyclic antidepressants (TCAs), tetracyclic antidepressants (TeCA), monoamine oxidase inhibitors (MAOIs), noradrenaline and specific serotoninergic antidepressants (NASSAs).

In embodiments in which the post-operative treatment method comprises administration of an antidepressant, the antidepressant comprises a serotonin and noradrenaline reuptake inhibitor (SNRIs) selected from the group consisting of Venlafaxine, Cymbalta (Duloxetine), Venlafaxine XR, Venlafaxine ER, Desvenlafaxine, and Venlafaxine. In some embodiments, the antidepressant comprises Cymbalta.

In various embodiments of the post-operative treatment methods described in this section, the one or more additional post-operative agents is an analgesic.

In some embodiments, the analgesic is selected from the group consisting of Acetaminophen, Celecoxib, and Pregabalin and combinations thereof.

In various embodiments of the post-operative treatment methods described in this section, the one or more additional post-operative agents comprises Dexamethasone. When administered, the Dexamethasone can be administered over a period of time. The amount and time period for administering Dexamethasone is within the skill of the art, particularly in view of the properties of Dexamethasone and the indications provided in the disclosure.

In some embodiments, the opioid-free post-operative method further comprises administering to the individual Dexamethasone for about one to two days following surgical operation in amount of about 5 mg to about 15 mg over a period of about 15 minutes to about 30 minutes.

4.3.4 Methods of Anesthetizing an Individual

In one embodiment, the disclosure provides a method for anesthetizing an individual undergoing a medical or surgical procedure. The method comprises:

administering to the individual an opioid-free pre-operative composition of the disclosure in an effective amount to treat anxiety and/or induce sedation, and/or analgesia of the individual in the pre-operative stage of a medical or surgical procedure;

administering to the individual an opioid-free intra-operative composition of the disclosure in an effective amount to induce and/or maintain analgesia, anesthesia, and/or sedation, as well as maintain hemodynamic stability of the individual in the intra-operative stage of the medical or surgical procedure;

and optionally administering to the individual an opioid-free post-operative composition of the disclosure in an effective amount to treat pain and/or inflammation of the individual during the post-operative stage of the medical or surgical procedure.

The particular opioid-free pre-operative composition, opioid-free intra-operative composition and opioid-free post-operative composition used in the methods of anesthetizing an individual are selected from those disclosed above in Section 4.2.1, Section 4.2.2, and Section 4.2.3, respectively.

4.4. Dose Levels, Regimens and Modes of Administration

In methods described in Section 4.3, it will be understood that the total dosage of one or more agents and/or compositions of the disclosure will be decided by a patient's attending anesthesia provider within the scope of sound medical judgment. The specific therapeutically effective dose level for any particular patient will depend upon a variety of factors including, comorbidities and the severity of the comorbidities; activity of the specific agents and/or compositions employed; the age, body weight, general health, sex and diet of the patient; the time of administration, route of administration, and rate of excretion of the specific agents employed; the duration of the treatment; drugs used in combination or coincidental with the specific agents/compositions employed; and other factors known to those of ordinary skill in the medical arts.

In selecting one or more agents used in the methods described herein, the anesthesia provider will typically consider the features of the specific agent in view of the status of the health condition of the individual to be treated. For example, the anesthesia provider will consider in selecting an alpha-2 agonist, such as guanoxabenz (a metabolite of guanabenz in the human liver, antihypertensive, antiadrenergic agent), guanethidine (antihypertensive agent that acts by inhibiting selectively transmission in post-ganglionic adrenergic nerves, suppresses equally the responses mediated by alpha- and beta-adrenergic receptors without producing parasympathetic blockade, available in oral form), xylazine (an analogue of clonidine and agonist at the α-2 class of adrenergic receptor typically used for sedation, anesthesia, muscle relaxation and analgesia in animals such as horses, cattle and other non-human mammals and as an emetic, especially in cats.), tizanidine (a central muscle relaxant, a short-acting drug that can also be used for the management of spasticity by increasing presynaptic inhibition of motor neurons, the effects of tizanidine being greatest on polysynaptic pathways, the overall effect of these actions being reducing facilitation of spinal motor neurons), medetomidine (synthetic compound typically used a surgical anesthetic and analgesic for veterinary use in dogs, as a racemic mixture of two stereoisomers from which dexmedetomidine is the main active isomer), (R)-3-nitrobiphenyline, detomidine, lofexidine, and medetomidine, and guanfacine (a centrally acting adrenergic agonist with non-stimulant and antihypertensive property that selectively stimulates α-2 adrenergic receptors in the CNS, thereby resulting in inhibition of sympathetic nervous system outflow).

Additionally, the anesthesia provider will typically select the specific dosages and timing of administration taking into account the different pharmacokinetic of the specific agents. For example, exemplary beta-blockers esmolol, metoprolol, and labetalol have different pharmacokinetic parameters. The pharmacokinetic parameters of esmolol are as follows: Onset: Immediate; Peak: 2-6 minutes; Duration >20 minutes The pharmacokinetic parameters of metoprolol are as follows: Onset: Immediate; Peak: 20 minutes; Duration 5-8 hrs. The pharmacokinetic parameters of labetalol are as follows: Onset: 2-5 minutes; Peak 5-15 minutes; Duration up to 4 hours.

Accordingly, in some exemplary embodiments, esmolol can be used preferably as a continuous infusion because of its titratability, rapid onset and offset. Metoprolol, which is a beta blocker, and Labetalol, which is a 7:1 ratio beta-blocker and alpha-1 adrenoreceptor antagonist, and/or other medication commonly used in anesthesia can also be administered as IV boluses to control hypertension and/or rapid heart rate. Intra-operative beta-blocker can be administered as a prevention of a cardiac event. In general, a long acting β-blocker is less desirable in the context of opioid-free administration as a more titratable beta-blocker is preferred.

Additional considerations can be taken into account by an anesthesia provider in deciding the dosages and timing of administration for the pen-operative treatment methods of the disclosure.

Figure 2:
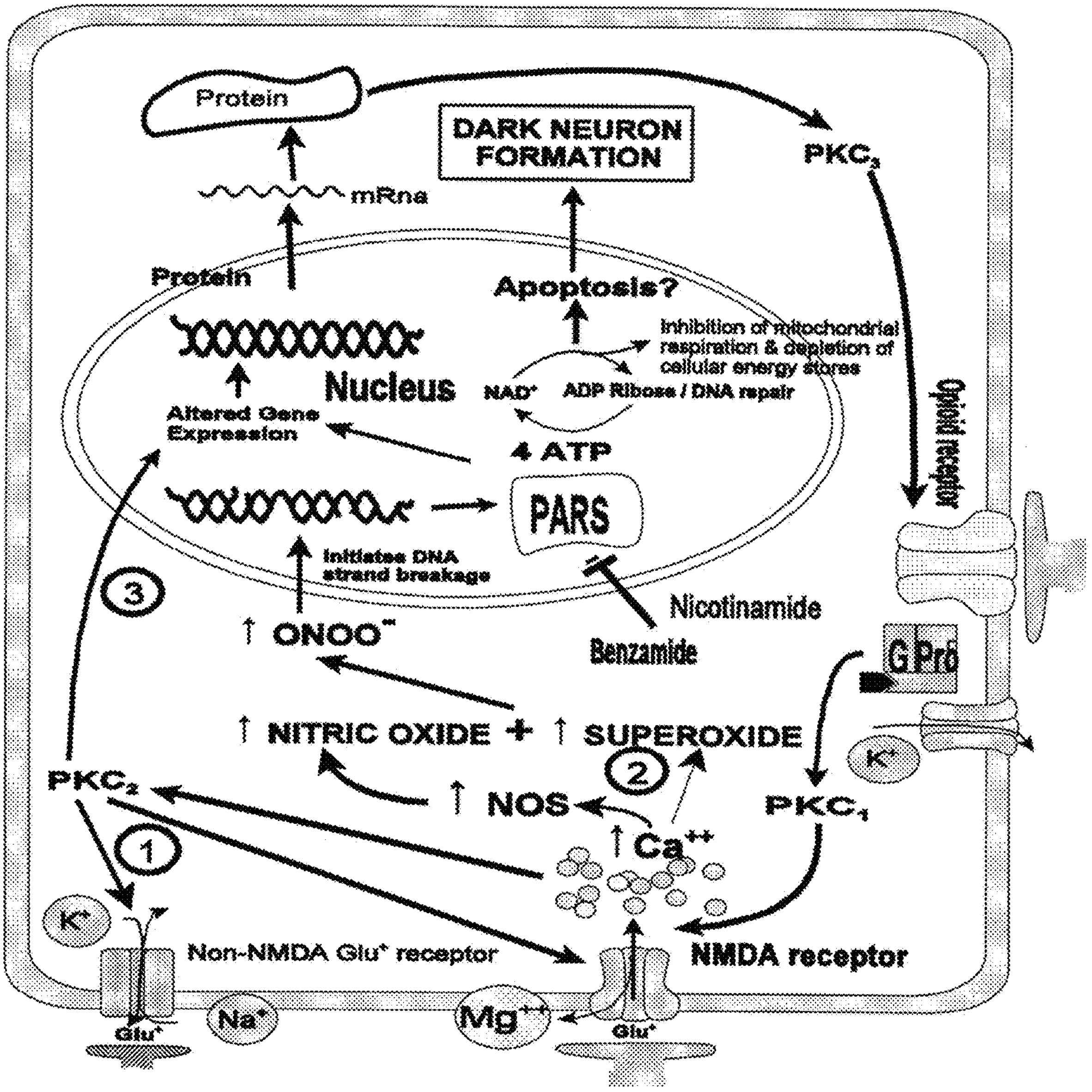
Figure 3:
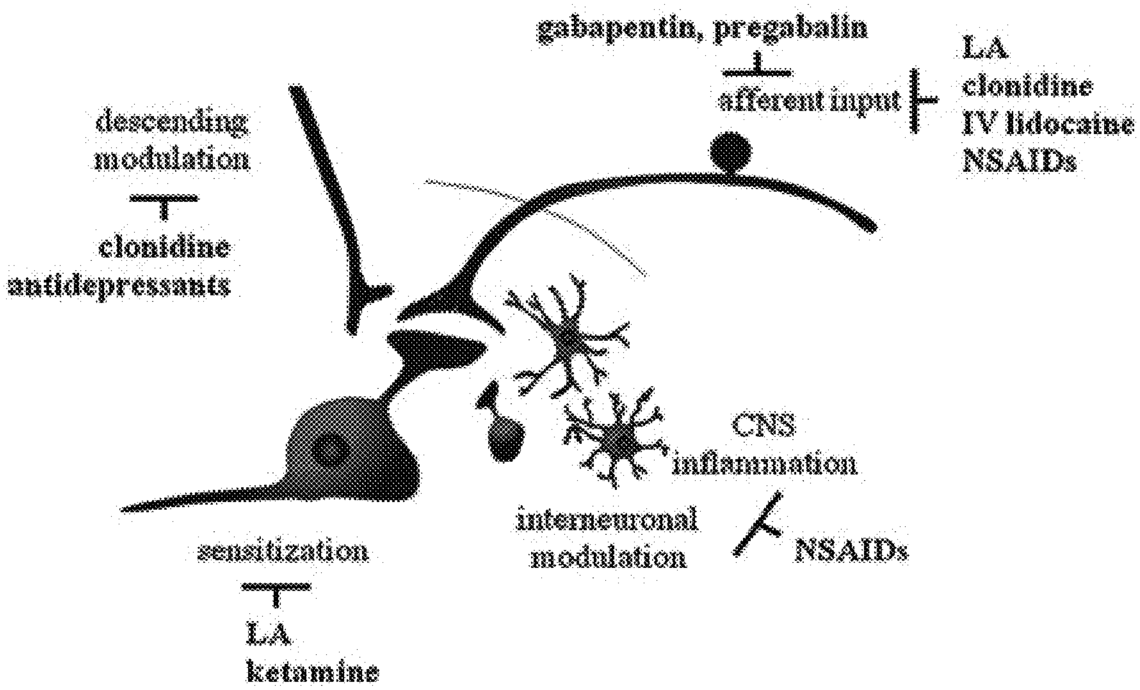

For example, the timing and dosages of magnesium salt are typically selected to increase the gradient of $Mg^{2+}$ extracellularly in order to keep the $Mg^{2+}$ "plug" within the NMDA receptor in place. If the $Mg^{2+}$ is displaced within the channel of the NMDA receptor it sets off a cascade that ultimately results in increased noxious stimuli perception (see FIG. 2). In particular, in opioid-free pre-operative, intra-operative or post-operative compositions of the disclosure magnesium salt is given to increase the gradient of $Mg^{2+}$ extracellularly in order to keep the $Mg^{2+}$ "plug" within the NMDA receptor in place. $Mg^{2+}$ salt infusion should be used cautiously or avoided in renal failure and/or high degree heart block as will be understood by a skilled person. In some embodiments, for very long cases an $Mg^{2+}$ salt infusion can be lowered so that the cumulative dose does not cause unwanted side effects from high plasma levels of $Mg^{2+}$ salt such as muscle weakness, inability to reverse muscle relaxant, hypotension, and extreme cases bradyarrhythmia's.

In some embodiments in which the alpha-2 receptor antagonist is dexmedetomidine, dosages and timing of administration can be selected taking into account that the dexmedetomidine can be given in higher loading and infusion dose to individuals who are very agitated, are nervous, have a history of post-traumatic stress disorder, are male between the ages of 18-24 who tend to demonstrate elevated sympathetic tone. Dexmedetomidine can also be given in lieu of other anesthetics for its neuroprotective effects, especially in the elderly. Dexmedetomidine can be increased for more stimulating surgeries when this infusion is being used as the primary pain and stress reducing modality as will be understood by a skilled person. It is worth considering that by reducing stress (even pre-existing/non-pain related stress) would result in a reduction of inflammation. Stress causes the release of proinflammatory cytokines regardless of the origin of stress. In some embodiments, the dosage of dexmedetomidine can be lowered to reduce unwanted side effects, such as hypotension, bradycardia, and excessive urination.

In some embodiments, patients receive nerve blocks, epidurals or spinals in combination with general anesthesia for major surgeries. These interventions reduce the transmission of pain signals to the brain, the result is that the patient does not react or have a stress response to the noxious stimuli (in this case surgery). If the pain is blocked from being perceived, the anesthetic dose can stay relatively low even if it is a major surgery. If there is no block and the noxious stimuli is severe, the dose of dexmedetomidine will likely need to be increased. If the patient is very anxious before surgery or has a history of chronic anxiety, post-traumatic stress disorder (PTSD) or is a male between the ages of 17-24 higher doses of dexmedetomidine might be required to effectively attenuate the sympathetic nervous system outflow during surgery and to aid with a smoother emergence from anesthesia.

In some embodiments, because of the profound anti-inflammatory effects of the OFA medications, it is still beneficial to administer the OFA medications even in the circumstance that noxious stimuli are not being transmitted while the block/spinal is in effect. The pain and inflammation reducing properties of OFA will outlast the pain alleviating properties of the block/spinal as will be understood by a skilled person. The block would help to bypass the most painful period immediately after the surgery, but the OFA medications will aid in the reduction of pain intensity after the block wears off as compared with an individual that did not receive OFA mediations.

In some embodiments, in which the patient has heart block, bradyarrhythmia's, severe ventricular dysfunction, hypovolemia, or poorly controlled hypertension, or is elderly, the anesthesia provider should use caution in selecting alpha-2 adrenoreceptor blockers and the dosages and timing of administration.

In some embodiments, in which the patient is diabetic or at high risk for infections, the steroid administration can be reduced or eliminated as will be understood by a skilled person.

In other embodiments in which Dexamethasone (dexamethasone sodium phosphate) is administered, the related timing and dosage can be selected taking into account that Dexamethasone cause insulin resistance for a period of 24 hours after its administration and less for other shorter acting steroids. Dexamethasone can be eliminated if other steroids were indicated such as in a case to prevent adrenal crisis. Adrenal crisis can be a concern if the patient has chronically taken exogenous steroids and is assumed to have some degree of adrenal insufficiency. Examples include conditions such as osteoarthrosis, autoimmune disorder or bronchial reactive airway problems. Therapy to reduce the likelihood of adrenal crisis for such patients includes hydrocortisone. Dexamethasone sodium phosphate is within the class of glucocorticosteroids and is more potent and longer acting than hydrocortisone and can be used as therapy to prevent an adrenal crisis in these patients.

In some embodiments in which access to basic hygiene, such as running water, is problematic, the methods of the disclosure comprise administering a reduced dose of steroids to minimize the risk of infection. In some embodiments, the methods of the disclosure comprise administering an increased dose of Dexamethasone for pain control than the doses commonly used by anesthesia providers to prevent post-operative nausea and vomiting (~4 mg).

In certain embodiments, in pre-operative treatment methods, the individual components or the pre-operative compositions of the disclosure can be administered via parenteral (e.g., subcutaneous, intramuscular, or intravenous) or intranasal. In certain embodiments, the individual components or the pre-operative compositions of the disclosure can be administered by intravenous infusion. In one aspect, the individual components or the pre-operative compositions of the disclosure can be administered by intravenous infusion via bolus.

In some embodiments, in pre-operative treatment methods, the individual components or the pre-operative compositions of the disclosure are administered as a single bolus dose over a period of time, ranging from about 15 minutes to about 60 minutes, about 20 minutes to about 50 minutes, about 15 minutes to about 40 minutes, about 15 minutes to about 30 minutes, or about 20 minutes to about 25 minutes.

In embodiment in which the opioid-free pre-operative composition is administered by intravenous infusion, it is a liquid composition that can be contained in a syringe, IV bag, or glass container (vial or bottle). A pharmaceutically effective amount of the liquid composition can be given IV over a period of time, e.g., about 15 minutes. Alternatively, the pharmaceutically effective amount of the liquid composition can be drawn up in a quantity of the loading dose, injected into a 25, 50, or 100 cc IV bag of fluid and then administered to a patient over about 15 minutes, about 30 minutes, about 45 minutes, or about 1 hour or more.

In particular embodiments of the pre-operative treatment method, the magnesium salt is administered in an amount ranging from about 1 mg/mL to about 500 mg/mL, about 2 mg/mL to about 300 mg/mL, about 3 mg/mL to about 300 mg/mL, about 4 mg/mL to about 300 mg/mL, about 5 mg/mL to about 300 mg/mL, about 50 mg/mL to about 300 mg/mL, or about 100 mg/mL to about 300 mg/mL. In particular embodiments, the magnesium salt is present in the opioid-free pre-operative composition in an amount of about 1 mg/mL, about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, about 400 mg/mL, about 410 mg/mL, about 420 mg/mL, about 430 mg/mL, about 440 mg/mL, about 450 mg/mL, about 460 mg/mL, about 470 mg/mL, about 480 mg/mL, about 490 mg/mL, or about 500 mg/mL.

In particular embodiments of the pre-operative treatment method, the alpha-2 agonist is administered in an amount ranging from about 0.001 mcg/mL to about 50 mcg/mL, 0.01 mcg/mL to about 50 mcg/mL, about 0.1 mcg/mL to about 40 mcg/mL, about 0.2 mcg/mL to about 30 mcg/mL, about 0.3 mcg/mL to about 20 mcg/mL, 0.4 mcg/mL to about 15 mcg/mL, about 0.5 mcg/mL to about 10 mcg/mL, about 1 mcg/mL to about 10 mcg/mL, about 2 mcg/mL to about 10 mcg/mL, or about 3 mcg/mL to about 10 mcg/mL. In particular embodiments, the one alpha-2 agonist is administered in an amount of about 0.1 mcg/mL, about 0.2 mcg/mL, about 0.3 mcg/mL, about 0.4 mcg/mL, about 0.5 mcg/mL, about 0.6 mcg/mL, about 0.7 mcg/mL, about 0.8 mcg/mL, about 0.9 mcg/mL, about 1 mcg/mL, about 1.5 mcg/mL, about 2 mcg/mL, about 2.5 mcg/mL, about 3 mcg/mL, about 3.5 mcg/mL, about 4 mcg/mL, about 4.5 mcg/mL, about 5 mcg/mL, about 5.5 mcg/mL, about 6 mcg/mL, about 6.5 mcg/mL, about 7 mcg/mL, about 7.5 mcg/mL, about 8 mcg/mL, about 8.5 mcg/mL, about 9 mcg/mL, about 9.5 mcg/mL, about 10 mcg/mL, about 10.5 mcg/mL, about 11 mcg/mL, about 11.5 mcg/mL, about 12 mcg/mL, about 12.5 mcg/mL, about 13 mcg/mL, about 13.5 mcg/mL, about 14 mcg/mL, about 14.5 mcg/mL, or about 15 mcg/mL.

In particular embodiments of the pre-operative treatment method, the sodium channel inhibitor is administered in an amount ranging from about 0 mg/mL to about 40 mg/mL, about 0.01 mg/mL to about 36 mg/m, about 2.5 mg/mL to about 30 mg/mL, about 4 mg/mL to about 25 mg/mL, or about 10 mg/mL to about 20 mg/mL. In various embodiments, the sodium channel inhibitor is administered in an amount ranging from about 1 mg/mL to about 10 mg/mL, about 2 mg/mL to about 8 mg/mL, about 3 mg/mL to about 7 mg/mL, or about 4 mg/mL to about 6 mg/mL. In particular embodiments, the sodium channel inhibitor is administered in an amount of about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, about 15 mg/mL, about 15.5 mg/mL, about 16 mg/mL, about 16.5 mg/mL, about 17 mg/mL, about 17.5 mg/mL, about 18 mg/mL, about 18.5 mg/mL, about 19 mg/mL, about 19.5 mg/mL, or about 20 mg/mL.

In particular embodiments of the pre-operative treatment method, the at least one NMDA antagonist other than magnesium salt is administered in an amount ranging from about 0 mg/mL to about 35 mg/mL, about 0.01 mg/mL to about 30 mg/mL, about 1 mg/mL to about 25 mg/mL, about 1.5 mg/mL to about 20 mg/ml, about 2 mg/mL to about 15 mg/mL, about 2.5 mg/mL to about 10 mg/mL, or about 3 mg/mL to about 5 mg/mL. In various embodiments, the at least one NMDA antagonist other than a magnesium salt is administered in an amount of about 0.5 mg/mL, about 1 mg/mL, about 1.5 mg/mL, about 2 mg/mL, about 3.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, or about 10 mg/mL.

In particular embodiments of the pre-operative treatment method, the at least one corticosteroid is administered in an amount ranging from about 0 mg/mL to about 10 mg/mL, about 0.2 mg/mL to about 9 mg/mL, about 0.4 mg/mL to about 8 mg/mL, about 0.6 mg/mL to about 7 mg/mL, about 0.8 mg/mL to about 6 mg/mL, about 1 mg/mL to about 5 mg/mL, or about 1.5 mg/mL to about 4 mg/mL. In some embodiments, the corticosteroid is administered in amount ranging from about 0.1 mg/mL to about 5 mg/mL, about 0.15 mg/mL to about 4 mg/mL, from about 0.2 mg/mL to about 3 mg/mL, from about 0.25 to about 2 mg/mL, or about 0.3 mg/mL to about 1 mg/mL. In various embodiments, the corticosteroid is administered in amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, or about 2 mg/mL.

In certain embodiments, in intra-operative treatment methods, the individual components or the intra-operative compositions of the disclosure can be administered via parenteral (e.g., subcutaneous, intramuscular, or intravenous) or intranasal. In certain embodiments, the individual components or the intra-operative compositions of the disclosure can be administered by intravenous infusion. In one aspect, the individual components or the intra-operative compositions of the disclosure can be administered by intravenous continuous infusion or via bolus doses.

In particular embodiments of the intra-operative treatment methods, the magnesium salt is administered in an amount ranging from about 1 mg/mL to about 370 mg/mL, about 2 mg/mL to about 300 mg/mL, about 3 mg/mL to about 200 mg/mL, about 3.5 mg/mL to about 100 mg/mL, 4 mg/mL to about 50 mg/mL or about 4.5 mg/mL to about 25 mg/mL. In various embodiments, the magnesium salt is administered in an amount ranging from about 1 mg/mL to about 50 mg/mL, about 2 mg/mL to about 40 mg/mL, about 3 mg/mL to about 30 mg/mL, about 4 mg/mL to about 20 mg/mL or about 5 mg/mL to 10 mg/mL. In various embodiments, the magnesium salt is administered in an amount of about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, about 15 mg/mL, about 15.5 mg/mL, about 16 mg/mL, about 16.5 mg/mL, about 17 mg/mL, about 17.5 mg/mL, about 18 mg/mL, about 18.5 mg/mL, about 19 mg/mL, about 19.5 mg/mL, or about 20 mg/mL.

In particular embodiments of the intra-operative treatment method, the at least one alpha-2 agonist is administered in an amount ranging about 0.001 mcg/mL to about 30 mcg/mL, about 0.005 mcg/mL to about 20 mcg/mL, about 0.01 mcg/mL to about 15 mcg/mL, about 0.025 mcg/mL to about 10 mcg/mL, 0.05 mcg/mL to about 5 mcg/mL, or about 0.1 mcg/mL to about 1 mcg/mL. In various embodiments, the alpha-2 agonist is administered in an amount of about 0.1 mcg/mL, about 0.2 mcg/mL, about 0.3 mcg/mL, about 0.4 mcg/mL, about 0.5 mcg/mL, about 0.6 mcg/mL, about 0.7 mcg/mL, about 0.8 mcg/mL, about 0.9 mcg/mL, or about 1 mcg/mL.

In particular embodiments of the intra-operative treatment method, the at least one sodium channel inhibitor is administered in an amount ranging from about 0.1 mg/mL to about 35 mg/mL, about 0.2 mg/mL to about 20 mg/mL, about 0.2.5 mg/mL to about 15 mg/mL, about 0.3 mg/mL to about 10 mg/ml, about 0.4 mg/mL to about 5 mg/mL, or about 0.5 mg/mL to 3 mg/mL. In various embodiments, the sodium channel inhibitor is administered in the opioid-free intra-operative composition in an amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, or about 3 mg/mL.

In particular embodiments of the intra-operative treatment method, the at least one NMDA antagonist other than magnesium salt is administered in an amount ranging from about 0 mg/mL to about 20 mg/mL, about 0.001 mg/mL to about 15 mg/mL, about 0.005 mg/mL to about 10 mg/mL, about 0.01 mg/mL to about 5 mg/mL, about 0.05 mg/mL to about 1 mg/mL, or about 0.1 mg/mL to 0.5 mg/mL. In various embodiments, the NMDA antagonist other than a magnesium salt is administered in an amount of about 0 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL.

In particular embodiments of the intra-operative treatment method, the at least one beta blocker is administered in an amount ranging from about 0 mg/mL to about 20 mg/mL, from about 0.001 mg/mL to about 15 mg/mL, about 0.01 mg/mL to about 10 mg/mL, about 0.1 mg/mL to about 5 mg/mL, or from about 0.15 mg/mL to about 2.0 mg/mL. In various embodiments, the beta blocker is administered in an amount of about 0.10 mg/mL, about 0.11 mg/mL, about 0.12 mg/mL, about 0.13 mg/mL, about 0.14 mg/mL, about 0.15 mg/mL, about 0.16 mg/mL, about 0.17 mg/mL, about 0.18 mg/mL, about 0.19 mg/mL, or about 0.20 mg/mL.

In certain embodiments, an additional beta-blocker can be given to supplement the infusion, depending on the patient's conditions and response to the surgery. Alternately, dosing/concentrations of either the beta-blocker or Dexmedetomidine can be increased if a patient's response to surgical stimulation is being observed.

In particular embodiments of the peri-operative treatment method, the opioid-free compositions are administered by intramuscular administration, e.g. into the mid-lateral thigh and/or the arm of the individual.

In some embodiments, opioid-free compositions of the disclosure can be contained in a 5 ml, 10 ml, 20 ml, 30 ml, 50 ml or 60 ml vial or syringe. The opioid-free compositions, and in particular, the pre-operative opioid-free composition, can be administered undiluted via IV over time, e.g., about 15 minutes. Alternatively, the pharmaceutically effective amount of the opioid-free composition can be drawn up in a quantity of the loading dose, diluted into a 50 or 100 cc IV bag/bottle of fluid and infused IV over 15 minutes, 30 minutes, 45 minutes, 1 hour or more.

In some embodiments, the opioid-free intra-operative compositions of the disclosure can be administered as a continuous infusion over the duration of the surgery. The duration of the surgery can last for under one hour to several hours depending on the complexity of the medical or surgical procedure.

In embodiments herein described in which the opioid-free composition is used concurrently with an additional anesthetic agent, such as propofol and/or inhalation agents (anesthesia gasses), the dosage requirement of the additional anesthetic agent is markedly reduced.

In particular embodiments, the reduction of dosage of the at least one anesthetic agent is at least about 1%, about 5%, about 10%, about 25%, about 50%, about 60% or about 75%. In some embodiments, the reduction of dosage of the at least one anesthetic agent is at least about 1%, about 5%, about 10%, about 25%, about 50%, about 60% or about 75%, wherein the at least one anesthetic agent comprises ketamine.

When selecting dosages and methods of the disclosure, the following considerations should be taken into account.

When administering an opioid-free pre-operative composition, one consideration in determining the speed of the loading dose administration is set by how fast it can be administered without exacerbating undesirable side effects. Commonly seen side effects from the administration of the loading dose in addition to the perineal burning includes a feeling of intense generalized heat described as a "hot flash" by patients. There can be discomfort at the IV site and, in some cases, feeling of numbness to the extremity in which the IV is located. In rare cases, there can be a feeling of generalized body weakness. The faster the infusion is, the more commonly and intense the symptoms are. The slower the infusion, the less likely the patient notices any side effects other than sedation, which is experienced approximately 10 minutes after the infusion is initiated. In some embodiments, the rate is a 10 ml volume in about 15 minutes (35 cc/hr).

The OFA preemptive analgesia loading dose of the disclosure can comprise dexamethasone sodium phosphate. Dexamethasone sodium phosphate is usually given after the induction of anesthesia because it causes an undesirable perineum burning side effect. As a result, there is an abbreviated time between its administration and the mechanical tissue trauma beginning with surgical incision. However this practice negates some of the potential benefits.

Because most of the OFA medications are given separately, each additional tool is perceived as increased work by the anesthesia provider. In addition, unlike most medications used in anesthesia have an immediate effect upon administration, OFA medications are exceptions. Therefore, timing of administration of a composition of the disclosure should be a factor to consider.

The combined effect of the medications in a composition of the disclosure provides a mechanism of pain control beyond merely the absence of opioids and with superior analgesia. This type of opioid-free anesthesia substantially obliterates the most common "side effects of anesthesia" associated with opioid medication and provides superior pain control well beyond the intra-operative period. The use of opioids two weeks after surgery is strongly correlated with opioid use 1 year after surgery. This is pertinent given the known risk of opioid use disorder after surgery in opioid naive patients.

The loading dose of medication of perioperative composition can be infused over approximately 15 minutes prior to taking the patient into the operating room. This gives the dexmedetomidine the time needed to produce the calming/sedative effect and generally negates the need to administer an anxiolytic medication prior to induction of anesthesia. The sedation effect remains for approximately 30 minutes after administration thereby providing an effective state lasting 45 minutes after the loading dose. If the surgery was postponed by 1-2 hours after the loading dose was given, only the loading dose of dexmedetomidine and lidocaine if used as part of the pre-op loading dose would be repeated immediately before surgery.

Either an RN or an anesthesia provider can administer the correct volume and rate of this loading dose composition while assessing vital sign and level of consciousness.

It is not imperative that the onset of sedation has set in prior to taking the patient into the operating room, but it is a benefit in that anxiolytic versed (Midazolam) another anesthetic medication commonly given can be eliminated. Versed is a benzodiazepine that should be used cautiously or avoided in some populations. Post-operative cognitive decline is a known side effect for which elderly patients are especially vulnerable. It is a controlled substance, so there is a specific protocol for obtaining the medication and wasting any remaining medication requires careful documentation and a witness. This medication is commonly given to the patient either just when leaving pre-operative area to go into the operating room or immediately when the patient arrives into the operating room. Once in the operating room the maintenance infusion is started. The anesthetic agent propofol is commonly administered as a bolus (single dose all at once) to induce anesthesia, resulting in loss of consciousness. After the induction a continuous infusion of intravenous medication (propofol) and/or anesthesia gasses via the breathing circuit are titrated to maintain stage 3 anesthetic depth (optimal anesthetic depth for surgery between a conscious state and medullary depression/death). When the procedure is coming to a close, the agents are turned off, the effect wears off and the patient emerges from anesthesia.

Another reason to give the loading dose medication with ample time prior to the incision is to allow for the steroid to take effect. The steroid most commonly used with anesthesia practice is dexamethasone which takes at least 1 hour until peak effect. It is ideal for the steroid to be at its peak effect prior to surgical incision as the surgical trauma will cause local inflammatory changes at the site. Dexamethasone is administered after the patient is asleep because it causes undesirable effect of intense perineum burning if given quickly as an IV bolus to an awake patient. This does not leave enough time between induction of anesthesia (and dexamethasone administration) and incision for the peak effect. This lag time "prep time" is usually between 10-30 minutes but can be as long as 1 hour in some cases.

For very short cases sometimes an OFA loading dose is used pre-operatively but instead of running an infusion of these medications it will be given in incremental boluses of components of these medications including ketamine, dexmedetomidine and lidocaine. Some of the surgical/procedural cases are only 10-15 minutes long. When running an infusion, it takes 20+ minutes before the onset of the infusion is noted. The other time-sensitive consideration is that it is ideal to turn the infusion off approximately 20 minutes before emergence from anesthesia. If the infusion is continued right until the very end of closure of the incision there will be a long lag time for wakeup which is undesirable for any case. This is especially true in cases when the patient has an advanced airway in place that needs to be removed/pt. extubated before leaving the operating room. There are very few cases when the patient can remain intubated (big hospitals with major surgeries). Most of the cases done in the United States are on an outpatient basis. This type of anesthetic is thus preferably adaptable to the outpatient setting and, generally speaking, for shorter cases with healthier patients. It is very probable that in the outpatient setting there will be a higher utilization of bolus dosing for some of these medications so that the peak onset is reached quicker, and the offset can be better predicted/timed. Time equates to money in the surgical setting, so timing offset is of the utmost importance.

4.5 Systems

In one aspect, the disclosure provides systems for anethesiological applications.

In embodiments herein described, the magnesium salt, the alpha-2 agonist, and optionally the sodium channel inhibitor, corticosteroid, beta-blocker and NMDA antagonist can be comprised in opioid-free pre-operative, opioid-free intra-operative, opioid-free post-operative and/or opioid-free peri-operative systems in accordance with the present disclosure.

In opioid-free systems of the disclosure the magnesium salt, the alpha-2 agonist, and optionally the sodium channel inhibitor, corticosteroid, beta-blocker and NMDA antagonist of the disclosure can be formulated in separate dosage forms that are provided as part of the system in various combinations one with another in accordance with the present disclosure.

Accordingly, in some embodiments, the agents and related composition of the disclosure can be provided as part of an opioid-free peri-operative system, for an opioid-free peri-operative treatment of an individual. The opioid-free pre-operative and intra-operative system can comprise, magnesium salt, an alpha-2 agonist, and optionally an NMDA antagonist other than a magnesium salt, a sodium channel inhibitor, beta-blocker and/or a corticosteroid.

In the opioid-free pre-operative system the magnesium salt, alpha-2 agonist and optionally the sodium channel inhibitor, NMDA antagonist other than a magnesium salt, and/or corticosteroid are comprised in an effective amount for simultaneous, combined or sequential use as herein described.

Optionally the opioid-free pre-operative system can further comprise a calcium channel inhibitor, Cox inhibitor, corticosteroid, GABA analogue, antidepressant, cannabidiol (CBD), and/or antiemetic agent for simultaneous, combined or sequential use as herein described.

In some embodiments, the system can also comprise one or more agents of the disclosure in combination with one or more agents for treatment of a condition associated with surgical operation. In system the components can be comprised in the system independently possibly included in a composition together with suitable vehicle, carrier, or excipient including carrier or auxiliary agents as will be understood by a skilled person.

Typically, in a system of the disclosure, one or more agents are provided in separate dosage forms to be combined at the proper time during, before or after the medical or surgical procedure to provide opioid-free compositions according to the present disclosure and/or to perform any one of the methods herein described.

In some embodiments, a system can comprise a magnesium salt composition, an alpha-2 agonist composition, a sodium channel inhibitor composition, and optionally a NMDA antagonist other than magnesium salt composition, a beta-blocker composition, and/or a corticosteroid composition, in any combination optionally further including a pharmaceutically acceptable vehicle, carrier, or excipient. In those embodiments each composition comprises the respective agent together with a pharmaceutically acceptable vehicle in separate dosage forms to be combined to provide a pre-operative opioid-free composition, intra-operative opioid-free composition, or post-operative opioid-free composition of the disclosure and/or to be administered in any one of the methods herein described.

In some embodiments, the system can comprise:

(1) a magnesium salt composition in a concentration described in any one Sections 4.2.1, 4.2.2 or 4.2.3 for an opioid-free composition comprising a magnesium salt;

(2) an alpha-2 agonist composition in a concentration described in any one Sections 4.2.1, 4.2.2 or 4.2.3 for an opioid-free composition comprising an alpha-2 agonist;

(3) a sodium channel inhibitor composition in a concentration described in any one of Sections 4.2.1, 4.2.2 or 4.2.3 for an opioid-free composition comprising a sodium channel inhibitor;

and optionally (4) an NMDA antagonist, other than a magnesium salt, composition in a concentration described in any one of Sections 4.2.1, 4.2.2, or 4.2.3 for an opioid-free composition comprising an NMDA antagonist, other than a magnesium salt; and/or (5) a beta-blocker composition in a concentration described in any one of Sections 4.2.1, 4.2.2, or 4.2.3 for an opioid-free composition comprising a beta-blocker; and/or (6) a corticosteroid composition in a concentration described in any one of Sections 4.2.1, 4.2.2, or 4.2.3 for an opioid-free composition comprising a corticosteroid;

and optionally a container;

to be combined to provide any one of the opioid-free compositions of the disclosure and/or to be administered in any one of the methods herein described.

The particular magnesium salt, alpha-2 agonist, and sodium channel inhibitor, and optionally NMDA antagonist, other than a magnesium salt, a beta-blocker, and corticosteroid provided in the systems are selected from those disclosed above in connection with the opioid-free composition in Section 4.2.

In one embodiment, the disclosure provides a system for an opioid-free pre-operative treatment of an individual, the system comprising a magnesium salt, an alpha-2 agonist, and optionally a sodium channel inhibitor, an N-methyl-D-aspartate receptor (NMDA) inhibitor, and/or a corticosteroid.

In a second embodiment, the disclosure provides a system for an opioid-free intra-operative treatment of an individual, the system comprising a magnesium salt, an alpha-2 agonist, a sodium channel inhibitor, and optionally an NMDA antagonist other than a magnesium salt, and/or a beta-blocker.

In a third embodiment, the disclosure provides a system for the post-operative treatment of an individual, the system comprising one or more of a magnesium salt, an alpha-2 agonist, a sodium channel inhibitor, an NMDA antagonist other than a magnesium salt, and a beta-blocker.

In the system for an opioid-free pre-operative treatment of an individual, the magnesium salt, alpha-2 agonist, and optionally the sodium channel inhibitor, NMDA inhibitor, and/or corticosteroid are comprised in an effective amount for simultaneous combined or sequential use to prepare an pre-operative composition herein described.

In the system for an opioid-free intra-operative treatment of an individual the magnesium salt, alpha-2 agonist, sodium channel inhibitor and the optional NMDA antagonist other than the magnesium salt and/or beta-blocker are comprised in an effective amount for simultaneous combined or sequential use to prepare an intra-operative composition herein described.

In the system for an opioid-free post-operative treatment of an individual, the one or more of a magnesium salt, an alpha-2 agonist, a sodium channel inhibitor, an NMDA antagonist other than a magnesium salt, and a beta-blocker are comprised in an effective amount for simultaneous combined or sequential use to prepare an post-operative composition herein described.

Accordingly, in some embodiments, a system of the disclosure can further comprise a pharmaceutically acceptable vehicle, carrier, or excipient to be combined to provide an opioid-free pre-operative composition, an opioid-free intra-operative composition, or an opioid-free post-operative composition of the disclosure and/or to be administered in any one of the methods herein described.

In some embodiments, the compositions described herein can be pre-mixed by a manufacturing company and a provider would not need to mix agents contained in the composition. Optionally, the provider would be provided instructions on how to administer the composition.

In each of the embodiments described above, the container comprising the individual ingredients or the opioid-free compositions of the disclosure may be a syringe, an IV bag, bottle, or vial of varying sizes and shapes. The containers can be glass or plastic (such as, polyethylene, polypropylene, polyvinyl chloride, or polypropylene-polyethylene blend).

In embodiments in which the opioid-free pharmaceutical compositions of the disclosure is contained in an IV bag, the size of the IV bag can be 25 mL, 50 mL, 100 mL, 150 mL, 200 mL, 250 mL, 300 mL, 400 mL, 500 mL, or 1000 mL.

In embodiments in which the opioid-free pharmaceutical compositions of the disclosure is contained in a syringe, the size of the syringe can be 1, 3, 5, 10, 12, 20, 25, 30, 50 or 60 cc.

In embodiments in which the opioid-free pharmaceutical compositions of the disclosure is contained in a vial, the size of the vial can be 2, 5, 10, 20, 25, 30, 50, 60, 100.

In embodiments in which the opioid-free pharmaceutical compositions of the disclosure is contained in a bottle, the size of the bottle can be 10, 20, 50, 100, 250, or 500.

4.6 Kits Comprising the Opioid-Free Compositions

The disclosure provides a kit of parts for performing any of the methods described herein. In one particular embodiment, the kit for an opioid-free pre-operative treatment comprises a magnesium salt, an alpha-2 agonist, and optionally a sodium channel inhibitor, an N-methyl-D-aspartate receptor (NMDA) inhibitor, and/or a corticosteroid. In certain embodiments, the kit comprises the individual components in separate containers or formulated together in one container as an opioid-free pre-operative composition.

In another particular embodiment, the kit for an opioid-free intra-operative composition comprises a magnesium salt, an alpha-2 agonist, a sodium channel inhibitor, and optionally an NMDA antagonist other than magnesium salt, and/or a beta-blocker. In certain embodiments, the kit comprises the individual components in separate containers or formulated together in one container as an opioid-free intra-operative composition.

In another particular embodiment, the kit for an opioid-free peri-operative composition comprises an opioid-free pre-operative composition of the disclosure and an opioid-free intra-operative composition of the disclosure. In certain embodiments, the kit further comprises a post-operative compositions of the disclosure.

In various embodiments, the kit of parts further comprises one or more additional agents herein described such as calcium channel inhibitor, Cox inhibitor, corticosteroid, GABA analogue, antidepressant, cannabidiol (CBD), and/or antiemetic agent as well as additional components identifiable by a skilled person.

In one embodiments, the kit of parts further comprises a reference standard.

In each of the embodiments described above, the container, which comprises the individual ingredients or the opioid-free compositions of the disclosure, may be a syringe, an IV bag, bottle, or vial of varying sizes and shapes. The containers can be glass or plastic (such as, polyethylene, polypropylene, polyvinyl chloride, or polypropylene-polyethylene blend).

In embodiments in which the opioid-free pharmaceutical compositions of the disclosure is contained in an IV bag, the size of the IV bag can be 25 mL, 50 mL, 100 mL, 150 mL, 200 mL, 250 mL, 300 mL, 400 mL, 500 mL, or 1000 ml.

In one embodiment, the kit of parts further comprises instructions for use. Instructions, for example, written or audio instructions, on paper or electronic support such as tapes, CD-ROMs, flash drives, or by indication of a Uniform Resource Locator (URL) including but not limited to YouTube tutorial, which contains a pdf copy of the instructions for carrying out the methods herein described, will usually be included in the kit. The kit can also contain, depending on the particular method used, other packaged reagents and materials. Further details concerning the identification of the suitable vehicles, carrier, or excipient of the compositions, and generally manufacturing and packaging of the kit, can be identified by the person skilled in the art upon reading of the disclosure.

The disclosure also provides a computer-based or mobile device-based application ("app") for use in the methods of the disclosure. The app can be devised to assist the operator (e.g., anesthesia provider) in providing the proper pre-operative, intra-operative, post-operative and/or peri-operative dosages of agents herein described to a patient, inclusive of instructions concerning the preparation of the related compositions and/or instructions for the related administration to the patient. The app can be devised to produce medication labels identifying the content of the desired admixture and/or patient and/or provider identifying information and/or date and time of preparation.

Further properties and characteristics of the disclosure will become more apparent hereinafter from the following detailed disclosure by way or illustration only with reference to the examples.

5. EXAMPLES

The compounds, materials, compositions, methods, and systems described herein are further illustrated in the following examples, which are provided by way of illustration and are not intended to limit the scope of the disclosed subject matter.

In particular, the following examples illustrate exemplary compositions and related methods and systems in accordance with the disclosure when the individual is a human patient. A person skilled in the art will appreciate the applicability and the necessary modifications to adapt the features described in detail in the present section, to additional compositions, methods and systems according to embodiments of the disclosure.

Example 1: Analgesia Protocol

The following materials were used in the Examples:
Dexmedetomidine Hydrochloride 200 mcg/2 ml.
Ketamine Hydrochloride 500 mg/10 ml.
Magnesium Sulfate 5 g/10 ml.
Esmolol Hydrochloride 100 mg/10 ml.
Lidocaine Hydrochloride 2%.
Dexamethasone Sodium phosphate 10 mg/l ml.
These materials are available from commercial suppliers, such as Hospira, West Ward, Accord, or Fresenius.
The Analgesia Protocol described below consists of (1) Pre-op at Home, (2) Pre-op on Ward, (3) Pre-op Hold IV Bolus Infusion over 15 min (4) Pre-op Blocks (5) Intra-op; (6) OFA Infusion Mixing Instructions, and (7) Regimen of Additional Agents.

Example 1.1: Pre-Op Regimen at Home

Duloxetine is given to a patient 1-2 weeks is prior to undergoing surgery with high risk of developing chronic pain, including, but not limited to, amputations, mastectomy, thoracotomy, inginal hernia repair, coronary artery bypass surgery, caesarean section, scoliosis correction surgery, bimalleolleolar ankle fracture surgery, Achilles' tendon repairs, thoracotomy, anterior lumbar surgery, abdominal surgery, breast cancer surgery, superficial melanoma resection, dental implant, laparoscopic hernia repair, hip fracture surgery and arthroplasty.

Example 1.2: Pre-Op Regimen on the Ward

The following medications were provided to the patient before surgery:
(1) Acetaminophen 1 gm PO or IV acetaminophen 1 gm IVPB priorto incision.
(2) Celecoxib 200-400 mg PO (unless allergy to sulfa) or meloxicam 15 mg.
(3) Pregabalin 50 mg—150 mg for neuropathic pain, with the dosage based on the following:
  A. 50 mg pregabalin if patient's age is equal to or over 65, or
  B. 75 mg pregabalin if patient's age is under 65,
  C. 150 mg if patient is routinely taking higher doses of Pregabalin priorto surgery.

Example 1.3 Pre-Op Hold Regimen of an Intra-Operative Composition of the Disclosure A bolus dose of an opioid-free pre-operative composition was prepared in a 10 mL syringe by combining the following:
6 mL magnesium sulfate (500 gm/mL),
1.5 mL dexamethasone (10 mg/mL),
0.3 mL dexmedetomidine (100 mcg/mL), and
2.2 mL 2% Lidocaine.
The pre-operative opioid-free composition was administered to the patient as 1 ml/10 kg Ideal Body Weight (IBW) over 15-30 min (which translates in terms of dosing to $Mg^{2+}$30 mg/kg, Dexmedetomidine 0.3 mcg/mg, Dexamethasone 0.15 mg/kg, and lidocaine 0.44 mg/kg).

When considering the pre-op loading dose, the following is taken into account:
Dexmedetomidine 0.3 mcg/kg. IV dexmedetomidine has a 15 minute peek effect. If the patient is adequately calm and/or sedate after using dexmedetomidine, the pre-operative benzodiazepines can be eliminated.
Magnesium sulfate 30 mg/kg,
Dexamethasone 0.15 mg/kg. Dexamethasone has a two hour onset time. Most preferred approach is to have it infused ample time before incision if using for mitigating inflammation/pain. For the purposes of opioid-free anesthesia, dexamethasone is used in higher dosing than what is commonly used in anesthesia for post-operative nausea and vomiting (PONV) prophylaxis.
Lidocaine filler to 10 mL volume. Once overage of medication discarded from syringe (weight bases dosage), the remainder of the volume is once again filled to 10 cc marker with 2% lidocaine and infused at 35 cc/hr. resulting in a 17 minutes long infusion, thus providing an ease of use of medication herein described.

Example 1.4: Administration of Pre-Op Blocks

When administering pre-operative blocks (e.g., nerve blocks or fascial plane blocks), dexamethasone and dexmedetomidine can be used as an additive. Alternatively, lysosomal bupivacaine or continuous nerve block catheter can be used when indicated.

Example 1.5: Intra-Op Regimen

The intra-operative phase can be described as the period when the patient is received in the area where the procedure is to be performed. The intra-operative phase ends when the patient is received in the post-operative care unit.
In the intra-operative phase, prior to induction the patient was given:
Ketamine 10-15 mg IVP 1-5 min prior to incision and/or intubation.
As soon as the pre-op infusion is complete and the patient is in the operating room, the patient was given an opioid-free intraoperative composition prepared as described in Example 1.6 below. Nitrous oxide was administered as:
50-70% of fresh gas low flow Nitrous Oxide Example 1.6: Preparation and Administration of an OFA Composition Below are the instructions for preparing an opioid-free intra-operative composition of the disclosure:
From 100 mL IV bag, remove 15 mL fluid
Add to the IV bag the following
  10 mL Lidocaine 2%,
  2 mL Magnesium sulfate (500 mg/mL)
  1.8 mL Esmolol (10 mg/ml)
  0.3 mL Dexmedetomidine (100 mcg/ml) (can add 0.1 mL more incrementally to modulate sympathetic nervous system)
  0.25 mL Ketamine (50 mg/ml).
Below are the instructions for administering the opioid-free intra-operative composition of the disclosure:
Run at rate of 1 mL/kg/hr IBW
IV Drip Dosages:
  Lido (1% or 2%) 2 mg/kg/hr IBW
  Magnesium sulfate 10 mg/kg/hr IBW Dexmedetomidine 0.3-1 mcg/kg/hr IBW depending how stimulating the procedure is for the patient Esmolol 3-10 mcg/kg/min IBW for OFA therapeutics or up to 300 mcg/kg/min IBW for mitigation of hypertension/tachycardia Ketamine 0.5 mg/kg IBW total dose for the duration of the case preferable Advocate for surgeon to infiltrate local anesthesia into the surgical site if not using a nerve block; preferably before incision.

Example 1.7: Regimen of Additional Agents

Below is a regimen of additional agents that were administrated during the intra and post-operative phase of the surgical procedure. The regimen of additional agents is intended to result in improved post-operative pain control for the surgical patient.

Acetaminophen 1 gm PO q8 hours-routine

Discontinue if consuming other acetaminophen containing medications, such as hydrocodone acetaminophen.

Celecoxib 100-200 mg PO q12 hours-routine

Pregabalin 50-150 mg qHS-routine,

For major surgical cases in which the patient is admitted to the hospital for post-operative care, on post-operative day 1, administer 10 mg of IV dexamethasone slowly over 10 minutes.

Continue duloxetine for 2 weeks after surgery for cases in which there is a high risk of developing chronic post-surgical pain syndrome.

Example 2: Infusion Ranges and Loading Doses

Selected exemplary infusion ranges (in concentration) and loading doses for agents are shown in Table 1 below.

TABLE 1

| Agents | Infusion Range | Loading Dose | Exemplary alternates | Notes |
|---|---|---|---|---|
| Lidocaine | 1-3 mg/kg/hr. | 0-2 mg/kg | Procaine Infusion: 1-6 mg/kg/hr or Prilocaine | Procaine has a higher incidence of allergic reactions as compared to other sodium channel blockers. Prilocaine causes methemoglobinemia. If the infusion was to be continued post-surgically for several days, the does would need to be reduced in order to avoid unwanted side effects such as local anesthesia toxicity. Peak serum levels occur 24 hours after medication administration. |
| Dexmedetomidine | 0.1-1 mcg/kg/hr | 0.1-1 mcg/kg | Clonidine Pre-op loading 1-2 mcg/kg Maintenance Infusion: 0.1-0.3 mcg/kg/hr | Veterinary medicine has several variations of alpha 2 Agonists such as Xylazine (Rompun) and a reversal agent Antisedan (atipamezole hydrochloride). There is no reversal agent available in human medicine |
| Ketamine | 0.1-0.5 mg/kg/hr | 0-0.5 mg/kg | | Patient should be monitored if receiving higher doses of dexmedetomidine and/or if they included ketamine. Both anesthetic medications cause sedation. Typically, a bolus of 15-25 mg ketamine is administered immediately before incision and/or 10-15 mg before intubation. Tiletamine which is a combination of Telazol and Zolazepram is available for use in veterinary medicine. |
| $Mg^{2+}$ Sulfate | 5-20 mg/kg/hr | 5-50 mg/kg | | If this combination were to be used as a continuous infusion post-operatively, serum $Mg^{2+}$ levels would need to be monitored and $Mg^{2+}$ titrated accordingly in order to avoid hypermagnesemia |
| Esmolol | 3-20 mcg/kg/min | N/A | | β-blockers obtund the sympathetic response therefore it would be appropriate to administer a bolus of this medication prior to a short duration stimulating events such as intubation or incision. It is inadvisable to include this medication in the loading does mixture given that the effect is |

TABLE 1-continued

| Agents | Infusion Range | Loading Dose | Exemplary alternates | Notes |
|---|---|---|---|---|
| | | | | very short acting and it may cause enhanced bradycardia and hypotension in the presence of dexmedetomidine absent of surgical stimulation. |
| Dexamethasone | | 0-0.2 mg/kg | Other glucocorticoids: Betamethasone, Methylprednisolone (Solu-medrol), Prednisone, Prednisolone, Triamcinolone, cortisol (Hydrocortisone/ Solu Cortef), cortisone | Cortisol and cortisone are short acting as compared to Dexamethasone. |

Example 3: Comparison of MuliMix and Exemplary OFA Composition 0211M

MuliMix, as described in Mulier, "Is opioid-free general anesthesia for breast and gynecological surgery a viable option?" Vol 32 No. 3, pp. 2567-262, June 2019 is compared to preemptive analgesia OFA composition as described herein and shown in the Table 2 below.

TABLE 2

Comparison of MuliMix and Exemplary OFA composition of the disclosure

| | MuliMix | | | | | |
|---|---|---|---|---|---|---|
| Sequence | Timing | Dosing | Notes | Timing | Dosing | Notes |
| | | | | Preemptive Analgesia (OFA) of the disclosure | | |
| Premedication | Pre-Op | Clonidine 150 mcg; or Pregabalin 150 mg; or Gabapentin 300 mg PO | Optional in protocol | Ideally administered 1-2 hrs. before surgery. Can be given immediately before surgery. | Acetaminophen 1 g PO or IV; and Celecoxib 400 mg PO or Meloxicam 15 mg PO; and Pregabalin 50-150 mg PO or Gabapentin 300-900 mg PO | Use for patients expected to have post-operative pain; Hold Acetaminophen for liver problem; Hold NSAIDs for renal issues caution when using with Celecoxib in the presence of CAD, Hold Celecoxib for sulfa allergy. Reduce Pregabalin/gabapentin for pts >65 y/o |
| | | | | Pre-operative Opioid-Free Composition of the Disclosure | | |
| Pre--Induction Loading Dose | 15-30 min before start; not less than 10 min. before induction | Dexmedetomidine 0.25 mcg/kg Max dose 20 mcg | "Dexdor load" Pt. must be on monitors. | Ideally 20-30 min. before start. Greater than 60 min would require an additional dexmedetomidine loading dose if pt. no longer sedate/state of anxiolysis. Infuse | 1 cc/10 kg IBW = $Mg^{2+}$ 30 mg/kg Dexamethasone 0.15 mg/kg Dexmedetomidine 0.3 mcg/kg Lidocaine 0.44 mg/kg (filler) Eliminate Versed | Lidocaine is used as a filler in the loading dose. The IBW of the patient is calculated, determine how many cc's of the mix is required for the patient, discard the excess and fill the remainder of the 10 ml syringe with Lidocaine. Lidocaine dosing not to exceed >2 mg/kg. If additional fluid need, use 0.9% |

TABLE 2-continued

| Comparison of MuliMix and Exemplary OFA composition of the disclosure | | | | | | |
|---|---|---|---|---|---|---|
| | MuliMix | | | | | |
| Sequence | Timing | Dosing | Notes | Timing | Dosing | Notes |
| | | | | desired dose over ~15 min (infusion can take longer but ideally not under 10 minutes) | | normal saline or comparable intravenous isotonic fluid solution |
| Loading Dose Mixture | 5 ml dexmedetomidine (0.4 mcg/ml) = 20 mcg | | | 6 ml $Mg^{2+}$ (500 mg/ml) = 3 gm<br>1.5 ml Dexamethasone (10 mg/ml) = 15 mg<br>0.3 ml Dexmedetomidine (100 mcg/ml) = 30 mcg<br>2.2 ml 2% Lidocaine (fill to 10 cc) = 44 mg | | |
| Induction | During induction of Anesthesia | 1 ml/10 kg of the MuliMix =<br>Dexmedetomidine: 0.1 mcg/kg<br>Lidocaine 1 mg/kg<br>Ketamine 0.1 mg/kg | Continue induction with Propofol, give paralytic if needed. Consider/optional:<br>Dexamethasone 10 mg<br>Droperidol 0.625-1.2 mg<br>$Mg^{2+}$ 40 mg/kg<br>Ketamine 25-50 mg additional dose before incision. | | | Usual induction agents such as propofol, etomidate, or ketamine. Consider adding small doses of ketamine (10-15 mg) or esmolol (30-50 mg) if intubating. |
| | | | | Intra-operative Opioid-Free Composition of the disclosure | | |
| Maintenance of Anesthesia | After induction and throughout surgery; reduce by ½ 15 min. before the end of sx. | 1 ml/10 kg/hr. =<br>Dexmedetomidine: 0.1 mcg/kg/hr.<br>Lidocaine 1 mg/kg/hr.<br>Ketamine 0.1 mg/kg/hr. | Sevo or propofol infusion as usual | Start as soon as pt. is situated in the operaing room ideally prior to induction. Stop infusion ~20 minutes before end of surgery. | 1 ml/kg/hr. (IBW) =<br>*Dexmedetomidine 0.3 mcg/kg/hr.<br>Lidocaine 2 mg/kg/hr.<br>Ketamine 0.25 mg/kg/hr.<br>$Mg^{2+}$ 10 mg/kg/hr.<br>Esmolol 3 mcg/kg/min | *each additional 0.1 ml of dexmedetomidine added to the bag will increase the concentration by 0.1 mcg/kg/hr. |
| Mixture Content | Combine the following in a 50 ml syringe:<br>50 mcg Dexmedetomidine (Dexdor) (0.5 cc of standard 100 mcg/ml solution or 12.5 cc from 4 mcg/ml.<br>50 mg Ketamine (Ketalar) or 25 mg S-Ketamine)<br>500 mg Lidocaine (linisol) (25 ml of standard 2% solution)<br>NaCl up to total 50 ml | | | 100 ml IV Bag, remove & discard 15 ml fluid; Add the following<br>10 ml 2% Lidocaine = 200 mg<br>2 ml Magnesium salt (500 mg/ml) = 1 Gm<br>1.8 ml Esmolol (10 mg/ml) = 18 mg<br>*0.3 ml Dexmedetomidine (100 mg/ml) = 30 mcg<br>0.5 ml Ketamine (50 mg/ml) = 25 mg | | |
| PACU | In recovery unit | 0.5 ml/10 kg/hr.<br>Dexmedetomidine 0.05 mcg/kg/hr.<br>Lidocaine 0.5 mg/hg/hr.<br>Ketamine 0.05 mg/kg/hr. | | | | This composition has infrequently been used use in the post-operative period. The composition is sedating which counters the desired wakeful state during the recovery period. For pain management or sedation in the post-operative period, consider titrating the rate of infusion to effect. |

TABLE 2-continued

Comparison of MuliMix and Exemplary OFA composition of the disclosure

| | MuliMix | | | | | |
|---|---|---|---|---|---|---|
| Sequence | Timing | Dosing | Notes | Timing | Dosing | Notes |
| After PACU | ICU, Ward, Day Clinic, Home | 0.5 ml/10 kg/hr. = Dexmedetomidine 0.05 mcg/kg/hr. Lidocaine 0.5 mg/hg/hr. Ketamine 0.05 mg/kg/hr. If needed PCA bolus of 1 ml (lockout 15 min.) Paracetamol IV/PO NSAIDs PO Morphine IV/PO/SL as rescue | | | | As above. Continue non-opioid medication regime including: Acetaminophen 1 Gm q8 hrs, Celecoxib 200 mg q12 hrs, Pregabalin 50-150 mg qHS |
| Add. Notes | All doses can be adjusted if needed (age effect more important than weight!<br>Consider 0.5-1 ml/10 kg bolus of the mixture just before surgery if tachycardia<br>For obese patients base doses on IBW instead of TBW<br>For short procedure use no maintenance infusion<br>Have metoprolol, nicardipine, ephedrine, phenylephrine or comparable available | | | For very short procedures (30 minutes or less) use the loading does but use low dose boluses at the begging of case instead of starting an infusion.<br>Pt. response to medication and surgery may vary, adjust the other anesthetic medications first if pt. hypotensive and "too deep." It is common to see reductions of other anesthetic agents by greater than 50%. On average, the continuous infusion takes 20 minutes until the onset is observed. If the patient demonstrates inadequate sympathetic outflow control after 20 minutes of infusion, increased the dexmedetomidine by 0.1 mcg/kg/hr. (add 0.1 ml to the bag for each incremental increase). See precaution considerations for medication to determine if some components need to be adjusted or eliminated from the composition. | | |

TABLE 3

Comparison of MuliMix and an Exemplary OFA Composition of the Disclosure[1]

| | | | MuliMix | | | Preemptive Analgesia (OFA) | | |
|---|---|---|---|---|---|---|---|---|
| Pt. weight | Wt. Variance Examples | | 45 kg | 70 kg | 100 kg | 45 kg | 70 kg | 100 kg |
| Pre-Induction | Dexmedetomidine | ml of mix | 2.8 | 4.3 | 5 | 4.5 | 7 | 10 |
| Loading Dose | | mcg | 11.25 | 17.5 | 20 (max) | 13.5 | 21 | 30 (no max) |
| | $Mg^{2+}$ sulfate | gm | | | | 1.35 | 2.1 | 3 |
| | Dexamethasone | mg | | | | 6.75 | 10.5 | 15 |
| | Lidocaine | mg | | | | 19.8 | 30.8 | 44 |
| Induction | Mix | ml | 4.5 | 7 | 10 | | | |
| Loading | Dexmedetomidine | mcg | 4.5 | 7 | 10 | | | |
| Dose | Lidocaine | mg | 45 | 70 | 100 | | | |
| | Ketamine | mg | 4.5 | 7 | 10 | | | |
| Anesthesia | Mix | ml/hr | 4.5 | 7 | 10 | 45 | 70 | 100 |
| Maintenance | Dexmedetomidine | mcg/hr | 4.5 | 7 | 10 | 13.5 | 21 | 30 |
| | Lidocaine | mg/hr | 45 | 70 | 100 | 90 | 140 | 200 |
| | Ketamine | mg/hr | 4.5 | 7 | 10 | 11.25 | 17.5 | 25 |
| | $Mg^{2+}$ sulfate | mg/hr | | | | 450 | 700 | 1000 |
| | Esmolol | mcg/hr | | | | 8.1 | 12.6 | 18 |
| PACU | MuliMix | ml/hr | 2.25 | 3.5 | 5 | | | |
| | Dexmedetomidine | mcg/hr | 2.25 | 3.5 | 5 | | | |
| | Lidocaine | mg/hr | 22 | 35 | 50 | | | |
| | Ketamine | mg/hr | 2.25 | 3.5 | 5 | | | |
| After PACU | MuliMix | ml/hr | 2.25 | 3.5 | 5 | | | |
| | Dexmedetomidine | mcg/hr | 2.25 | 3.5 | 5 | | | |
| | Lidocaine | mg/hr | 22 | 35 | 50 | | | |
| | Ketamine | mg/hr | 2.25 | 3.5 | 5 | | | |

[1]Examples of dose and volume differences based on patient weight variance

Differences between the ingredients of the MuliMix compositions and Exemplary OFA composition are evident. The OFA preemptive analgesia composition of the disclosure has significantly higher dosing than MuliMix and it can be used in the pre and intra-operative periods. There is a dose responsive curve to dexmedetomidine, lidocaine and ketamine. The higher the dose, the greater the sedation effect. The OFA preemptive analgesia composition with much higher dosing of the disclosure would result in a more significant reduction of other anesthetic agents such as a propofol infusion or anesthetic gasses such as sevoflurane, desflurane or isoflurane.

The OFA preemptive analgesia protocol has a pre-operative loading dose and an intra-operative infusion. These two formulas have different agents and concentrations intended for separate and distinct purposes. The loading dose is intended to rapidly increase the plasma levels of the OFA agents so that it's therapeutic onset is much quicker than with the intra-operative infusion alone. This differs from MuliMix protocol, which uses the same concentration for each step of the sequence with the exception of the dexmedetomidine loading dose (see table 2). The loading dose in protocol described herein will be used for out-patient surgeries/shorter cases in which the continuous infusion is excluded. In place of the infusion for short cases, incremental doses are given of some of the medications typically frontloading with dexmedetomidine 10 mcg boluses, ketamine, and lidocaine which is commonly mixed with propofol to prevent the sensation of burning at the IV site when propofol is administered. $Mg^{2+}$ is optionally excluded as the loading dose alone would be sufficient to cover a short case without continuing an infusion. MuliMix does not expressly include $Mg^{2+}$ or Dexamethasone Sodium phosphate in the mixture but suggests considering using these components as part of the anesthetic. Pre-meds are also on the list to consider but are not specified as a requirement to the protocol unlike the OFA Protocol described herein.

If $Mg^{2+}$ salt is loaded as an adjunct to the MuliMix protocol it is instructed to be given as a hand delivered IV push (over a few seconds). When this was followed, even splitting the dose into more than one bolus, substantial hypotension was observed, especially when under anesthesia/at induction. It is not ideal to administer a medication in a method that would potentiate hypotension after induction. There is generally a lag between induction of anesthesia (putting the patient to sleep) and stimulation via surgery incision. This period is often associated with hypotension as the patient is given a large dose of anesthetic, in order to insert a breathing device, but there is no further stimulation until incision is made. During this time the surgical team is usually positioning the patient, sterilizing the area, placing drapes, preparing the instrumentation, etc. It is an undesirable time to give an agent that has a propensity to potentiate hypotension. It is another reason opioid-free anesthesia is superior to opioid based anesthesia. In an opioid based anesthesia, fentanyl, for example, is routinely given at the induction of anesthesia before inserting an airway. Fentanyl interacts synergistically with other medications, such as versed, to potentiate hypotension during this lull of activity and also causes the patient not to breathe on their own for several minutes until the ETCO2 increases enough to drive breathing. This results in extra work for the provider by requiring manually ventilating if the patient is not being mechanically ventilated and possibly safety concerns if the airway cannot be secured and is not patent.

Example 4: Comparison of McLott Mix and Exemplary OFA Composition

McLott Mix, as described on the world wide web at mclottmix.com, is compared to preemptive analgesia OFA composition of the disclosure and shown in the Table 4 below.

TABLE 4

Comparison of McLott Mix and Exemplary OFA Composition of the Disclosure

| | McLott Mix | | | | | |
|---|---|---|---|---|---|---|
| Sequence | Timing | Dosing | Notes | Timing | Dosing | Notes |
| | | | | Preemptive Analgesia (OFA) of the disclosure | | |
| | | | No pre-op medications indicated | Ideally administered 1-2 hrs. before surgery. Can be given immediately before surgery. | Acetaminophen 1 g PO or IV; and Celecoxib 400 mg PO or Meloxicam 15 mg PO; and Pregabalin 50-150 mg PO or Gabapentin 300-900 mg PO | Use for patients expected to have post-operative pain; Hold Acetaminophen for liver problem; Hold NSAIDs for renal issues caution when using with Celecoxib in the presence of CAD, Hold Celecoxib for sulfa allergy. Reduce Pregabalin/gabapentin for pts >65 y/o |
| | | | | Pre-operative Opioid-Free Composition of the Disclosure | | |
| | | | No pre-op medications indicated | Ideally 20-30 min. before start. Greater than 60 min would require an additional dexmedetomidine loading dose if pt. no longer sedate/state of anxiolysis. Infuse | 1 cc/10 kg IBW = $Mg^{2+}$ 30 mg/kg Dexamethasone 0.15 mg/kg Dexmedetomidine 0.3 mcg/kg Lidocaine 0.44 mg/kg (filler) Eliminate Versed | Lidocaine is used as a filler in the loading dose. The IBW of the patient is calculated, determine how many cc's of the mix is required for the patient, discard the excess and fill the remainder of the 10 ml syringe with Lidocaine. Lidocaine dosing not to exceed >2 mg/kg. If additional fluid need, use 0.9% normal saline or comparable intravenous isotonic fluid solution |

TABLE 4-continued

| Comparison of McLott Mix and Exemplary OFA Composition of the Disclosure | | | | | | |
|---|---|---|---|---|---|---|
| | McLott Mix | | | | | |
| Sequence | Timing | Dosing | Notes | Timing | Dosing | Notes |
| | | | | desired dose over ~15 min (infusion can take longer but ideally not under 10 minutes) | | |
| Loading Dose Mixture | | | | 6 ml $Mg^{2+}$ (500 mg/ml) = 3 gm<br>1.5 ml Dexamethasone (10 mg/ml) = 15 mg<br>0.3 ml Dexmedetomidine (100 mcg/ml) = 30 mcg<br>2.2 ml 2% Lidocaine (fill to 10 cc) = 44 mg | | |
| Induction | During induction of Anesthesia | OFA Induction Ketamine & Dexmedetomidine Mixture 0.25-0.5 ml/10 kg.<br>Lidocaine 2 mg/kg<br>Magnesium 0.5-1 g bolus<br>Toradol 15 mg<br>Nubain 5-10 mg | Divide mixture into several small dosages from preop to OR. Continue induction with Propofol. Amounts based on IBW or AdjBW | | | Usual induction agents such as propofol, etomidate, or ketamine. Consider adding small doses of ketamine (10-5 mg) or esmolol (30-50 mg) if intubating. |
| Induction Mixture | Ketamine 10 mg/Dexmedetomidine 10 mcg/ml | | | | | |
| | | | | Intra-operative Opioid-Free Composition of the disclosure | | |
| Maintenance of Anesthesia | After induction and throughout surgery; reduce by ½ 15 min. before the end of sx. | 0.5 ml/kg/hr (IBW or AdjBW) =<br>Dexmedetomidine: 0.4 mcg/kg/hr.<br>Lidocaine 2 mg/kg/hr.<br>Ketamine 5 mcg/kg/hr<br>Mg 10 mg/kg/hr | Run infusion until closure begins Larger infusion may be made in 100 mL bag after removing 20 mL of volume from bag and adding double the amount of medications listed above | Start as soon as pt. is situated in the operating room ideally prior to induction. Stop infusion ~20 minutes before end of surgery. | 1 ml/kg/hr. (IBW) =<br>*Dexmedetomidine 0.3 mcg/kg/hr.<br>Lidocaine 2 mg/kg/hr.<br>Ketamine 0.25 mg/kg/hr.<br>$Mg^{2+}$ 10 mg/kg/hr.<br>Esmolol 3 mcg/kg/min | *each additional 0.1 ml of dexmedetomidine added to the bag will increase the concentration by 0.1 mcg/kg/hr. |
| Mixture Content | Syringe (50 ml)<br>Lidocaine 2% 10 ml, Ketamine 30 mg, Dexmedetomidine 40 mcg, Magnesium 1 gm, Fill rest of syringe with IVF<br>NS 100 ml bag remove 20 ml<br>Inject Lido 2% 20 ml, Ketamine 60 mg, Magnesium 2 gm, and Dexmedetomidine 80 mcg into bag | | | 100 ml IV Bag, remove & discard 15 ml fluid; Add the following<br>10 ml 2% Lidocaine = 200 mg<br>2 ml Magnesium salt (500 mg/ml) = 1 Gm<br>1.8 ml Esmolol (10 mg/ml) = 18 mg<br>*0.3 ml Dexmedetomidine (100 mg/ml) = 30 mcg<br>0.5 ml Ketamine (50 mg/ml) = 25 mg | | |
| PACU | In recovery unit | | | | | This composition has infrequently been used use in the post-operative period. The composition is sedating which counters the desired wakeful state during the recovery period. For pain management or sedation in the post-operative period, consider titrating the rate of infusion to effect. |

TABLE 4-continued

| Comparison of McLott Mix and Exemplary OFA Composition of the Disclosure | | | | | | |
|---|---|---|---|---|---|---|
| | McLott Mix | | | | | |
| Sequence | Timing | Dosing | Notes | Timing | Dosing | Notes |
| After PACU | ICU, Ward, Day Clinic, Home | Acetaminophen 650 mg-1 GM q6 hrs Ibuprofen 600 mg q6 hrs or Aleve 440 mg (2 pills) every 12 hours (morning and night) a. If taking ibuprofen 600 mg, either take acetaminophen and ibuprofen together q6 hrs, or alternate taking either ibuprofen or acetaminophen Q3 hrs If pain score is >5 take ordered pain pill skip next dose of acetaminophen Avoid taking >4 gm of acetomenophen in 24 hrs | | | | As above. Continue non-opioid medication regime including: Acetaminophen 1 Gm q8 hrs, Celecoxib 200 mg q12 hrs, Pregabalin 50-150 mg qHS |
| Add. Notes | | | | For very short procedures (30 minutes or less) use the loading does but use low dose boluses at the begging of case instead of starting an infusion. Pt. response to medication and surgery may vary, adjust the other anesthetic medications first if pt. hypotensive and "too deep." It is common to see reductions of other anesthetic agents by greater than 50%. On average, the continuous infusion takes 20 minutes until the onset is observed. If the patient demonstrates inadequate sympathetic outflow control after 20 minutes of infusion, increased the dexmedetomidine by 0.1 mcg/kg/hr. (add 0.1 ml to the bag for each incremental increase). See precaution considerations for medication to determine if some components need to be adjusted or eliminated from the composition. | | |

Differences between McLott Mix and an exemplary OFA Composition of the Disclosure are evident. Unlike the opioid-free pre-operative composition of the disclosure, McLott does not provide any pre-operative oral medications. Rather, McLott Mix is only referred to as being an intra-operative composition. McLott's OFA induction is not said to be required or an integral part of the McLott method. And, there does not seem to be a protocol in the same way as that of the method of the disclosure.

In the McLott Mix, the loading dose of $Mg^{2+}$ is not weight-based and as such, results in an underdosing for most adult patients. In contrast, in some embodiments, the opioid-free intra-operative composition and/or methods of it use loads $Mg^{2+}$ with a specific weight-based dose that is known to have a clinical effect.

In addition, Nalbuphine (Nubain) is listed as part of the McLott's OFA Induction. Nalbuphine is a synthetic opioid agonist-antagonist analgesic of the phenanthrene series. It binds to mu, kappa, and delta receptors and has equal analgesic potency to morphine. There have been reports of drug abuse and dependence associated with nalbuphine among healthcare providers, patients, and members of the general public (see drugs.com/pro/nubain.htm & https://app.plumbs.com/drug-monograph/UsBzNf0XCMPROD?source=search&searchQuery=Nubain on the world wide web). In contrast, the opioid-free compositions of the disclosure and accompanying methods are completely opioid-free.

Another difference between McLott and the methods of the disclosure is in the timing of dexmedetomidine administration. In McLott, dexmedetomidine is administered at induction and not pre-operatively. If the dexmedetomidine is not given in the pre-operative holding area, there is no additional benefit of anxiolysis in the pre-operative phase. Additionally, giving dexmedetomidine as a bolus at induction is known to cause transient hypertension followed by hypotension This timing is particularly problematic. Immediately after induction, the airway placement procedure (intubation) can cause transient hypertension and tachycardia. Once the airway is placed, it is very common for a period of pronounced hypotension to occur until the start of surgery. If dexmedetomidine is given as a bolus at induction, there is a high probability of exacerbating these problematic hemodynamic extremes.

The McLott method does not include a corticosteroid as a pre-op or induction medication. In contrast, the opioid-free pre-operative compositions and accompanying methods of the disclosure include a corticosteroid to aid in decreasing the inflammatory response and post-operative pain.

McLott's Mix intra-operative infusion is approximately twice as concentrated as the opioid-free intra-operative composition of the disclosure. McLott's instructions are to give 0.5 cc/kg vs 1 ml/kg. This does add one additional mathematical step to the administration process. The dexmedetomidine dosing is higher in the McLott mix and therefore would be more likely to cause side effects of hypotension and bradycardia as compared to the opioid-free intra-operative composition of the disclosure. Beneficially, infusion of the opioid-free intra-operative composition of the disclosure starts on the lower end dosing of dexmedetomidine and thus provides the option of increasing the dexmedetomidine dosing if indicated by the patient response to surgery. The opioid-free intra-operative composition of the disclosure also uses a low dose short acting beta blocker that adds an additional pathway to block pain, unlike the McLott mix. Beta blockers are known to decrease neuroendocrine stress response resulting in a reduction in pro-inflammatory cytokinin's and NMDA receptor activation.

Example 5: Preparation of an Exemplary Pre-Operative OFA Composition of the Disclosure in a Loading Dose Syringe A pre-operative OFA composition was prepared by mixing of the individual component medications in a syringe. The individual medications include lidocaine (44 mg/2.2 mL of 2%), magnesium sulfate (3 gm/6 ml of 50%), dexmedetomidine (30 mcg/0.3 ml of 10%), and dexamethasone (15 mg/1.5 ml of 1%) to a final volume of 10 mL in syringe.

The individual component medications used in Example 5 are shown in FIG. 10.

Example 6: Preparation of an Exemplary Intra-Operative OFA Composition of the Disclosure Selected exemplary infusion range in concentration and doses for agents in a 100 mL IV bag are shown, for example, in the table shown in FIG. 11.

An intra-operative OFA composition was prepared by mixing of the individual component medications in a 100 mL IV bag. The individual component medications in the intra-operative OFA composition include lidocaine (200 mg) magnesium sulfate (1 g), dexmedetomidine (0.3 mcg), ketamine (25 mg), and esmolol HCl (18 mg) to a final volume of 100 mL in the IV bag.

The intra-operative OFA composition was infused at rate of 1 cc/kg/hr patient IBW.

The individual component medications used in Example 5 are shown in FIG. 11.

Example 7: Exemplary Doses and Ranges of Exemplary OFA Compositions of the Disclosure For a 50 kg patient administer the compositions described below.

Pre-op Loading-Lowest doses of most concentrated compositions (excluding optional components)

250 mg (0.5 ml of 50%) magnesium sulfate (5 mg/kg)

5 mcg (0.05 ml of 10%) dexmedetomidine (0.1 mcg/kg)

Dexamethasone—optional

Ketamine—optional

Lidocaine—optional

Intra-op Infusion-Most Concentrated Infusion Possible-(excluding optional components and lowest possible doses of all components except for the component being examined)

250 mg (0.5 ml 50%) magnesium sulfate (5 mg/kg/hr)

25 mg (0.65 ml of 4%) Lidocaine (0.5 mg/kg/hr)

5 mcg (0.05 ml of 10%) Dexmedetomidine (0.1 mcg/kg/hr)

Ketamine—optional as described herein

Esmolol—optional as described herein

The following calculations can be performed to identify maximum concentrations for the various agents.

Magnesium Sulfate Calculations for Max Concentrations

Pre-Op Loading Dose:

Min: 1 mg/ml

Max: 500 mg/ml. Since the only other absolute medication is dexmedetomidine which is almost negate, the 500 mg/ml will be a little higher than actual but within a reasonable range.

Intra-Op Infusion:

Min: 1 mg/ml

Max: ~370 mg/ml (294 gm/ml)

50 kg pt (Most Concentrated Mm++ Infusion)

500 mg (1 ml of 50%) magnesium sulfate (20 mg/kg/hr)—Highest dose for magnesium sulfate 25 mg (0.65 ml of 4%) lidocaine (0.5 mg/kg/hr)

5 mcg (0.05 ml of 10%) dexmedetomidine (0.1 mcg/kg/hr)

Ketamine—optional as described herein

Esmolol—optional as described herein

=2.7 ml total volume 500 mg/2.7 ml=370 mg/ml

Dexmedetomidine Calculations for Max Concentrations

Pre-Op Loading Dose:

Min: 0.01 mcg/ml

Max: 50 mcg/ml 50 kg pt (Most Concentrated Dexmedetomidine Loading Dose)

250 mg (0.5 ml 50%) Mg+ (5 mg/kg)

50 mcg (0.5 ml of 10%) dexmedetomidine (1 mcg/kg)—Max loading dose

=1 ml total volume 50 mcg/1 ml=50 mcg/ml

Intra-Op Infusion:

Min: 0.01 mcg/ml

Max: 30 mcg/ml 50 kg pt (Most concentrated Dexmedetomidine Infusion Dose)

250 mg (0.5 ml 50%) magnesium sulfate (5 mg/kg/hr)

25 mg (0.65 ml of 4%) lidocaine (0.5 mg/kg/hr)

50 mcg (0.5 ml of 10%) dexmedetomidine (1 mcg/kg/hr)—Max Infusion Dose

Ketamine—optional as described

Esmolol—optional as described

=1.65 ml 50 mcg/1.65 ml=30 mcg/ml

Lidocaine Calculations for Max Concentrations

Pre-Op Loading Dose:

Min: 0 mg/ml—This should be ok since it is an optional agent for loading dose

Max: 35 mg/ml 50 kg pt (Most Concentrated Lidocaine Loading Dose)

250 mg (0.5 ml of 50%) Mg+ (5 mg/kg)

5 mcg (0.05 ml of 10%) Dexmedetomidine (0.1 mcg/kg)

Dexamethasone—optional

Ketamine—optional 100 mg (2.5 ml of 4%) Lidocaine (2 mg/ml)

=3.05 ml 100 mg/3.05 ml=33 mg/ml

Intra-Op Infusion:

Min: 0.1 mg/ml 50 kg pt (Least Concentrated Lidocaine Max Dose on Everything Else-Infusion)-Could also include lesser concentrations of original vials but did not. Rounded down.

500 mg (1 ml 50%) magnesium sulfate (10 mg/kg/hr)
25 mg (0.65 ml of 4%) lidocaine (0.5 mg/kg/hr)
50 mcg (0.5 ml of 10%) dexmedetomidine (1 mcg/kg/hr)
25 mg (0.5 ml of 5%) ketamine (0.5 mg/kg/hr)
900 mg (90 ml of 1%) esmolol (300 mcg/kg/min)
=92.65 ml
25 mg/92.65 ml=0.27 mg/ml Max: 35 mg/ml 50 kg pt (Max Concentrated Lidocaine Infusion Dose-Lowest Dose on Everything Else)
250 mg (0.5 ml 50%) magnesium sulfate (5 mg/kg/hr)
150 mg (3.75 ml of 4%) lidocaine (3 mg/kg/hr)
5 mcg (0.05 ml of 10%) dexmedetomidine (0.1 mcg/kg/hr)
Ketamine—optional as described
Esmolol—optional as described
=4.3 ml
150 mg/4.3 ml=34.88 mg/ml Ketamine Calculations for Max Concentrations Pre-Op Loading Dose:

Min: 0 mg/ml-Optional

Max: 35 mg/ml 50 kg pt (Max Concentrated Ketamine Loading Dose-Lowest Dose on Everything Else)
250 mg (0.5 ml of 50%) magnesium sulfate (5 mg/kg)
5 mcg (0.05 ml of 10%) dexmedetomidine (0.1 mcg/kg)
Dexamethasone—optional
25 mg (0.25 ml of 10%) ketamine (0.5 mg/kg)
Lidocaine—optional
=0.8 ml
25 mg/0.8 ml=31.25 mg/ml Intra-Op Infusion:

Min: 0 mg/ml-optional

Max: 20 mg/ml 50 kg pt (Max Concentrated Lidocaine Infusion Dose-Lowest Dose on Everything Else)
250 mg (0.5 ml 50%) magnesium sulfate (5 mg/kg/hr)
25 mg (0.65 ml of 4%) lidocaine (0.5 mg/kg/hr)
5 mcg (0.05 ml of 10%) dexmedetomidine (0.1 mcg/kg/hr)
25 mg Ketamine (0.25 ml of 10%) ketamine (0.5 mg/kg/hr)
Esmolol—optional as described
=1.45 ml
25 mg/1.45=17.24 mg/ml Esmolol Calculations for Max Concentrations Pre-Op Loading Dose:

If a different β-Blocker was used with slow onset or in an oral instead of an IV rout adding this pre-op could be considered.

Intra-Op Infusion:

Min: 0 mg-optional

Max: 20 mg/ml—This higher dosing of esmolol should be administered as a separate drip reflected in this concentration. The higher doses are for hypertensive emergencies and are outside of the scope of this invention (purpose other than analgesia). 250 mg (0.5 ml 50%) magnesium sulfate (5 mg/kg/hr)

25 mg (0.65 ml of 4%) lidocaine (0.5 mg/kg/hr)
5 mcg (0.05 ml of 10%) dexmedetomidine (0.1 mcg/kg/hr)
ketamine—optional as described
900 mg (45 ml of 2%) esmolol (300 mcg/kg/min)
=46.2 ml
900 mg/46.2 ml=19.48 mg/ml Dexamethasone Calculations for Max Concentrations Pre-Op Loading Dose:

Min: 0 mg/ml-optional

Max: 10 mg/ml 50 kg pt (Max Concentrated Dexamethasone Loading Dose-Lowest Dose on Everything else)
250 mg (0.5 ml of 50%) magnesium sulfate (5 mg/kg)
5 mcg (0.05 ml of 10%) dexmedetomidine (0.1 mcg/kg)
10 mg (0.5 ml of 2%) dexamethasone (0.2 mg/kg)
Ketamine—optional
Lidocaine—optional
=1.05 ml
10 mg/1.05 ml=9.52 mg/kg

Example 9: Preparation of an Exemplary Opioid-Free Pre-Operative Composition of the Disclosure An exemplary pre-operative composition in accordance with the disclosure is reported in Table 5.

TABLE 5

| Pre-op Medication for Bolus | Vial Concentration | Vial Units | Min Dose Amount (Units/kg) | Max Dose Amount (Units/kg) | Units |
|---|---|---|---|---|---|
| Dexmedetomidine | 100 | mcg/ml | 0.1 | 1 | mcg/kg |
| Magnesium | 500 | mg/ml | 5 | 30 | mg/kg |
| Dexamethasone | 20 | mg/ml | 0 | 0.2 | mg/kg |
| Ketamine | 50 | mg/ml | 0 | 0.5 | mg/kg |
| Lidocaine | 40 | mg/ml | 0 | 2 | mg/kg |
| Normal Saline | 0.9 | % | 0 | 2 | Filler |
| Total Volume | | | | | |
| Rate | 40 ml/hr (10 ml volume over 15 minutes) | | | | |

Example 10: Minimum and Maximum Doses for Opioid-Free Pre-Operative Compositions of the Disclosure An exemplary minimum and maximum dose for pre-emptive pre-operative composition in a bolus form is provided in the following Table 6.

TABLE 6

| Pre-op Medication for Bolus | Min Dose in ml | Max Dose in ml |
|---|---|---|
| Dexmedetomidine | 0.1 | 1 |
| Magnesium | 1 | 6 |
| Dexamethasone | 0 | 1 |
| Ketamine | 0 | 1 |
| Lidocaine | 0 | 5 Lido to be given as a separate loading dose if total loading dose volume >10 ml |
| Normal Saline | 8.9 | 0: If lido given as a separate loading dose add 1 ml NS to other 9 ml of contents for a total volume of 10 ml |
| Total Volume Rate | 10 | 10 + 5 |

Example 11: Doses for Opioid-Free Pre-Operative Compositions of the Disclosure

Exemplary doses for pre-emptive Pre-operative composition in a bolus form is provided in Table 7.

TABLE 7

| Pre-op Medication for Bolus | Minimum Units per ml of mix | Maximum Units per ml of mix | Dose | Actual Amount (Total) Administered | Units | Dose, ml Volume |
|---|---|---|---|---|---|---|
| Dexmedetomidine | 1 | 10 | 0.3 | 30 | Mcg | 0.3 |
| Magnesium | 50 | 300 | 30 | 3000 | Mg | 6 |
| Dexamethasone | 0 | 2 | 0.15 | 15 | Mg | 0.75 |
| Ketamine | 0 | 5 | 0.01 | 1 | Mg | 0.02 |
| Lidocaine | 0 | 40 (4%) | 0.586 (2%) | 58.6 (2%) | Mg | 2.93 |
| Normal Saline | 0 | 20 | 0 | 0 | None | |
| Total Volume Rate | | | | | | 10 |

Example 12: Minimum and Maximum Doses for Opioid-Free Intra-Operative Compositions of the Disclosure Exemplary minimum and maximum doses in Units/kg/hr for an exemplary opioid-free intra-operative composition of the disclosure are provided in Table 8. This opioid-free intra-operative composition is administered as a continuous drip.

TABLE 8

| Intra-op Medication Continuous Drip | Vial Concentration | Vial Units | Min Dose Amount (Units/kg/hr) | Max Dose Amount (Units/kg/hr) | Units |
|---|---|---|---|---|---|
| Lidocaine 2% | 20 | mg/ml | 0.5 | 3 | mg/kg/hr |
| Magnesium | 500 | mg/ml | 5 | 10 | mg/kg/hr |
| Dexmedetomidine | 100 | mcg/ml | 0.1 | 1 | mcg/kg/hr |
| Esmolol | 20 | mg/ml | 3 | 300 | mcg/kg/min |
| Ketamine | 50 | mg/ml | 0.1 | 0.5 | mg/kg/hr |

Additional agents are administered, as needed, as a continuous drip, and comprise lidocaine 400 and/or ketamine 100 mg/mL.

Example 13: Minimum and Maximum Doses for Opioid-Free Intra-Operative Compositions of the Disclosure The minimum and maximum doses in in ml/hr (orig vial) for exemplary opioid-free intra-operative compositions of the disclosure is provided in Table 9.

TABLE 9

| Intra-op Medication Continuous Drip | Time Conversion | Dose Unit Conversion | Duration (hour) | Min Dose in ml/hr (orig vial) | Max Dose in ml/hr (orig vial) | Delta (added) |
|---|---|---|---|---|---|---|
| Lidocaine 2% | 1 | 1 | 1 | 2.5 | 15 | 12.5 |
| Magnesium | 1 | 1 | 1 | 1 | 2 | 1 |
| Dexmedetomidine | 1 | 1 | 1 | 0.1 | 1 | 0.9 |
| Esmolol | 60 | 1000 | 1 | 0.9 | 90 | 89.1 |
| Ketamine | 1 | 1 | 1 | 0.2 | 1 | 0.8 |
| Total Volume | | | | 4.7 | 109 | |

Example 14: Minimum and Maximum Doses for Opioid-Free Intra-Operative Compositions of the Disclosure The minimum and maximum doses in Units Total for exemplary opioid free intra-operative compositions of the disclosure is provided in Table 10.

TABLE 10

| Intra-op Medication Continuous Drip | Minimum Units per ml of Mix | Maximum Units per ml of Mix | Units per 10 ml of mix | Units Conversion | Min Dose (Units Total) | Max Dose (Units Total) | Units |
|---|---|---|---|---|---|---|---|
| Lidocaine 2% | 0.5 | 3 | 0.05 | 1 | 50 | 300 | mg |
| Magnesium | 5 | 10 | 0.5 | 1000 | 0.5 | 1 | g |
| Dexmedetomidine | 0.1 | 1 | 0.01 | 1 | 10 | 100 | mcg |
| Esmolol | 0.18 | 18 | 0.3 | 1000 | 18 | 1800 | mg |
| Ketamine | 0.1 | 0.5 | 0.01 | 1 | 10 | 50 | mg |

Example 15: Opioid-Free Intra-Operative Treatment Methods

Exemplary opioid-free intra-operative compositions and methods of the disclosure are provided in Table 11.

TABLE 11

| Agent | Admin. Mode | Avail. vial conc. | Avail. Vial Vol./forms | Loading Dose | Conc. Ranges for Loading Dose | Infusion Range | Conc. Ranges for Infusion |
|---|---|---|---|---|---|---|---|
| Lidocaine HCl | Injection (IV) | 0.5%, 1%, 1.5% 2%, 4% | 5, 10, 20, 30, 50 ml vials single & multidose vials; 2 & 5 mL ampules; 5 mL syringes & cartridges; Xylocaine ® & Xylocaine MPF ®, | 0-2 mg/kg | 0-35 mg/mL | 1-3 mg/kg/hr | 0.1-35 mg/mL |
| | With dextrose injection (Spinal) | 1.5% w/7.5% dextrose & 5% with 7.5% dextrose | 2 ml ampules & single-does amps; Xylocaine MPF ®, generic; (Rx). | N/A | N/A | N/A | Spinal anesthesia |

TABLE 11-continued

| Agent | Admin. Mode | Avail. vial conc. | Avail. Vial Vol./forms | Loading Dose | Conc. Ranges for Loading Dose | Infusion Range | Conc. Ranges for Infusion |
|---|---|---|---|---|---|---|---|
| | Premixed w/ D5W for IV infusion: (Tumescence; often used for plastic surgery) | 2, 4, 5 mg/ml; w/ epinephrine, topical liquids, patches, ointment, cream, lotion, gel, spray, & jelly available | | N/A | N/A | N/A | Tumescence commonly used for plastic surgery |
| Dex HCl | Injection (IV) | 4 mcg/mL 100 mcg/mL Vet only: 500 mcg/mL | 20 ml multi-dose vials (4 mcg/mL) 2 & 4 ml single use vials (100 mcg/mL) | 0.1-1 mcg/kg | 0.01-50 mcg/mL | 0.1-1 mcg/kg/hr | 0.1-30 mcg/mL |
| Ketamine HCl | Injection (IV) | 10 mg/mL 50 mg/mL 100 mg/mL | 20 ml (10 mg/mL) 10 ml (50 mg/mL) 5 ml (100 mg/mL) | 0-0.5 mg/kg | 0-35 mg/mL | 0-0.5 mg/kg/hr | 0-20 mg/mL |
| Magnesium Chloride | Injection (IV) | 20% (200 mg/mL; 1.97 mEq/mL) | 50 ml multi-dose | 5-50 mg/kg | 1-500 mg/mL | 5-20 mg/kg/hr | 1-370 mg/mL |
| Esmolol Hydrochloride | Injection (IV) | 10 mg/mL 20 mg/mL | 10 ml vial (10 mg/mL) regular and preservative free 100 mL bag-preservative free (Brevibloc ®) 20 mg/mL) | N/A | N/A | 3-300 mcg/kg/min | 0-20 mg/mL |
| Dexamethasone Sodium Phosphate | Injection (IV) | 4 mg/mL 10 mg/mL 20 mg/mL | 1, 5, 10, 30 mL vials (4 mg/mL) 1 mL syringe & 1 mL fill in 2 mL vials 1 & 10 mL vials (10 mg/mL) 5 ml vials (Hexadrol ® Phosphate 20 mg/mL) | 0-.2 mg/kg | 0-10 mg/mL | N/A | N/A |

Example 16: Opioid Consumption and Aldrete Scores Following Administration of OFA and Non-OFA to Patients A study was conducted to evaluate opioid consumption and Aldrete scores in patients who had been administered an anesthesia composition during a medical or surgical procedure. Patients were divided into two cohorts. One cohort (82 patients) received a non-opioid-free anesthesia composition (i.e., one that contained fentanyl) during their medical or surgical procedure. The second cohort (82 patients) received an opioid-free anesthesia intra-operative composition of the disclosure during their medical or surgical procedure. The type of medical or surgical procedures across the two cohorts was vaned and included orthopedic procedures (e.g., ankle arthroscopy, knee arthroscopy, elbow excision, shoulder arthroscopy, and foot bunionectomy), ENT surgeries (e.g., tonsillectomy, functional endoscopic sinus surgery), and GYN surgery (hysterectomy).

As shown in FIG. 4, of the 82 patients in the non-OFA cohort, 30 patients were administered rescue opioids in the PACU (37%). In contrast, only 24 patients in the OFA cohort were administered opioids (29%). Furthermore, of the patients who did receive rescue opioids, the non-OFA cohort required significantly higher doses than the OFA cohort (45 mg vs 29 mg of Demerol). Additionally, the Aldrete readiness for discharge scores of the OFA cohort were superior to the non-OFA cohort at termination of their anesthesia recovery time (9.6 vs 9.4).

FIG. 4 demonstrates reduced post-operative opioid requirement and improved recovery for patients receiving the OFA composition of the disclosure as compared to patients receiving traditional opioid-based anesthetics.

Example 17: Length of Stay Analysis for Patients Receiving OFA

Figure 5:
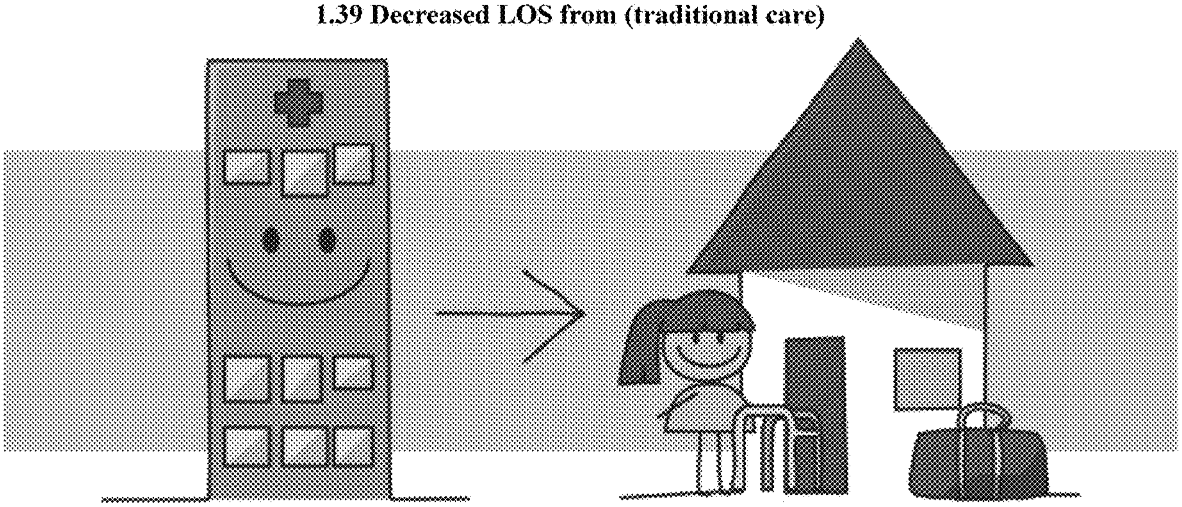

A retrospective analysis was performed on 140 patients who underwent total knee replacement surgery at a hospital. As shown in FIG. 5, patients who received opioid-free compositions of the disclosure and/post-operative opioid-sparing pain management experienced a 50% reduction in hospital length of stay (LOS) after surgery compared to traditional anesthesia care. These patients were able to go home on average 1.39 days sooner than patients who had received traditional anesthesia services. This decrease in LOS can save hospitals significant sums of money.

Many surgeries performed in a hospital require a hospital stay afterwards. The cost for the surgery is paid as a lump sum or as a "bundled payment" instead of itemized billing for each service (e.g., the surgery itself, each day in the hospital, physical therapy, and medications). No other payments are made to the hospital (e.g., complications, extended hospitalization or discharge to a skilled nursing facility). While the patient is hospitalized, the bundled payment includes the payment for nursing staff, pharmacy staff, physical therapy, mediations, food etc. The cost of hospital services collectively are referred to as "adjusted cost" and represent approximate 47% of Medicare reimbursement to the hospital, the remaining 53% is profit. Given this payment model, when the patient is safely discharged early, without readmission (for issues, such as pain control) represents a significant cost savings to the hospital. The daily hospital adjusted cost savings resulting from the early readiness of discharge are provided in FIG. 6. This daily hospital adjusted cost savings, multiplied by the number of days reduced by OFA administration and by the number of surgeries performed, shows that administration of opioid-free anesthesia can provide substantial savings. Importantly, the estimated cost saving does not include the additional potential profit available to hospitals for using the increased hospital vacancy. The estimated cost saving determined here is less than data available from sources such as Becker's Hospital Review and Kaiser foundation.

Example 18: Administration of OFA to a Surgical Patient for an Ankle Repair

A patient undergoing a surgical procedure to repair an ankle fracture was administered an opioid-free intra-operative composition of the disclosure and a popliteal and saphenous nerve block. FIG. 12 shows an X-ray of the ankle fracture fixation following the surgical procedure. The patient's anesthetic record is shown in FIG. 13. The anesthetic record shows minimal changes in the patient's vital signs (sympathetic response) during the surgical procedure.

Example 19: Administration of OFA to a Surgical Patient for a Severe Ankle Fracture Repair A patient undergoing a surgical procedure to repair a severe ankle fracture was administered an opioid-free intra-operative composition of the disclosure. FIG. 14A shows an X-ray of the ankle fracture prior to the surgical procedure. FIG. 14B shows an X-ray of the ankle following the surgical procedure.

The patient woke up comfortable without a block and did not require opioids while in the PACU. Typically, patients who are administered traditional anesthetic compounds are in severe patient post-operatively following this type of repair. It is thus highly unusual that this patient was comfortable and did not require any opioids (pain medications) in the PACU. Importantly, the patient did not end up with chronic pain or chronic opioid use and had not sequela after the surgery. All patents and publications mentioned in the specification are indicative of the levels of skill of those skilled in the art to which the disclosure pertains.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified opioid-free anesthetic composition and related uses to an additional opioid-free anesthetic composition and/or combinations therefore according to various embodiments and scope of the claims.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

REFERENCES

[1]. Friedman B W, Irizarry E, Solórzano C, Zias E, Pearlman S, Wollowitz A, Jones M P, Shah P D, Gallagher E J. A Randomized, Placebo-Controlled Trial of Ibuprofen Plus Metaxalone, Tizanidine, or Baclofen for Acute Low Back Pain. Ann Emerg Med. 2019 October; 74(4):512-520. doi: 10.1016/j.annemergmed.2019.02.017. Epub 2019 Apr. 5.

[2]. ncbi.nlm.nih.gov/pccompound on the world wide web at the date of filing of the present disclosure

[3]. europepmc.org/article/MED/7037502 on the world wide web at the date of filing of the present disclosure

[4]. pubmed.ncbi.nlm.nih.gov/18930723/ on the world wide web at the date of filing of the present disclosure

[5]. europepmc.org/article/MED/6599714 on the world wide web at the date of filing of the present disclosure
[6]. adisinsight.springer.com/drugs/800013220 on the world wide web at the date of filing of the present disclosure
[7]. //pubmed.ncbi.nlm.nih.gov/19826791/ on the world wide web at the date of filing of the present disclosure
[8]. medlineplus.gov/druginfo/meds/a686003.html on the world wide web at the date of filing of the present disclosure
[9]. en.wikipedia.org/wiki/Guanabenz on the world wide web at the date of filing of the present disclosure
[10]. pubchem.ncbi.nlm.nih.gov/compound/Guanabenz on the world wide web at the date of filing of the present disclosure
[11]. rxlist.com/consumer_wytensin_guanabenz/drugs-condition.htm on the world wide web at the date of filing of the present disclosure
[12]. pubchem.ncbi.nlm.nih.gov/compound/Guanoxabenz#section=Names-and-Identifiers on the world wide web at the date of filing of the present disclosure
[13]. pubmed.ncbi.nlm.nih.gov/?cmd=search&term=%22guanoxabenz %22%5BNM %5D on the world wide web at the date of filing of the present disclosure
[14]. en.wikipedia.org/wiki/Guanoxabenz on the world wide web at the date of filing of the present disclosure
[15]. dmd.aspetjoumals.org/content/25/11/1266_on the world wide web at the date of filing of the present disclosure
[16]. pubchem.ncbi.nlm.nih.gov/compound/Guanethidine on the world wide web at the date of filing of the present disclosure
[17]. drugbank.ca/drugs/DB01170 on the world wide web at the date of filing of the present disclosure
[18]. google.com/search?client=safari&rls=en&q=xylazine&ie=UTF-8&oe=UTF-8 on the world wide web at the date of filing of the present disclosure
[19]. ncbi.nlm.nih.gov/pmc/articles/PMC3368046/ on the world wide web at the date of filing of the present disclosure
[20]. watermark.silverchair.com/25-4-245.pdf?token=AQECAHi208BE49Ooan9kkhW_Ercy7Dm3ZL_9Cf3qfKAc485ysgAAAo8wggKLBgkqhkiG9wOBBwagggJ8MIICeAIBADCCAnEGCSqGSIb3DQEHATAeBglghkgBZQMEAS4wEQQMfCCZMP4vOzmzJOLSAgEQgIICQqUfVrTJjzTRRpU7XiGzYUPnVyYaXU-6Juy0y3Zj-Xj56CA2qVhlCeqE8qQ3-JiWfMmqdteQ-QkaKhGwYAdoS8jeR_Z_Yz659paZGTS8bwqA4vBQOeXwdmTCO767iRTb7qlUuFsVU9mRquhi8dSZPo8NDCgZ1Lze7SXnO4yqFc44BNfi00sZzili-3fUWf9FhLEkmRsd66ar9FP8ZXfucYbDka3I5HuB98pc6QVWM_RU6i614L3DoxmC3NiC8WdJMlV9NU4HL9JCzM6PfiiAfDjcTjCwTZNIuD5NRPiMtZzOT4S4FiA3F3XYYtzgMa4f5FOxSVB8PDJc4JoBYmwHHW_wfKJeWtwGdOChmRmQt3nBcELSNdknvNsLuEa9mqSbbtHrRx39ENu9Z60buIK7FCsqQ_3W7N13DqkjUxzaLDKE3JlqIth5tOoX_7pDqR62Qg2mqpOgnZ3Df2etbaqdrUOsgSZUHk8llKaUIpo_WrhQPbvIOxKdy6Gl8SL697xdhdfq5Ozu6A-HNOjmJcXE5mtouvcMtXzqZAPaj5XkaIVKOR9IM5INyoasq32AACexhLW2UVzEps2NGVwRk2I8RH9k21sOWXwFEJJp0yGx8MaLMp8H9DYZGHDYlcNDimLECbh-JdG2ukxhxMnQVtRUytMII5_uOQkjbtOYFwLIvyOGASgBdJFRPO-ftoA_noArH7vunC8bU-oCOZACHSbqGqHy2mdu_uVEkBpi-RosHnOeIaULWcaeel49bxEVyHtIVg_on the world wide web at the date of filing of the present disclosure
[21]. pubchem.ncbi.nlm.nih.gov/compound/5487 on the world wide web at the date of filing of the present disclosure
[22]. clinicaltrials.gov/ct2/show/NCT03068897 on the world wide web at the date of filing of the present disclosure
[23]. clinicaltrials.gov/ct2/show/NCT04429347 on the world wide web at the date of filing of the present disclosure
[24]. pubmed.ncbi.nlm.nih.gov/24641506/* on the world wide web at the date of filing of the present disclosure
[25]. pubchem.ncbi.nlm.nih.gov/compound/Medetomidine at the date of filing of the present disclosure
[26]. ncbi.nlm.nih.gov/mesh/68020926 on the world wide web at the date of filing of the present disclosure
[27]. pubchem.ncbi.nlm.nih.gov/compound/methyldopa on the world wide web at the date of filing of the present disclosure
[28]. pubchem.ncbi.nlm.nih.gov/compound/methyldopa#section=Depositor-Provided-PubMed-Citations&fullscreen=true on the world wide web at the date of filing of the present disclosure
[29]. pubchem.ncbi.nlm.nih.gov/compound/methyldopa#section=Chemical-Co-Occurrences-in-Literature&fullscreen=true on the world wide web at the date of filing of the present disclosure
[30]. pubchem.ncbi.nlm.nih.gov/#query=methylnorepinephrine on the world wide web at the date of filing of the present disclosure
[31]. pubchem.ncbi.nlm.nih.gov/compound/3917#section=Depositor-Provided-PubMed-Citations&fullscreen=true on the world wide web at the date of filing of the present disclosure
[32]. pubchem.ncbi.nlm.nih.gov/compound/123747 on the world wide web at the date of filing of the present disclosure
[33]. pubchem.ncbi.nlm.nih.gov/compound/297812 on the world wide web at the date of filing of the present disclosure
[34]. pubmed.ncbi.nlm.nih.gov/6094346/ on the world wide web at the date of filing of the present disclosure
[35]. medlineplus.gov/druginfo/meds/a601059.html#brand-name-1 on the world wide web at the date of filing of the present disclosure
[36]. pubchem.ncbi.nlm.nih.gov/compound/5743#section=FDA-Pharm-Classes on the world wide web at the date of filing of the present disclosure
[37]. euroanaesthesia2019.org/uploads/2019/06/2019_abstractbook.pdf, on the world wide web at the date of filing of the present disclosure
[38]. ncbi.nlm.nih.gov/pmc/articles/PMC6676158/ on the world wide web at the date of filing of the present disclosure
[39]. sciencedirect.com/topics/medicine-and-dentistry/prilocaine on the world wide web at the date of filing of the present disclosure
[40]. ncbi.nlm.nih.gov/pmc/articles/PMC6087022/ on the world wide web at the date of filing of the present disclosure
[41]. rndsystems.com/target/adrenergic-alpha-2-receptor-agonists on the world wide web at the date of filing of the present disclosure

[42]. pubchem.ncbi.nlm.nih.gov/compound/16757089 on the world wide web at the date of filing of the present disclosure

[43]. pubs.acs.org/doi/10.1021/jm061487a on the world wide web at the date of filing of the present disclosure

[44]. en.wikipedia.org/wiki/(R)-3-Nitrobiphenyline on the world wide web at the date of filing of the present disclosure

[45]. pubmed.ncbi.nlm.nih.gov/?DbFrom=pchierarchy&Cmd=Link&db=pubmed&linkname=pchierarchy_pubmed&from_uid=3293834 on the world wide web at the date of filing of the present disclosure

[46]. rndsystems.com/products/r-m-nitrobiphenyline-oxalate_2948 on the world wide web at the date of filing of the present disclosure

[47]. pubs.acs.org/doi/10.1021/jm100977d on the world wide web at the date of filing of the present disclosure

[48]. pubchem.ncbi.nlm.nih.gov/#query=amitraz on the world wide web at the date of filing of the present disclosure

[49]. pubchem.ncbi.nlm.nih.gov/compound/36324 on the world wide web at the date of filing of the present disclosure

[50]. pubchem.ncbi.nlm.nih.gov/#query=detomidine on the world wide web at the date of filing of the present disclosure

[51]. pubchem.ncbi.nlm.nih.gov/compound/30667#section=NSC-Number on the world wide web at the date of filing of the present disclosure

[52]. pubchem.ncbi.nlm.nih.gov/compound/30667#section=Parent-Compound on the world wide web at the date of filing of the present disclosure

[53]. pubchem.ncbi.nlm.nih.gov/compound/30667#section=Depositor-Provided-PubMed-Citations&fullscreen=true on the world wide web at the date of filing of the present disclosure

[54]. health.harvard.edu/blog/lofexidine-another-option-for-withdrawal-from-opioids-but-is-it-better-2018060614515 on the world wide web at the date of filing of the present disclosure

[55]. en.wikipedia.org/wiki/Lofexidine on the world wide web at the date of filing of the present disclosure

[56]. pubmed.ncbi.nlm.nih.gov/6094346/ on the world wide web at the date of filing of the present disclosure

[57]. medlineplus.gov/druginfo/meds/a601059.html#brand-name-1 on the world wide web at the date of filing of the present disclosure

[58]. Beattie, Scott W & Yang, Homer. Perioperative beta-adrenergic antagonism: panacea or poison?Br J Anaesth. 2019 August; 123(2):97-100

[59]. "Multimodal Analgesia and IV Acetaminophen in the Era of Enhanced Recovery After Surgery and the Perioperative Surgical Home" Clinical Review (2017). "Optimizing the Treatment of Acute Pain in the Emergency Department." Ann Emerg Med 70(3): 446-448. Alam, A., et al. (2012). "Long-term analgesic use after low-risk surgery: a retrospective cohort study." Arch Intern Med 172(5): 425-430.

[60]. Albrecht, E., et al. (2013). "Peri-operative intravenous administration of magnesium sulphate and postoperative pain: a meta-analysis." Anesthesia 68(1): 79-90.

[61]. Aldrete, J. A., et al. (1968). "Does Magnesium Produce Anesthesia? Evaluation of Its Effects on the Cardiovascular and Neurologic Systems." Anesthesia & Analgesia 47(4): 428-433.

[62]. Angst, M. S. and J. D. Clark (2006). "Opioid-induced hyperalgesia: a qualitative systematic review." Anesthesiology 104(3): 570-587.

[63]. Angst, M. S. and J. D. Clark (2010). "Ketamine for Managing Perioperative Pain in Opioid-dependent Patients with Chronic Pain: A Unique Indication?" Anesthesiology 113(3): 514-515.

[64]. Beecher, H. K. (1955). "THE POWERFUL PLACEBO." Journal of the American Medical Association 159(17): 1602-1606.

Berry, P. H. and J. L. Dahl (2000). "The new JCAHO pain standards: Implications for pain management nurses." Pain Management Nursing 1(1): 3-12.

[65]. Biki, B., et al. (2008). "Anesthetic Technique for Radical Prostatectomy Surgery Affects Cancer Recurrence: A Retrospective Analysis." Anesthesiology 109(2): 180-187. Blaudszun, G., et al. (2012). "Effect of Perioperative Systemic a2 Agonists on Postoperative Morphine Consumption and Pain Intensity: Systematic Review and Meta-analysis of Randomized Controlled Trials." Anesthesiology 116(6): 1312-1322.

[66]. Botdorf, J., et al. (2019). Enhanced Recovery After Surgery (ERAS) in the Oncologic Patient. Oncologic Critical Care. J. L. Nates and K. J. Price. Chain, Springer International Publishing: 1-32.

[67]. Califf, R. M., et al. (2016). "A Proactive Response to Prescription Opioid Abuse" The New England Journal of Medicine

[68]. Cassuto, J., et al. (1985). "Inhibition of postoperative pain by continuous low-dose intravenous

[69]. Cèlérier, E., et al. (2000). "Long-lasting Hyperalgesia Induced by Fentanyl in Rats: Preventive Effect of Ketamine." Anesthesiology 92(2): 465-465.

[70]. Cevette, M. J., et al. (2003). "Magnesium and hearing." J Am Acad Audiol 14(4): 202-212.

[71]. Chen, L. and L. Y. Huang (1991). "Sustained potentiation of NMDA receptor-mediated glutamate responses through activation of protein kinase C by a mu opioid." Neuron 7(2): 319-326.

[72]. Chou, R., et al. (2016). "Management of Postoperative Pain: A Clinical Practice Guideline From the American Pain Society, the American Society of Regional Anesthesia and Pain Medicine, and the American Society of Anesthesiologists' Committee on Regional Anesthesia, Executive Committee, and Administrative Council." J Pain 17(2): 131-157.

[73]. Chu, L. F., et al. (2008). "Opioid-induced hyperalgesia in humans: molecular mechanisms and clinical considerations." Clin J Pain 24(6): 479-496.

[74]. Chu, L. F., et al. (2012). "Modulation of remifentanil-induced post infusion hyperalgesia by the β-blocker propranolol in humans." Pain 153(5): 974-981.

[75]. Cohen, V., et al. (2015). "Development of an opioid reduction protocol in an emergency department." American Journal of Health-System Pharmacy 72(23): 2080-2086.

[76]. Collard, V., et al. (2007). "Intraoperative esmolol infusion in the absence of opioids spares postoperative fentanyl in patients undergoing ambulatory laparoscopic cholecystectomy." Anesth Analg 105(5): 1255-1262, table of contents.

[77]. Coloma, M., et al. (2001). "The use of esmolol as an alternative to remifentanil during desflurane anesthesia for fast-track outpatient gynecologic laparoscopic surgery." Anesthesia and analgesia 92(2): 352-357.

[78]. Colvin, L. A. and M. T. Fallon (2010). "Opioid-induced hyperalgesia: a clinical challenge." Br J Anaesth 104(2): 125-127.

[79]. Commission, T. J. (2012). "The Joint Commission Sentinel Event Alert".

[80]. Committee, P. E. (2013). "Advisory Opinion IV Administration of Ketamine for Intractable Pain for Adults".

[81]. Daabiss, M., et al. (2009). "Assessment of different concentration of Ketofol in procedural operation." British Journal of Medical Practitioners.

[82]. Dahl, J. B. and H. Kehlet (2011). "Preventive analgesia." Curr Opin Anaesthesiol 24(3): 331-338.

[83]. De Clive-Lowe, S. G., et al. (1958). "Intravenous lignocaine anaesthesia." Anaesthesia 13(2): 138-146.

[84]. De Oliveira, G. S., Jr, et al. (2013). "Perioperative Systemic Magnesium to Minimize Postoperative Pain: A Meta-analysis of Randomized Controlled Trials." Anesthesiology 119(1): 178-190.

[85]. Devereaux, P. J. and Daniel I. Sessler (2012). "The Potential Role of a2Agonists for Noncardiac Surgery." Anesthesiology 116(6): 1192-1194.

[86]. Dirks, J., et al. (2002). "A randomized study of the effects of single-dose gabapentin versus placebo on postoperative pain and morphine consumption after mastectomy." Anesthesiology 97(3): 560-564.

[87]. Dowell, D., et al. (2016). "CDC Guideline for Prescribing Opioids for Chronic Pain-United States, 2016." JAMA 315(15): 1624-1645.

[88]. Eisenach, J. C. (2000). "Preemptive Hyperalgesia, Not Analgesia?" Anesthesiology 92(2): 308-308.

Elsharnouby, N. M. and M. M. Elshamouby (2006). "Magnesium sulphate as a technique of hypotensive anaesthesia." Br J Anaesth 96(6): 727-731.

[89]. Elvir-Lazo, O. L. and P. F. White (2010). "The role ofmultimodal analgesia in pain management after ambulatory surgery." Curr Opin Anaesthesiol 23(6): 697-703.

[90]. Exadaktylos, A. K., et al. (2006). "Can anesthetic technique for primary breast cancer surgery affect recurrence or metastasis?" Anesthesiology 105(4): 660-664.

[91]. Fassoulaki, A., et al. (2005). "Multimodal analgesia with gabapentin and local anesthetics prevents acute and chronic pain after breast surgery for cancer." Anesth Analg 101(5): 1427-1432.

[92]. Fawcett, W. J., et al. (1999). "Magnesium: physiology and pharmacology." Br J Anaesth 83(2): 302-320.

[93]. Feld, J. M., et al. (2003). "Non-opioid analgesia improves pain relief and decreases sedation after gastric bypass surgery." Can J Anaesth 50(4): 336-341.

[94]. Fordtran, J. S. (1977). "Presidential Address before the 69th Annual Meeting of the American Society for Clinical Investigation" The Journal of Clinical Investigation Forget, P., et al. (2010). "Do intraoperative analgesics influence breast cancer recurrence after mastectomy? A retrospective analysis." Anesth Analg 110(6): 1630-1635.

[95]. Fundytus, M. (2001). "Glutamate receptors and nociception: Implications for the drug treatment of pain." CNS Drugs 15: 29-58.

[96]. Golzari, S. E., et al. (2014). "Lidocaine and pain management in the emergency department: a review article." Anesth Pain Med 4(1): e15444.

[97]. Gottschalk, A. and D. S. Smith (2001). "New concepts in acute pain therapy: preemptive analgesia." Am Fam Physician 63(10): 1979-1984.

[98]. Grady, M. V., et al. (2012). "The effect of perioperative intravenous lidocaine and ketamine on recovery after abdominal hysterectomy." Anesth Analg 115(5): 1078-1084.

[99]. Grigoras, A., et al. (2012). "Perioperative intravenous lidocaine decreases the incidence of persistent pain after breast surgery." Clin J Pain 28(7): 567-572.

[100]. Guignard, B., et al. (2000). "Acute Opioid Tolerance: Intraoperative Remifentanil Increases Postoperative Pain and Morphine Requirement." Anesthesiology 93(2): 409-417.

[101]. Gupta, K., et al. (2006). "The role of magnesium as an adjuvant during general anaesthesia." Anaesthesia 61(11): 1058-1063.

[102]. Hahnenkamp, K., et al. (2006). "Local anaesthetics inhibit signalling of human NMDA receptors recombinantly expressed in *Xenopus laevis* oocytes: role of protein kinase C." Br J Anaesth 96(1): 77-87.

[103]. Hayhurst, C. J. and M. E. Durieux (2016). "Differential Opioid Tolerance and Opioid-induced Hyperalgesia: A Clinical Reality." Anesthesiology 124(2): 483-488.

[104]. Himes, Richard S., J R., et al. (1977). "Effects of Lidocaine on the Anesthetic Requirements for Nitrous Oxide and Halothane." Anesthesiology 47(5): 437-440.

[105]. Hofer, R. E., et al. (2005). "Anesthesia for a patient with morbid obesity using dexmedetomidine without narcotics." Can J Anaesth 52(2): 176-180.

[106]. Hollmann, M. W., et al. (2001). "Modulation of NMDA receptor function by ketamine and magnesium. Part II: interactions with volatile anesthetics." Anesth Analg 92(5): 1182-1191.

[107]. Howard, M. L., et al. (2018). "Continuous Infusion Nonsteroidal Anti-Inflammatory Drugs for Perioperative Pain Management." J Pharm Pract 31(1): 66-81.

[108]. Ilkjaer, S., et al. (1996). "Effect of systemic N-methyl-D-aspartate receptor antagonist (ketamine) on primary and secondary hyperalgesia in humans." Br J Anaesth 76(6): 829-834.

[109]. Iseri, L. T. and J. H. French (1984). "Magnesium: nature's physiologic calcium blocker." Am HeartJ 108(1): 188-193.

[110]. Issioui, T., et al. (2002). "The efficacy of premedication with celecoxib and acetaminophen in preventing pain after otolaryngologic surgery." Anesth Analg 94(5): 1188-1193, table of contents.

[111]. Jabbour, H. J., et al. (2014). "Ketamine and magnesium association reduces morphine consumption after scoliosis surgery: prospective randomised double-blind study." Acta Anaesthesiol Scand 58(5): 572-579.

[112]. Jahnen-Dechent, W. and M. Ketteler (2012). "Magnesium basics." Clin Kidney J 5(Suppl 1): i3-i14.

[113]. James, M. F., et al. (1989). "Intravenous magnesium sulfate inhibits catecholamine release associated with tracheal intubation." Anesth Analg 68(6): 772-776.

[114]. James, M. F. M. (1992). "Clinical Use of Magnesium Infusions in Anesthesia." Anesthesia & Analgesia 74(1): 129-136.

[115]. James, M. F. M. (2009). "Magnesium: an emerging drug in anaesthesia." BJA: British Journal of Anaesthesia 103(4): 465-467.

[116]. Joshi, G. P., et al. (2014). "Procedure-specific pain management and outcome strategies." Best Pract Res Clin Anaesthesiol 28(2): 191-201.

[117]. Kamibayashi, T., et al. (2000). "Clinical Uses of a2-Adrenergic Agonists." Anesthesiology 93(5): 1345-1349.

[118]. Kara, H., et al. (2002). "Magnesium infusion reduces perioperative pain." Eur J Anaesthesiol 19(1): 52-56.
[119]. Kaye, P. and I. O'Sullivan (2002). "The role of magnesium in the emergency department." Emerg Med J 19(4): 288-291.
[120]. Kehlet, H. (2006). "Labat lecture 2005: surgical stress and postoperative outcome-from here to where?" Reg Anesth Pain Med 31(1): 47-52.
[121]. Kehlet, H. and J. B. Dahl (1993). "The Value of "Multimodal" or "Balanced Analgesia" in Postoperative Pain Treatment." Anesthesia & Analgesia 77(5): 1048-1056.
[122]. Kehlet, H. and J. B. Dahl (2003). "Anaesthesia, surgery, and challenges in postoperative recovery." Lancet 362(9399): 1921-1928.
[123]. Kharasch, E. D. (2015). "Opioid Half-lives and Hemlines: The Long and Short of Fashion." Anesthesiology 122(5): 969-970.
[124]. Kharasch, E. D. and L. M. Brunt (2016). "Perioperative Opioids and Public Health." Anesthesiology 124(4): 960-965.
[125]. Kharasch, E. D. and J. C. Eisenach (2016). "Wherefore Gabapentinoids?: Was There Rush Too Soon to Judgment?" Anesthesiology 124(1): 10-12.
[126]. Kissin, I. (2011). "A call to reassess the clinical value of preventive (preemptive) analgesia." Anesth Analg 113 (5): 977-978.
[127]. Krasner, B. S. (1979). "Cardiac effects of magnesium with special reference to anaesthesia: a review." Canadian Anaesthetists' Society Journal 26(3): 181-185.
[128]. Lee, M., et al. (2011). "A comprehensive review of opioid-induced hyperalgesia." Pain Physician 14(2): 145-161.
[129]. Lennon, Frances E., et al. (2012). "The μ-Opioid Receptor in Cancer Progression: Is There a Direct Effect?" Anesthesiology 116(4): 940-945.
[130]. Levaux, C., et al. (2003). "Effect of intra-operative magnesium sulphate on pain relief and patient comfort after major lumbar orthopaedic surgery." Anaesthesia 58(2): 131-135.
[131]. Liu, H. T., et al. (2001). "Modulation of NMDA receptor function by ketamine and magnesium: Part I." Anesth Analg 92(5): 1173-1181.
[132]. Loftus, R. W., et al. (2010). "Intraoperative Ketamine Reduces Perioperative Opiate Consumption in Opiate-dependent Patients with Chronic Back Pain Undergoing Back Surgery." Anesthesiology 113(3): 639-646.
[133]. Luk, L. J., et al. (2016). "Implementation of a Pediatric Posttonsillectomy Pain Protocol in a Large Group Practice." Otolaryngol Head Neck Surg 154(4): 720-724.
[134]. Lysakowski, C., et al. (2007). "Magnesium as an adjuvant to postoperative analgesia: a systematic review of randomized trials." Anesth Analg 104(6): 1532-1539, table of contents.
[135]. Mathew, S. J., et al. (2012). "Ketamine for treatment-resistant unipolar depression: current evidence." CNS Drugs 26(3): 189-204.
[136]. Mauermann, E., et al. (2016). "Does Fentanyl Lead to Opioid-induced Hyperalgesia in Healthy Volunteers?: A Double-blind, Randomized, Crossover Trial." Anesthesiology 124(2): 453-463.
[137]. Mauermann, E., et al. (2017). "Different protocols used today to achieve total opioid-free general anesthesia without locoregional blocks." Best Pract Res Clin Anaesthesiol 31(4): 533-545.
[138]. Mauskop, A. and J. Varughese (2012). "Why all migraine patients should be treated with magnesium." J Neural Transm (Vienna) 119(5): 575-579.
[139]. McCarthy, G. C., et al. (2010). "Impact of intravenous lidocaine infusion on postoperative analgesia and recovery from surgery: a systematic review of randomized controlled trials." Drugs 70(9): 1149-1163.
[140]. McKay, A., et al. (2009). "Systemic lidocaine decreased the perioperative opioid analgesic requirements but failed to reduce discharge time after ambulatory surgery." Anesth Analg 109(6): 1805-1808.
[141]. Meltzer, A. (1990). "Dr. Samuel James Meltzer and intratracheal anesthesia." Journal of Clinical Anesthesia 2(1): 54-58.
[142]. Meltzer, A. (1990). "Dr. Samuel James Meltzer: physiologist of the Rockefeller Institute." Am Jew Arch 42(1): 49-56.
[143]. Menigaux, C., et al. (2000). "The benefits of intraoperative small-dose ketamine on postoperative pain after anterior cruciate ligament repair." Anesth Analg 90(1): 129-135.
[144]. Minville, V., et al. (2009). "Opioid-induced hyperalgesia in a mice model of orthopaedic pain: preventive effect of ketamine†." BJA: British Journal of Anaesthesia 104(2): 231-238.
[145]. Møiniche, S., et al. (2002). "A qualitative and quantitative systematic review of preemptive analgesia for postoperative pain relief: the role of timing of analgesia." Anesthesiology 96(3): 725-741.
[146]. Mortero, R. F., et al. (2001). "The effects of small-dose ketamine on propofol sedation: respiration, postoperative mood, perception, cognition, and pain." Anesth Analg 92(6): 1465-1469.
[147]. Motov, S., et al. (2015). "Intravenous Subdissociative-Dose Ketamine Versus Morphine for Analgesia in the Emergency Department: A Randomized Controlled Trial." Annals of Emergency Medicine 66(3): 222-229.e221.
[148]. Mulier, J. (2019). "Is opioid-free general anesthesia for breast and gynecological surgery a viable option?" Current Opinion in Anaesthesiology 32: 257 262.
[149]. Mulier, J. P. and B. Dillemans (2019). "Anaesthetic Factors Affecting Outcome After Bariatric Surgery, a Retrospective Levelled Regression Analysis." Obes Surg 29(6): 1841-1850. Munir, M. A., et al. (2007). "Nonopioid analgesics." Med Clin North Am 91(1): 97-111.
[150]. Myles, P. S., et al. (2000). "Validity and reliability of a postoperative quality of recovery score: the QoR-40." Br J Anaesth 84(1): 11-15.
[151]. Naidu, R. and P. Flood (2013). "Magnesium: is there a signal in the noise?" Anesthesiology 119(1): 13-15.
[152]. Nassif, G. J. and T. E. Miller (2019). "Evolving the management of acute perioperative pain towards opioid-free protocols: a narrative review." Curr Med Res Opin 35(12): 2129-2136.
[153]. Olsen, Y. (2016). "The CDC Guideline on Opioid Prescribing: Rising to the Challenge." JAMA 315(15): 1577-1579.
[154]. Ong, C. K., et al. (2005). "The efficacy of preemptive analgesia for acute postoperative pain management: a meta-analysis." Anesth Analg 100(3): 757-773, table of contents.
[155]. Ozcan, P. E., et al. (2007). "Role of magnesium sulfate in postoperative pain management for patients undergoing thoracotomy." J Cardiothorac Vasc Anesth 21(6): 827-831.

[156]. Padda, G. S., et al. (1997). "Comparison of postoperative emesis, recovery profile, and analgesia in pediatric strabismus repair. Rectal acetaminophen versus intravenous fentanyl-droperidol." Ophthalmology 104(3): 419-424.
[157]. Panda, N. B., et al. (2013). "Minimal effective dose of magnesium sulfate for attenuation of intubation response in hypertensive patients." J Clin Anesth 25(2): 92-97.
[158]. Philip, B. K., et al. (2002). "The economic impact of opioids on postoperative pain management." Journal of Clinical Anesthesia 14(5): 354-364.
[159]. Ramaswamy, S., et al. (2013). "Non-opioid-based adjuvant analgesia in perioperative care." Continuing Education in Anaesthesia Critical Care & Pain 13(5): 152-157.
[160]. Reich, D. L. and G. Silvay (1989). "Ketamine: an update on the first twenty-five years of clinical experience." Can J Anaesth 36(2): 186-197.
[161]. Richebé, P., et al. (2005). "Ketamine improves the management of exaggerated postoperative pain observed in perioperative fentanyl-treated rats." Anesthesiology 102(2): 421-428.
[162]. Rivat, C. and J. Ballantyne (2016). "The dark side of opioids in pain management: basic science explains clinical observation." PAIN Reports 1(2): e570.
[163]. Rivat, C., et al. (2007). "Non-nociceptive environmental stress induces hyperalgesia, not analgesia, in pain and opioid-experienced rats." Neuropsychopharmacology 32(10): 2217-2228.
[164]. Rivkin, A. and M. A. Rivkin (2014). "Perioperative nonopioid agents for pain control in spinal surgery." Am J Health Syst Pharm 71(21): 1845-1857.
[165]. Roytblat, L., et al. (1993). "Postoperative Pain: The Effect of Low-Dose Ketamine in Addition to General Anesthesia." Anesthesia & Analgesia 77(6): 1161-1165.
[166]. Ryan, W. C., et al. (2014). "Ketamine and Depression: A Review" International Journal of Transpersonal Studies
[167]. Ryu, J. H., et al. (2009). "Controlled hypotension for middle ear surgery: a comparison between remifentanil and magnesium sulphatet this article is accompanied by Editorial I." British Journal of Anaesthesia 103(4): 490-495.
[168]. Sacerdote, P., et al. (1997). "Antinociceptive and immunosuppressive effects of opiate drugs: a structure-related activity study." Br J Pharmacol 121(4): 834-840.
[169]. Samuels, D. (2017). "Opiod-free Anesthesia Results in Reduced Post-operative Opioid Consumption." Journal of Clinical Anesthesia and Pain Medicine
[170]. Sanders, J. G. and P. J. Dawes (2016). "Gabapentin for Perioperative Analgesia in Otorhinolaryngology-Head and Neck Surgery: Systematic Review." Otolaryngol Head Neck Surg 155(6): 893-903.
[171]. Schmid, R. L., et al. (1999). "Use and efficacy of low-dose ketamine in the management of acute postoperative pain: a review of current techniques and outcomes." Pain 82(2): 111-125.
[172]. Schumann, R., et al. (2016). "High-flow nasal oxygen availability for sedation decreases the use of general anesthesia during endoscopic retrograde cholangiopancreatography and endoscopic ultrasound." World J Gastroenterol 22(47): 10398-10405.
[173]. Schwenk, E. S., et al. (2016). "Adverse Drug Effects and Preoperative Medication Factors Related to Perioperative Low-Dose Ketamine Infusions." Reg Anesth Pain Med 41(4): 482-487.
[174]. Seyhan, T. O., et al. (2006). "Effects of three different dose regimens of magnesium on propofol requirements, haemodynamic variables and postoperative pain relief in gynaecological surgery." Br J Anaesth 96(2): 247-252.
[175]. Shafi, S., et al. (2018). "Association of Opioid-Related Adverse Drug Events With Clinical and Cost Outcomes Among Surgical Patients in a Large Integrated Health Care Delivery System." JAMA Surg 153(8): 757-763.
[176]. Shanthanna, H. "Intravenous Therapies in the Management of Neuropathic Pain: A Review on the Use of Ketamine and Lidocaine in Chronic Pain Management" McMaster University, Michael DeGroote School of Medicine Canada.
[177]. Singh, J. B., et al. (2016). "A Double-Blind, Randomized, Placebo-Controlled, Dose-Frequency Study of Intravenous Ketamine in Patients With Treatment-Resistant Depression." Am J Psychiatry 173(8): 816-826.
[178]. Soave, P. M., et al. (2009). "Magnesium and anaesthesia." Curr Drug Targets 10(8): 734-743.
[179]. Sobel, R. M., et al. (1999). "Ketamine in the ED: Medical politics versus patient care." The American Journal of Emergency Medicine 17(7): 722-725.
[180]. Sobey, C., et al. (2016). "Postoperative Ketamine: Time for a Paradigm Shift." Regional Anesthesia and Pain Medicine 41: 424-426.
[18]. Son, J. S. and S. Ko (2011). "Does intraoperative remifentanil infusion really make more postoperative pain?" Korean J Anesthesiol 61(3): 187-189.
[182]. Spahn, Donat R. and C. Madjdpour (2006). "Physiologic Transfusion Triggers: Do We Have to Use (Our) Brain?" Anesthesiology 104(5): 905-906.
[183]. Stanley, T. H., et al. (2008). "A tribute to Dr. Paul A. J. Janssen: entrepreneur extraordinaire, innovative scientist, and significant contributor to anesthesiology." Anesth Analg 106(2): 451-462, table of contents.
[184]. Sultana, A. "Opioid-Free Anesthesia and Analgesia in the Bariatric Patient." Telci, L., et al. (2002). "Evaluation of effects of magnesium sulphate in reducing intraoperative anaesthetic requirements." Br J Anaesth 89(4): 594-598.
[185]. Thiels, C. A., et al. (2017). "Wide Variation and Overprescription of Opioids After Elective Surgery." Annals of Surgery 266(4): 564-573.
[186]. Thiels, C. A., et al. (2018). "Results of a Prospective, Multicenter Initiative Aimed at Developing Opioid-prescribing Guidelines After Surgery." Ann Surg 268(3): 457-468.
[187]. Thompson, S. W., et al. (1988). "The anesthetic contribution of magnesium sulfate and ritodrine hydrochloride in rats." Anesth Analg 67(1): 31-34. Tovell, R. M. (1931). "Intratracheal Anesthesia.*." Anesthesia & Analgesia 10(3): 97-103.
[188]. Tremont-Lukats, I. W., et al. (2005). "Systemic administration of local anesthetics to relieve neuropathic pain: a systematic review and meta-analysis." Anesth Analg 101(6): 1738-1749.
[189]. Turan, A. and D. I. Sessler (2011). "Steroids to ameliorate postoperative pain." Anesthesiology 115(3): 457-459.
[190]. van Velzen, M. and A. Dahan (2014). "Ketamine Metabolomics in the Treatment of Major Depression." Anesthesiology 121(1): 4-5.
[191]. Van Zee, A. (2009). "The promotion and marketing of oxycontin: commercial triumph, public health tragedy." Am J Public Health 99(2): 221-227.

[192]. Vanstone, R. J. and M. Rockett (2016). "Use of atypical analgesics by intravenous infusion (IV) for acute pain: evidence base for lidocaine, ketamine and magnesium." Anaesthesia & Intensive Care Medicine 17(9): 460-463.

[193]. Vigneault, L., et al. (2011). "Perioperative intravenous lidocaine infusion for postoperative pain control: a meta-analysis of randomized controlled trials." Can J Anaesth 58(1): 22-37.

[194]. Watcha, M. F., et al. (1992). "Comparison of ketorolac and morphine as adjuvants during

[195]. Weinger, M. B. (Winter 2006-2007). "Dangers of Postoperative Opioids" The Official Journal of the Anesthesia Patient Safety Foundation.

[196]. Werner, M. U., et al. (2010). "Prediction of postoperative pain: a systematic review of predictive experimental pain studies." Anesthesiology 112(6): 1494-1502.

[197]. White, P. F. (2002). "The role of non-opioid analgesic techniques in the management of pain after ambulatory surgery." Anesth Analg 94(3): 577-585.

[198]. White, P. F. and H. Kehlet (2010). "Improving postoperative pain management: what are the unresolved issues?" Anesthesiology 112(1): 220-225.

[199]. White, P. F., et al. (2007). "The role of the anesthesiologist in fast-track surgery: from multimodal analgesia to perioperative medical care." Anesth Analg 104(6): 1380-1396, table of

[200]. White, P. F., et al. (2012). "Ketorolac: its role as part of a multimodal analgesic regimen." Anesth Analg 114 (2): 250-254.

[201]. White, P. F., et al. (2003). "The Effect of Intraoperative Use of Esmolol and Nicardipine on Recovery After Ambulatory Surgery." Anesthesia & Analgesia 97(6): 1633-1638.

[202]. Wieronska, J. M., et al. (2012). "Depression Viewed as a GABA/Glutamate Imbalance in the Central Nervous System." Clinical, Research and Treatment Approaches to Affective Disorders.

[203]. Wilder-Smith, C. H., et al. (1997). "Perioperative magnesium infusion and postoperative pain." Acta Anaesthesiol Scand 41(8): 1023-1027.

[204]. Woolf, C. J. and S. W. N. Thompson (1991). "The induction and maintenance of central sensitization is dependent on N-methyl-d-aspartic acid receptor activation; implications for the treatment of post-injury pain hypersensitivity states." Pain 44(3): 293-299.

[205]. Wu, C. L. and S. S. Liu (2009). "Intravenous Lidocaine for Ambulatory Anesthesia: Good to Go or Not So Fast?" Anesthesia & Analgesia 109(6): 1718-1719.

[206]. Wu, Christopher L. and Srinivasa N. Raja (2002). "Optimizing Postoperative Analgesia: The Use of Global Outcome Measures." Anesthesiology 97(3): 533-534.

[207]. Wyles, C. C., et al. (2019). "The 2018 Chitranjan S. Ranawat, MD Award: Developing and Implementing a Novel Institutional Guideline Strategy Reduced Postoperative Opioid Prescribing After TKA and THA." Clinical Orthopaedics and Related Research® 477(1): 104-113.

[208]. Yang, H. and A. Fayad (2003). "Are J-blockers anesthestics?" Canadian Journal of Anaesthesia 50(7): 627-630.

[209]. Young, K. H., et al. (2016). "Tuberculosis Contact Investigations-United States, 2003-2012." MMWR. Morbidity and mortality weekly report 64 50-51: 1369-1374.

[210]. Seifen et al. (1979). "Pharmacokinetics of Intravenous Procaine Infusion in Humans." ANESTH ANALG, 58:382-386.

[211]. G. Ulufer Sivrikaya (2012). Multimodal Analgesia for Postoperative Pain Management, Pain Management—Current Issues and Opinions, Dr. Gabor Racz (Ed.), ISBN: 978-953-307-813-7.

[212]. SOFA Medication Clinical Reference Tool, The Society for Opioid Free Anesthesia, 29 pages The Society for Opioid Free Anesthesia. (2019). *SOFA medication clinical reference tool* [Brochure]. Retrieved Oct. 24, 2010, from goopioidfree.com on the world wide web

The invention claimed is:

1. A vial or an IV bag comprising an opioid-free intra-operative pharmaceutical composition comprising: a magnesium salt comprising magnesium sulfate, an alpha-2 agonist comprising dexmedetomidine, a sodium channel inhibitor comprising lidocaine, prilocaine or procaine, an NMDA antagonist comprising ketamine, and a beta-blocker comprising esmolol, wherein the magnesium sulfate, dexmedetomidine, lidocaine, prilocaine or procaine, ketamine, and esmolol are comprised in an effective amount in said vial or IV bag for sedation and/or analgesia.

2. A method for an opioid-free intra-operative treatment of an individual undergoing a medical or surgical procedure, the method comprising, administering to the individual an effective amount of a composition of claim 1 in a vial or an IV bag of claim 1.

* * * * *